United States Patent
D'Ambrosio et al.

(10) Patent No.: US 12,392,769 B1
(45) Date of Patent: Aug. 19, 2025

(54) AMBIENT CONTAMINATION IN BREATH ANALYTE DETECTION AND MEASUREMENT

(71) Applicant: Hound Labs, Inc., Oakland, CA (US)

(72) Inventors: Michael V. D'Ambrosio, Berkeley, CA (US); Daniel H. Friedman, Mountain View, CA (US); Jeffrey A. Stoll, San Mateo, CA (US); Michael Scott Lynn, Piedmont, CA (US)

(73) Assignee: Hound Labs, Inc., Oakland, CA (US)

( * ) Notice: Subject to any disclaimer, the term of this patent is extended or adjusted under 35 U.S.C. 154(b) by 253 days.

(21) Appl. No.: 17/573,560

(22) Filed: Jan. 11, 2022

Related U.S. Application Data

(60) Provisional application No. 63/228,023, filed on Jul. 31, 2021, provisional application No. 63/203,820, filed on Jul. 30, 2021, provisional application No. 63/201,062, filed on Apr. 9, 2021, provisional application No. 63/199,696, filed on Jan. 18, 2021, provisional application No. 63/199,610, filed on Jan. 12, 2021.

(51) Int. Cl.
*G01N 33/497* (2006.01)
*G01N 33/00* (2006.01)

(52) U.S. Cl.
CPC ....... *G01N 33/497* (2013.01); *G01N 33/0047* (2013.01); *G01N 33/4975* (2024.05)

(58) Field of Classification Search
CPC .. G01N 1/22; G01N 33/0004; G01N 33/0009; G01N 33/0027; G01N 33/0036; G01N 33/0047; G01N 33/497; G01N 2033/4975
See application file for complete search history.

(56) References Cited

U.S. PATENT DOCUMENTS

| | | |
|---|---|---|
| 5,196,306 A | 3/1993 | Bobrow et al. |
| 5,230,866 A | 7/1993 | Shartle et al. |
| 5,583,001 A | 12/1996 | Bobrow et al. |
| 5,731,158 A | 3/1998 | Bobrow et al. |
| 6,727,067 B2 | 4/2004 | Russman et al. |
| 6,750,065 B1 * | 6/2004 | White .......... G01N 33/582 |
| | | 436/805 |
| 6,780,617 B2 | 8/2004 | Chen |
| 6,964,862 B2 | 11/2005 | Chen |
| 7,337,072 B2 | 2/2008 | Chen |
| 7,718,421 B2 | 5/2010 | Chen et al. |
| 7,799,521 B2 | 9/2010 | Chen |

(Continued)

FOREIGN PATENT DOCUMENTS

WO  WO-2018076099 A1 * 5/2018 ............ A61B 5/08

OTHER PUBLICATIONS

U.S. Appl. No. 62/705,860, filed Jul. 17, 2020, Friedman et al.

(Continued)

*Primary Examiner* — Benjamin R Schmitt
(74) *Attorney, Agent, or Firm* — Mahamedi IP Law LLP

(57) ABSTRACT

Accurate measurement of breath-borne analyte(s) is disclosed, in which such a measurement can be compared to a background level of the analyte(s) in an ambient air sample. Methods, systems, and devices can include use of this background level for the purposes of detection and/or measurement of an analyte (e.g., THC) in breath samples of for law enforcement, health, and safety applications.

29 Claims, 21 Drawing Sheets

(56) References Cited

U.S. PATENT DOCUMENTS

| | | |
|---|---|---|
| 7,833,489 B2 | 11/2010 | Chen |
| 7,935,504 B2 | 5/2011 | Chen |
| 8,148,116 B2 | 4/2012 | Chen |
| 8,936,933 B2 | 1/2015 | Chen et al. |
| 9,662,652 B2 | 5/2017 | Chen |
| 9,708,599 B2 | 7/2017 | Chen et al. |
| 9,709,582 B1* | 7/2017 | Gordon ................ G01N 33/582 |
| 10,443,050 B2 | 10/2019 | Chen et al. |
| 2011/0014719 A1* | 1/2011 | Sijbers ............. G01N 33/54373 |
| | | 422/68.1 |
| 2017/0122851 A1 | 5/2017 | Thatcher et al. |
| 2018/0246036 A1* | 8/2018 | Carty ................... G01J 3/4406 |
| 2019/0086432 A1* | 3/2019 | Tran ................... G01N 33/4972 |
| 2019/0307396 A1* | 10/2019 | Attariwala ........... A61B 5/4845 |

OTHER PUBLICATIONS

U.S. Appl. No. 62/706,306, filed Aug. 7, 2020, Friedman et al.
U.S. Appl. No. 63/198,388, filed Oct. 14, 2020, D'Ambrosio et al.
U.S. Appl. No. 63/198,697, filed Nov. 5, 2020, Friedman et al.
U.S. Appl. No. 63/201,389, filed Apr. 27, 2021, Lynn et al.

* cited by examiner

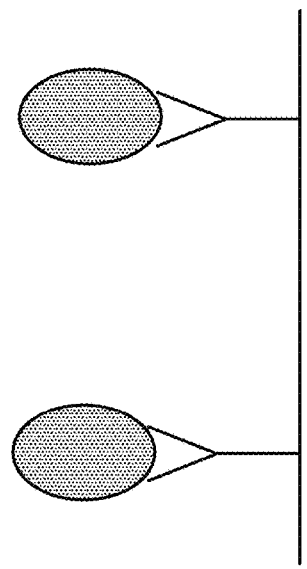
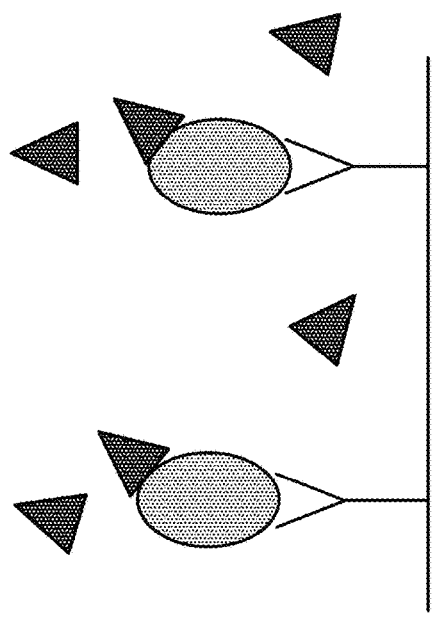
FIG. 5A
FIG. 5B
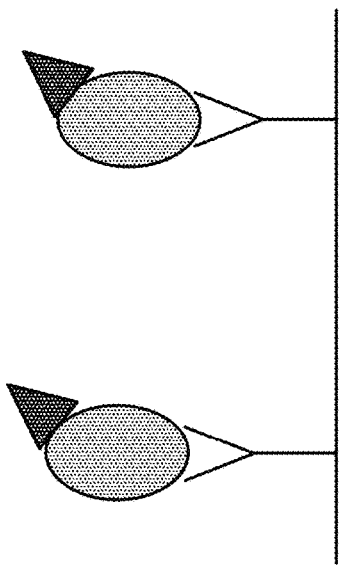
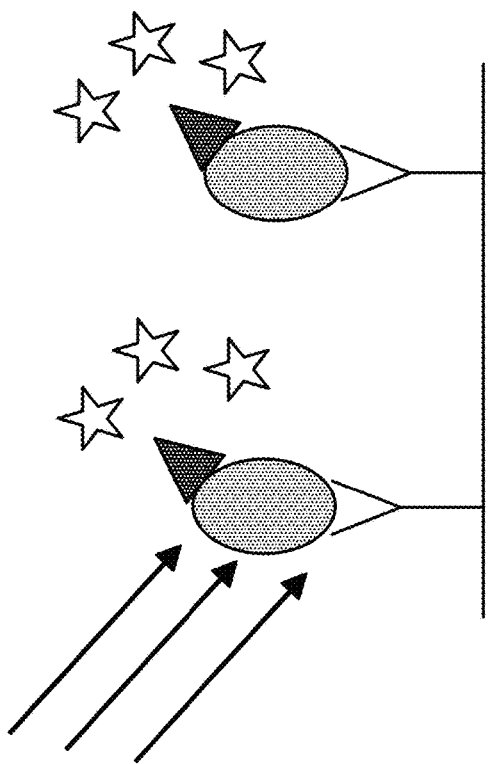
FIG. 5C
FIG. 5D

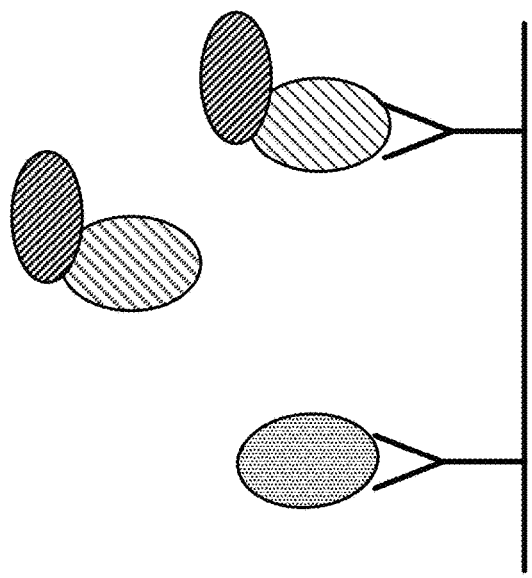
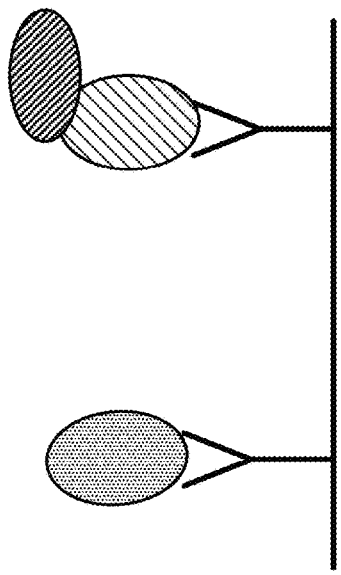
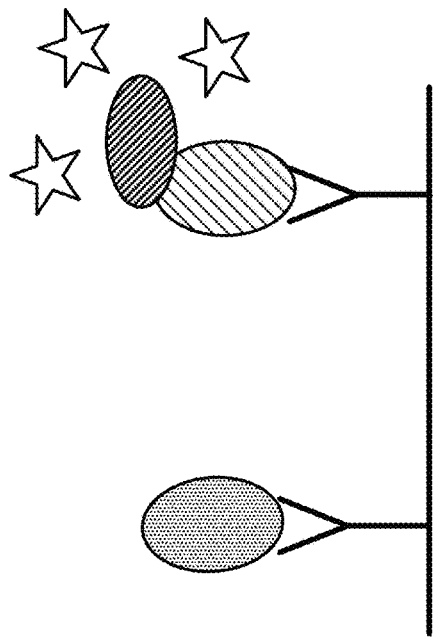

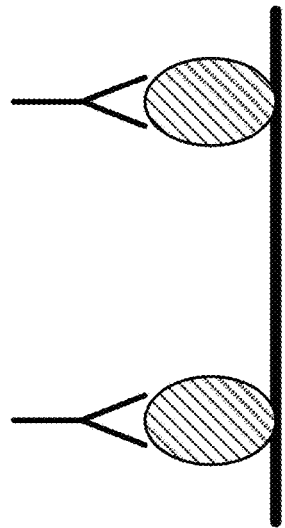
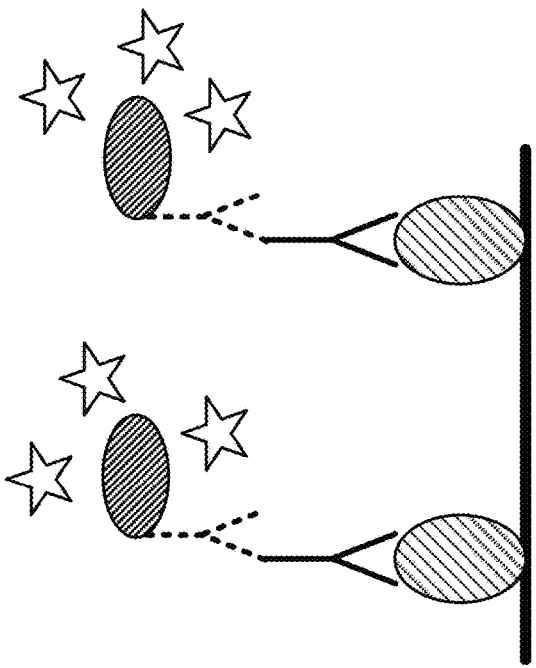
FIG. 8B
FIG. 8D
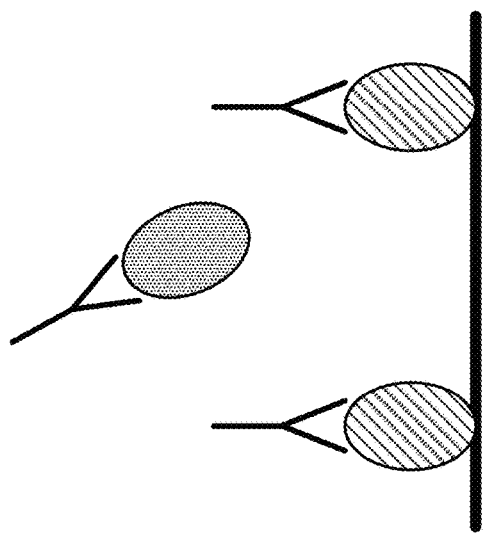
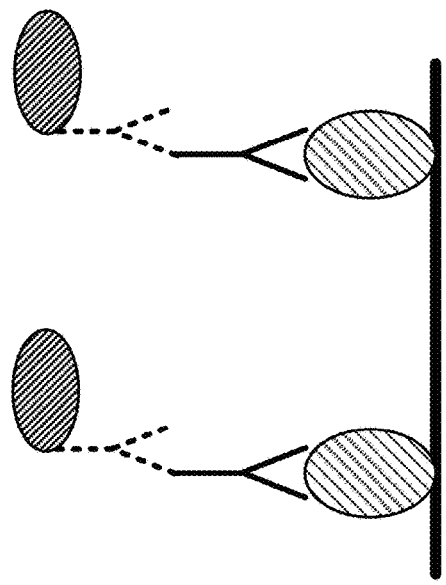
FIG. 8A
FIG. 8C

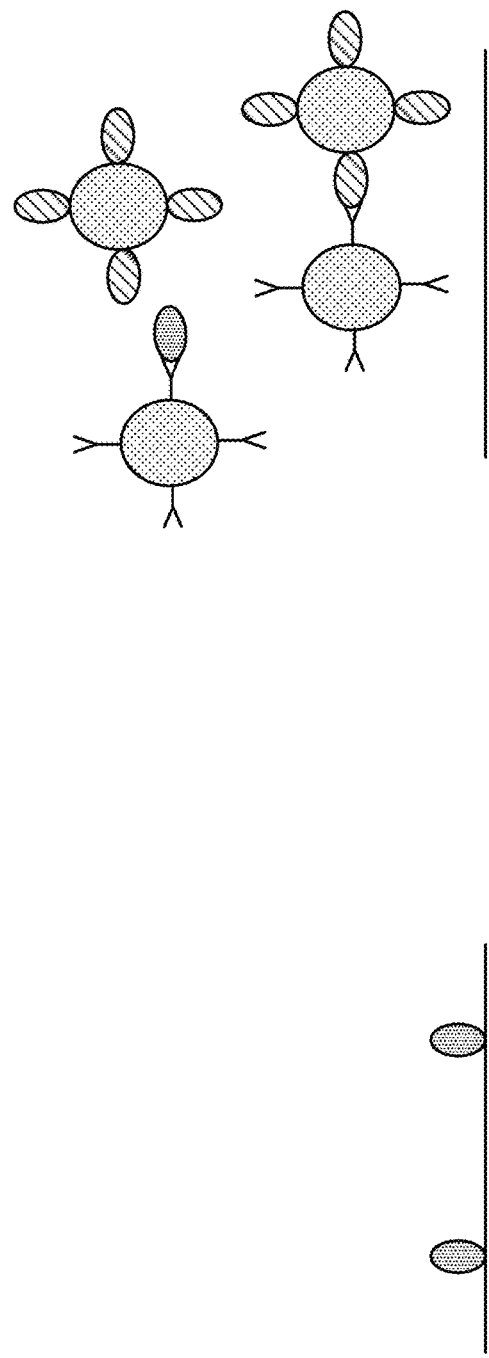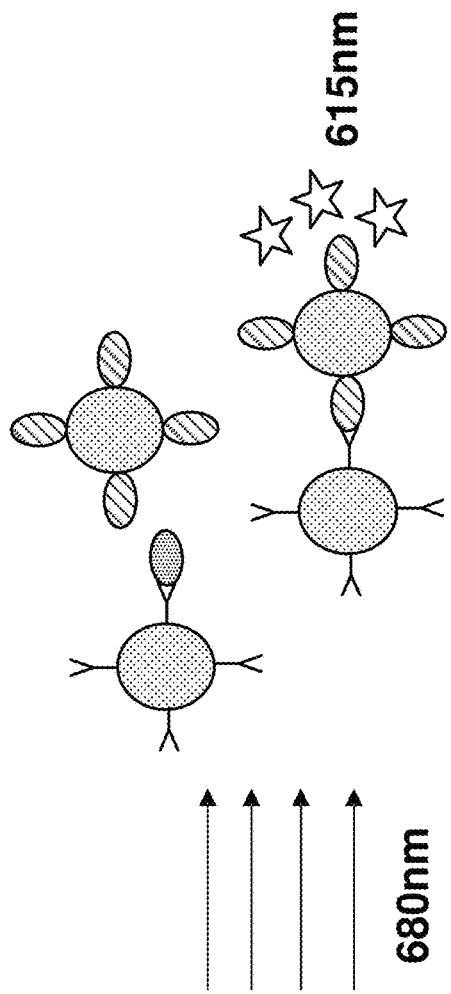

AMBIENT CONTAMINATION IN BREATH ANALYTE DETECTION AND MEASUREMENT

CROSS-REFERENCES TO RELATED APPLICATIONS

An Application Data Sheet is filed concurrently with this specification as part of the present application. Each application that the present application claims benefit of or priority to as identified in the concurrently filed Application Data Sheet is incorporated by reference herein in their entireties and for all purposes.

BACKGROUND

With legalization of marijuana expanding and the risk of marijuana-associated impaired driving increasing, it is anticipated by the present inventors that there will be an increased need for portable and accurate measurement systems, methods and devices for quantifying levels of cannabinoid compounds, such as tetrahydrocannabinol (THC), that are present in a person's breath, e.g., such as during a traffic stop for suspected driving-under-the-influence. THC detection poses significant challenges since the amounts of THC that may be present in an exhaled breath are quite minute-much more so than is the case with alcohol.

SUMMARY

Details of one or more implementations of the subject matter described in this specification are set forth in the accompanying drawings and the description below. Other features, aspects, and advantages will become apparent from the description, the drawings, and the claims.

Methods, systems, and apparatuses for evaluating an analyte level from a breath sample are disclosed. Furthermore, the presence of the analyte of interest in the environment (e.g., in ambient air) could influence measurements in breath. Accordingly, the present disclosure encompasses comparing analyte levels in a breath sample from a subject with analyte levels in an ambient air sample obtained in proximity to the subject. Such proximity can include spatial proximity (e.g., an ambient air sample obtained within a certain distance from the subject) and/or temporal proximity (e.g., an ambient air sample obtained within a certain period of time from obtaining the breath sample from the subject). In this way, the determined amount of analyte in the breath sample can be correlated with consumption of the analyte, passive inhalation of the analyte, and/or environmental exposure to the analyte.

In particular embodiments, the analyte is tetrahydrocannabinol (THC). In various embodiments, the disclosed methods include immunoassay-based detection systems and methods. Among the potential benefits of such methods and systems are enhanced sensitivity and device scalability. The disclosed methods and systems may be implemented in a variety of ways, as contemplated by this disclosure.

A breath sample generally includes aerosol droplets or particles, which in turn contain various lung proteins and surfactants. In particular, the analyte can be confined within droplets and surrounded by surfactant molecules, thereby making the analyte more difficult to access. Provided herein are breath collection modules, trapping structures, impaction ports, materials, and extraction solutions to trap droplets and then elute components of such droplets into a test fluid that can be further analyzed.

Within ambient air, particulate matter can be present, in which such matter can include dust, soot, smoke, smog particles, pollen, or other debris, such as particles arising from combustion or vaporization of various materials. In some instances, the analyte of interest can bind to such particulate matter in ambient air, which can be passively inhaled and then exhaled by the subject. The level of analyte in ambient air can be determined and then compared to levels of analyte in breath to assess the extent of ambient contamination.

For instance, if the analyte is THC, then comparing the level of THC in breath with that in ambient air can characterize the contribution of ambient THC levels in the environment to the THC level in breath, thereby providing a normalized level indicative of THC consumption or THC-associated impairment and not ambient THC contamination. Provided herein are methods, devices, and extraction solutions to capture particles in ambient air samples and then elute components of such particles into a control fluid, which can be further analyzed to assess the amount (a background level) of analyte present in ambient air.

THC detection in blood is a gold standard, but obtaining a blood sample is generally invasive. More minimally invasive samples can include urine, oral fluid, breath, and others. One advantage of breath is that breath THC levels correlate very closely with blood levels, whereas urine and oral fluid do not.

Thus, THC detection in human breath can be one way to determine if a suspected marijuana user is under the influence. Unlike with alcohol, which the body can purge in relatively short order, e.g., less than a day, THC compounds may be present in a person's body long after they are no longer under the influence of the THC. Breath-testing for THC in breath at the roadside, alone or in combination with alcohol, would be convenient, non-invasive, and leverages the wide acceptance of administering a breath test at the roadside, as is commonly employed for alcohol.

Among the features of the disclosure are systems and methods that may be implemented in devices that provide for convenient and reliable roadside detection and determination of THC recent use that may be correlated with impairment. The systems, methods, and contemplated devices may also be adaptable to combining testing for THC and alcohol (ethanol) impairment, and/or to the detection and evaluation of other airborne substances, including controlled substances, and breath-borne indicators of various disease states.

In particular embodiments, the analyte is THC. A reliably detectable picogram-level threshold may be correlated with a maximum baseline level of THC in breath associated with consumption of THC outside a window of THC-associated impairment and/or an average amount of THC in breath between 2 and 3 hours after inhalation for a range of users. The threshold may represent a baseline mean level of residual THC in breath associated with consumption of THC outside a window of THC-associated impairment across a broad demographic, for example from inhalation to between 2 and 3 hours after inhalation. An indication that the amount of THC captured from a breath sample exceeds the threshold may then be considered a positive test result for recent inhalation of THC that is independent of the frequency of the test subject's THC use. Such a method, then, may be adapted for breath-testing for THC, alone or in combination with alcohol, at the roadside.

THC, however, is much less prevalent in breath compared to alcohol, and is measured in the parts per trillion (picograms, pg) range in breath. According to various embodiments, the threshold referenced in the comparison may be less than 10 picogram/liter (pg/L) of breath, or from 2 to 5 pg/L of breath, or from 2 to 3 pg/L of breath, for example, about 2.4 pg/L of breath or, alternatively, about 1-2 pg/L. The threshold may vary depending upon the capture efficiency of the device or system with which the method is conducted.

A background level of THC in ambient air can also be established by assessing the amount of THC in an ambient air sample. Such an ambient air sample can be obtained in proximity to the subject and within a certain period of time as obtaining the breath sample from the subject. The background level can be influenced by various factors, including geographical location (e.g., proximity to population centers, freeways, etc.; effect of topography and/or air currents), time of day, weather (e.g., temperature, pressure, wind, the presence of inversion layers, etc.), and the like. This background can be very low (e.g., less than about 0.1 pg/L of ambient air) or high (e.g., about 1 pg/L or more, such as up to 5 pg/L). Thus, assessing the background level of THC in ambient air can provide further validation of a positive test result for recent THC use.

In various embodiments, in order achieve picogram sensitivity, the determining aspect of the method may involve an immunoassay. Suitable immunoassays are described herein and may include the use of capture agents (e.g., a THC antibody, a synthetic THC antigen, an enzyme-conjugated synthetic THC antigen, an enzyme-conjugated THC antibody, an enzyme-conjugated second antibody, and the like), detectable labels (e.g., a diazotized label, a substrate, an acceptor bead, a donor bead, an enzyme-conjugated synthetic THC antigen, an enzyme-conjugated THC antibody, an enzyme-conjugated second antibody, and the like), signal amplification reagents (e.g., tyramide), and a source to produce a detectable signal (e.g., a fluorescence signal), as described herein.

Any useful detection technique can be implemented with an immunoassay to determine an amount of the analyte. For instance, the immunoassay format can be used to bind to the desired analyte, and other detection schemes can be used to observe such binding. Non-limiting detection schemes can include tyramide signal amplification, proximity ligation, piezo-electric analysis, electrochemical impedance spectroscopy, nanopore-based analysis, mass spectrometry, Raman spectroscopy, infrared spectroscopy, or near-infrared spectroscopy, as described herein.

In various embodiments (e.g., in order to meet the evidentiary standards associated with roadside sobriety tests), an equal portion of the breath sample as drawn into the reaction channel may be drawn into an evidence channel on the test cartridge. In further embodiments, an equal portion of the ambient air sample as drawn into the reaction channel may be drawn into an evidence channel on the test cartridge.

In various embodiments, the test cartridge comprises a microfluidic or a minifluidic device. The test cartridge can include any useful fluidic structure, including those having a rigid material or a flexible material.

In various embodiments, data corresponding to one or more of the determining the amount of an analyte captured from the breath sample and/or the ambient air sample obtained from the subject, the comparing the determined amount of analyte from the breath sample to a threshold level for analyte in breath and/or the background level for analyte in ambient air, and the indicating whether or not the determined amount of analyte captured from the breath sample exceeds the threshold and/or the background levels, may be wirelessly transmitted to a remote location.

In various embodiments, two or more analytes (e.g., both THC and ethanol) are measured from the same breath sample and/or ambient air sample. In some embodiments, at least one of the analytes is a reference analyte.

Also disclosed herein are methods, devices, and systems to capture and analyze analytes using noninvasive point of care testing. Embodiments for implementation may include functional elements (or modules) including breath capture, detection method, and chemistry modules, including noninvasive point of care testing devices and systems, particularly portable (e.g., handheld) such modules, devices and systems. The sample capture and analysis (e.g., measurement, determination and/or result reporting) can all be conducted at the point of care, for example using portable, including handheld, devices and systems configured to capture and analyze the sample (e.g., the breath sample or the ambient air sample) and provide the measurement/result at or near the time and place of sample collection. In particular embodiments, any of the functional elements (or modules) may be configured to be conducted in the presence of an extraction solution (e.g., any described herein).

In one embodiment of this disclosure, a method includes capturing an exhaled breath sample from a subject at a location, such as a point of care for the subject, wherein the exhaled breath sample comprises aerosol droplets or particles, which are captured by impaction in a structure; capturing an ambient air sample at the location, wherein the ambient air sample comprises aerosol droplets or particles; and retaining the captured droplets in the same structure for analysis for an analyte therein, wherein the capturing and retaining for analysis are conducted at the location.

In some embodiments, the capturing of the aerosol droplets or particles by impaction involves capturing of the droplets or particles through a plurality of impaction ports that are fluidically connected in parallel. In other embodiments, capture of the aerosol droplets or particles can occur by way of filtration. In one instance, breath is flowed through a porous material having pores that are small enough to filter out droplets. In particular instances, the material can include pores to filter droplets, as well as properties that facilitate droplet impaction.

In some embodiments, the analysis for the analyte in the captured aerosol droplets or particles is conducted using no more than a very small fluid volume, for example on the order of less than 100 µL, e.g., no more than 10 to 20 µL. In some embodiments, this may be accomplished by integrating the impaction sites directly into a microfluidic structure (e.g., a microfluidic circuit or plate) configured for analysis of the collected sample, such that droplet traps allow the collected samples to be eluted and transported within the microfluidic structure using a very small fluid volume. In other embodiments, this may include use of an extraction solution to elute and transport the collected samples using a very small fluid volume. Capture of the analyte, in some instances, can also be conducted in the presence of the extraction solution. The collected sample can include a breath sample and/or an ambient air sample.

Disclosed embodiments may also achieve capture, analysis (e.g., measurement, determination and/or reporting) of an analyte in the captured aerosol droplets or particles at the point of care without any post-collection concentration operations.

This disclosure also relates to systems and apparatus for measuring an analyte, such as tetrahydrocannabinol (THC), another controlled substance, or another analyte, such as one associated with a physiological condition, from a breath sample and/or an ambient air sample in accordance with the methods herein described. In particular embodiments, the analyte within a breath sample is captured within aerosol drops, which in turn include lung surfactants. In another embodiment, the analyte within an ambient air sample is captured within particles, which in turn can include environmental particular matter. Such analytes can be collected, eluted, transported, and/or captured in the presence of an extraction solution (e.g., any described herein).

In particular embodiments, the analyte in a breath sample may be aerosolized in forcefully exhaled aerosol drops. In particular embodiments, the aerosol drops may be of a size range of about 3-5 µL, for example about 4.5 µL. In other embodiments, the aerosol drops may be of a size range of about 0.1-10 µm for a feature (e.g., a diameter, such as an average diameter).

In some embodiments, the threshold level may be less than 10 pg/L of breath.

In some embodiments, the aerosol drops may be captured by a device configured for impact and capture of aerosol drops forcefully exhaled into the device, as further described below. In particular embodiments, captured aerosol drops are eluted from the device by use of any extraction solution described herein.

In any embodiment herein, a material configured to capture liquid drops or particles is a substrate including one or more channels configured to facilitate droplet capture or particle capture through inertial impaction or filtration. It is to be understood that capture can occur in any useful manner, such as inertial impaction or filtration. Any discussion herein regarding capture, even if made in reference to just inertial impaction, can apply to inertial impaction, filtration, and/or other techniques.

In further embodiments, a method can include eluting the analyte from the material using an extraction solution to form the test fluid (for a breath sample) or the control fluid (for an ambient air sample). The method, in turn, can include delivering the test fluid and/or the control fluid through the one or more channels of the substrate. In other embodiments, said determining includes receiving the test fluid and/or the control fluid within a corresponding reaction channel configured for conducting an assay.

In any embodiment herein, the extraction solution includes an anionic detergent (e.g., any described herein, including a compound having a structure of formula (I)) and a buffering agent at a concentration to provide a pH from about 9.0 to about 9.5. In particular embodiments, said determining is conducted in the presence of the extraction solution (e.g., conducting an assay in the presence of the extraction solution, exposing the analyte to a detectable label in the presence of the extraction solution, and/or capturing the labeled complex with a capture agent in the presence of the extraction solution).

In any embodiment herein, the assay includes an immunoassay. Non-limiting assays can include a surface-based antibody-down immunoassay, a surface-based antigen-down immunoassay, a noncompetitive immunoassay, a heterogeneous competitive immunoassay, a homogeneous competitive immunoassay, or any other described herein.

In any embodiment herein, determining further includes: measuring a detectable signal indicative of a presence or an absence of the analyte after conducting the assay. Non-limiting detectable signals include a fluorescent signal, a chemiluminescent signal, an electroluminescent signal, a luminescent signal, a radiation signal, an electric signal (e.g., impedance, current, voltage, conductivity, etc.), an electrochemical signal, an optical signal, a piezoelectrical signal, a molecular ion signal, an infrared signal, a near infrared signal, a Raman signal, or a colorimetric signal. In particular embodiments, said measuring includes tyramide signal amplification, proximity ligation, piezo-electric analysis, electrochemical impedance spectroscopy, nanopore-based analysis, mass spectrometry, Raman spectroscopy, infrared spectroscopy, or near-infrared spectroscopy.

Details of one or more implementations of the subject matter described in this specification are set forth in the accompanying drawings and the description below. Other features, aspects, and advantages will become apparent from the description, the drawings, and the claims.

Definitions

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —O-Ak, wherein Ak is optionally substituted $C_{1-6}$ alkyl); (2) $C_{1-6}$ alkylsulfinyl (e.g., —S(O)-Ak, wherein Ak is optionally substituted $C_{1-6}$ alkyl); (3) $C_{1-6}$ alkylsulfonyl (e.g., —SO$_2$-Ak, wherein Ak is optionally substituted $C_{1-6}$ alkyl); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —O-L-Ar, wherein L is a bivalent form of optionally substituted alkyl and Ar is optionally substituted aryl); (7) aryloyl (e.g., —C(O)—Ar, wherein Ar is optionally substituted aryl); (8) azido (e.g., —N$_3$); (9) cyano (e.g., —CN); (10) carboxyaldehyde (e.g., —C(O)H); (11) $C_{3-8}$ cycloalkyl (e.g., a monovalent saturated or unsaturated non-aromatic cyclic $C_{3-8}$ hydrocarbon group); (12) halo (e.g., F, Cl, Br, or I); (13) heterocyclyl (e.g., a 5-, 6- or 7-membered ring, unless otherwise specified, containing one, two, three, or four non-carbon heteroatoms, such as nitrogen, oxygen, phosphorous, sulfur, or halo); (14) heterocyclyloxy (e.g., —O-Het, wherein Het is heterocyclyl, as described herein); (15) heterocyclyloyl (e.g., —C(O)—Het, wherein Het is heterocyclyl, as described herein); (16) hydroxyl (e.g., —OH); (17) N-protected amino; (18) nitro (e.g., —NO$_2$); (19) oxo (e.g., =O); (20) $C_{3-8}$ spirocyclyl (e.g., an alkylene or heteroalkylene diradical, both ends of which are bonded to the same carbon atom of the parent group); (21) $C_{1-6}$ thioalkoxy (e.g., —S-Ak, wherein Ak is optionally substituted $C_{1-6}$ alkyl); (22) thiol (e.g., —SH); (23) —CO$_2$R$^A$, where R$^A$ is selected from the group consisting of (a) hydrogen, (b) $C_{1-6}$ alkyl, (c) $C_{4-18}$ aryl, and (d) ($C_{4-18}$ aryl) $C_{1-6}$ alkyl (e.g., -L-Ar, wherein L is a bivalent form of optionally substituted alkyl group and Ar is optionally substituted aryl); (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) ($C_{4-18}$ aryl) $C_{1-6}$ alkyl (e.g., -L-Ar, wherein L is a bivalent form of optionally substituted alkyl group and Ar is optionally substituted aryl); (25) —SO$_2$R$^D$, where R$^D$ is selected from the group consisting of (a) hydroxyl, (b) $C_{1-6}$ alkyl, (c) $C_{4-18}$ aryl, and (d) ($C_{4-18}$ aryl) $C_{1-6}$ alkyl (e.g., -L-Ar, wherein L is a bivalent form of optionally substituted alkyl group and Ar is optionally substituted aryl); (26) —SO$_2$NR$^E$R$^F$, where each of R$^E$ and R$^F$ is, independently, selected from the group consisting of (a) hydrogen, (b) C$_{1-6}$ alkyl, (c) C$_{4-18}$ aryl, and (d) (C$_{4-18}$ aryl) C$_{1-6}$ alkyl (e.g., -L-Ar, wherein L is a bivalent form of optionally substituted alkyl group and Ar is optionally substituted aryl); and (27) —NR$^G$R$^H$, where each of R$^G$ and R$^H$ is, independently, selected from the group consisting of (a) hydrogen, (b) an N-protecting group, (c) C$_{1-6}$ alkyl, (d) C$_{2-6}$ alkenyl (e.g., optionally substituted alkyl having one or more double bonds), (e) C$_{2-6}$ alkynyl (e.g., optionally substituted alkyl having one or more triple bonds), (f) C$_{4-18}$ aryl, (g) (C$_{4-18}$ aryl) C$_{1-6}$ alkyl (e.g., L-Ar, wherein L is a bivalent form of optionally substituted alkyl group and Ar is optionally substituted aryl), (h) C$_{3-8}$ cycloalkyl, and (i) (C$_{3-8}$ cycloalkyl) C$_{1-6}$ alkyl (e.g., -L-Cy, wherein L is a bivalent form of optionally substituted alkyl group and Cy is optionally substituted cycloalkyl, as described herein), wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a C$_{1-3}$, C$_{1-6}$, C$_{1-12}$, C$_{1-16}$, C$_{1-18}$, C$_{1-20}$, or C$_{1-24}$ alkyl group.

By "alkylene" is meant a multivalent (e.g., bivalent) form of an alkyl group, as described herein. Exemplary alkylene groups include methylene, ethylene, propylene, butylene, etc. In some embodiments, the alkylene group is a C$_{1-3}$, C$_{1-6}$, C$_{1-12}$, C$_{1-16}$, C$_{1-18}$, C$_{1-20}$, C$_{1-24}$, C$_{2-3}$, C$_{2-6}$, C$_{2-12}$, C$_{2-16}$, C$_{2-18}$, C$_{2-20}$, or C$_{2-24}$ alkylene group. The alkylene group can be branched or unbranched. The alkylene group can also be substituted or unsubstituted. For example, the alkylene group can be substituted with one or more substitution groups, as described herein for alkyl.

By "amino" is meant —NR$^{N1}$R$^{N2}$, where each of R$^{N1}$ and R$^{N2}$ is, independently, H, optionally substituted alkyl, or optionally substituted aryl, or R$^{N1}$ and R$^{N2}$, taken together with the nitrogen atom to which each are attached, form a heterocyclyl group, as defined herein. Non-limiting heterocyclyl groups for an amine (a heterocyclic amine) can include, e.g., azetidinyl, pyrrolidinyl, pyrrolinyl, pyrrolyl, pyrazolidinyl, imidazolidinyl, piperidinyl, piperazinyl, pyridinyl, pyridazinyl, pyrimidinyl, pyrazinyl, and the like. Optionally, the heterocyclic amine can include one or more cationic amino groups, such as a protonated nitrogen atom N$^+$, such as in piperidinium, piperazinium, pyridinium, pyrazinium, and the like. The amino can be unsubstituted or substituted, such as with one or more substitutions described herein for alkyl.

By "aromatic" is meant a cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized n-electron system. Typically, the number of out of plane n-electrons corresponds to the Huckel rule (4n+2). The point of attachment to the parent structure typically is through an aromatic portion of the condensed ring system. Such an aromatic can be unsubstituted or substituted with one or more groups, such as groups described herein for an alkyl group. Yet other substitution groups can include aliphatic, haloaliphatic, halo, nitrate, cyano, sulfonate, sulfonyl, or others.

By "carboxyl" is meant a —CO$_2$H group.

By "heteroalkyl" is meant an alkyl group, as defined herein, containing one, two, three, or four non-carbon heteroatoms (e.g., independently selected from the group consisting of nitrogen, oxygen, phosphorous, sulfur, selenium, or halo).

By "heteroalkylene" is meant a multivalent (e.g., a bivalent) form of an alkylene group, as defined herein, containing one, two, three, or four non-carbon heteroatoms (e.g., independently selected from the group consisting of nitrogen, oxygen, phosphorous, sulfur, selenium, or halo). The heteroalkylene group can be substituted or unsubstituted. For example, the heteroalkylene group can be substituted with one or more substitution groups, as described herein for alkyl.

By "heterocyclyl" is meant a 3-, 4-, 5-, 6- or 7-membered ring (e.g., a 5-, 6- or 7-membered ring), unless otherwise specified, containing one, two, three, or four non-carbon heteroatoms (e.g., independently selected from the group consisting of nitrogen, oxygen, phosphorous, sulfur, selenium, or halo). The 3-membered ring has zero to one double bonds, the 4- and 5-membered ring has zero to two double bonds, and the 6- and 7-membered rings have zero to three double bonds. The heterocyclyl can be unsubstituted or substituted, such as with one or more substitutions described herein for alkyl.

As used herein, "isomer" is meant a molecule having the same molecular formula as the reference molecule. Exemplary isomers include stereoisomers, diastereomers, enantiomers, geometric isomers, tautomers, as well as mixtures thereof. An isomer can include a stereoisomer and/or an optical isomer, as well as mixtures of isomers (including racemic mixtures) or enantiomerically enriched mixtures of disclosed compounds.

As used herein, "salt" is meant an ionic form of a compound or structure (e.g., any formulas, compounds, or compositions described herein), which includes a cation or anion compound to form an electrically neutral compound or structure. Salts are well known in the art. For example, non-toxic salts are described in Berge S M et al., "Pharmaceutical salts," *J. Pharm. Sci.* 1977 January; 66(1):1-19; and in "Handbook of Pharmaceutical Salts: Properties, Selection, and Use," Wiley-VCH, April 2011 (2nd rev. ed., eds. P. H. Stahl and C. G. Wermuth. The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, gluconate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine. Yet other salts include ammonium, sulfonium, sulfoxonium, phosphonium, iminium, imidazolium, benzimidazolium, amidinium, guanidinium, phosphazinium, phosphazenium, pyridinium, etc., as well as other cationic groups described herein (e.g., optionally substituted isoxazolium, optionally substituted oxazolium, optionally substituted thiazolium, optionally substituted pyrrolium, optionally substituted furanium, optionally substituted thiophenium, optionally substituted imidazolium, optionally substituted pyrazolium, optionally substituted isothiazolium, optionally substituted triazolium, optionally substituted tetrazolium, optionally substituted furazanium, optionally substituted pyridinium, optionally substituted pyrimidinium, optionally substituted pyrazinium, optionally substituted triazinium, optionally substituted tetrazinium, optionally substituted pyridazinium, optionally substituted oxazinium, optionally substituted pyrrolidinium, optionally substituted pyrazolidinium, optionally substituted imidazolinium, optionally substituted isoxazolidinium, optionally substituted oxazolidinium, optionally substituted piperazinium, optionally substituted piperidinium, optionally substituted morpholinium, optionally substituted azepanium, optionally substituted azepinium, optionally substituted indolium, optionally substituted isoindolium, optionally substituted indolizinium, optionally substituted indazolium, optionally substituted benzimidazolium, optionally substituted isoquinolinum, optionally substituted quinolizinium, optionally substituted dehydroquinolizinium, optionally substituted quinolinium, optionally substituted isoindolinium, optionally substituted benzimidazolinium, and optionally substituted purinium).

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIGS. 5A-D depict a surface-based antibody-down immunoassay.

FIGS. 6A-C depict a surface-based antibody-down, competitive immunoassay.

FIGS. 8A-F depict a surface-based antigen-down, heterogeneous, competitive two-antibody immunoassay.

FIGS. 9A-C depict a homogeneous competitive immunoassay.

FIG. 13' depicts a supplemental view showing the mouthpiece of the cartridge of FIG. 13 in a twisted, locked configuration.

DETAILED DESCRIPTION

Figure 1:
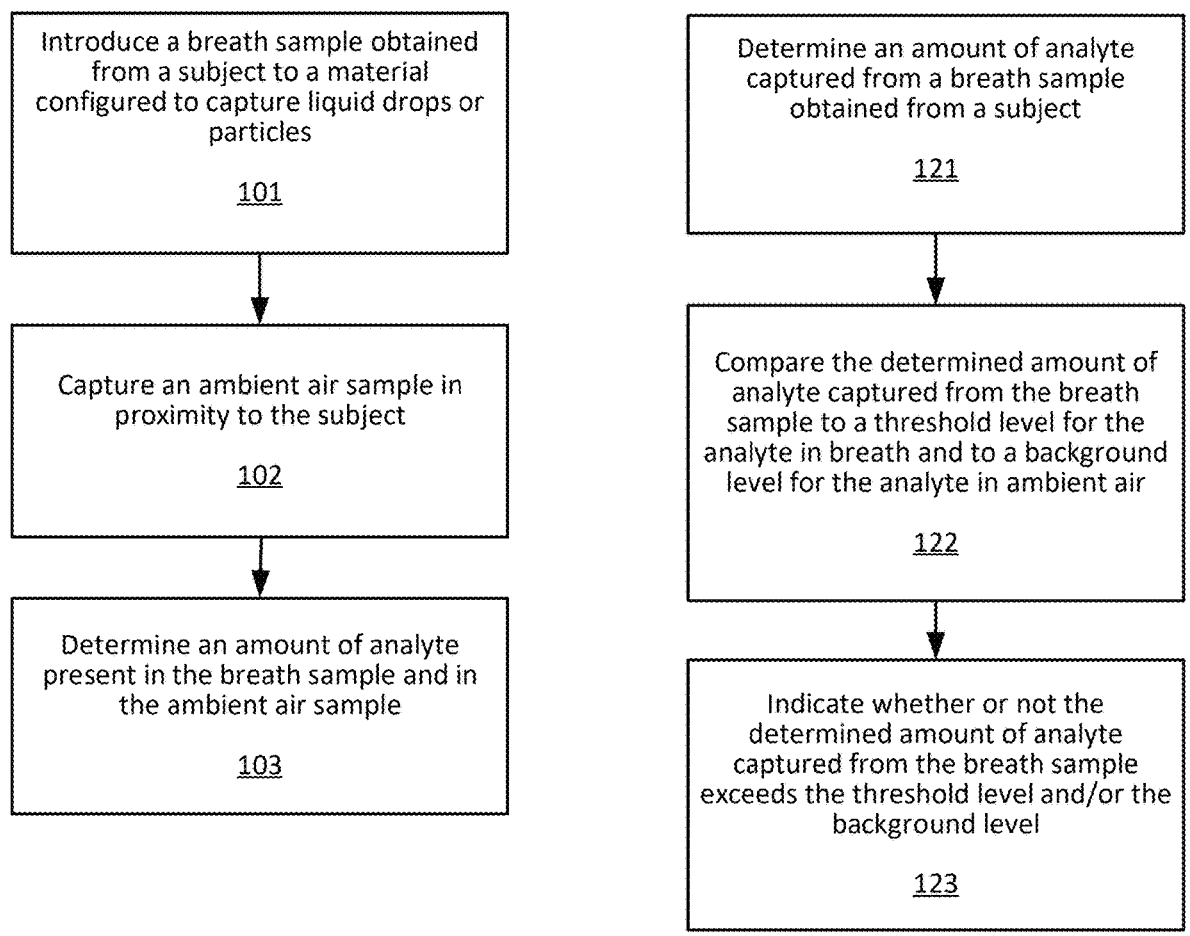
FIG. 1A-1B depict (A) a non-limiting process flow chart for method in accordance with the present disclosure and (B) another non-limiting process flow chart.

Importantly, the concepts discussed herein are not limited to any single aspect or implementation discussed herein, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

Methods, systems and apparatus for measuring an analyte level from a breath sample and an ambient air sample are disclosed. In some embodiments, the analyte is tetrahydrocannabinol (THC). In various embodiments, the disclosed methods include immunoassay-based detection systems and methods. Among the potential benefits of such methods and systems are enhanced sensitivity and device scalability. The disclosed methods and systems may be implemented in variety of ways as contemplated by this disclosure. Among the features of the disclosure are systems and methods that may be implemented in devices that provide for convenient and reliable roadside detection and determination of THC recent use that may be correlated with impairment. The systems, methods and contemplated devices may also be adaptable to combining testing for THC and alcohol (ethanol) impairment, and/or to the detection of other airborne substances, including controlled substances, and breath-borne indicators of various disease states.

In *Marijuana-impaired Driving*: A Report to Congress dated July 2017, the National Highway Traffic Safety Administration (NHTSA) found that impairment is observed for two to three hours after smoking marijuana. Data collected and processed by the inventors has shown that a reliably detectable picogram-level threshold may be correlated with a maximum baseline level of THC in breath for chronic or frequent THC smokers and/or an average amount of THC in breath between 2 and 3 hours after inhalation for a range of users. More generally, it appears that the threshold may represent a baseline mean level of residual THC in breath associated with consumption of THC outside a window of THC-associated impairment across a broad demographic, for example from inhalation to between 2 and 3 hours after inhalation. An indication that the amount of THC captured from a breath sample exceeds the threshold may then be considered a positive test result for recent inhalation of THC that is therefore independent of the frequency of the test subject's THC use. Such a method, then, may be adapted for breath-testing for THC at the roadside. The method herein, while described for THC in some instances, can be adapted to determine an amount of any useful analyte. For instance, the analyte can be one that would benefit from being treated with an extraction solution, as described herein.

By understanding that THC can be present within ambient air, the detected amount of THC in breath may include some combination of an environmental, background level of THC with an amount indicative of the subject's THC use. Thus, the methods herein, as well as apparatuses and systems configured to conduct such methods, can include using a determined amount of the analyte in ambient air.

Referring to FIG. 1A, a general flow chart for a method in accordance with the present disclosure is depicted. According to various embodiments, the method for isolating an analyte from a breath sample obtained from a subject involves introducing the breath sample obtained from a subject to a material configured to capture liquid drops or particles (101); capturing an ambient air sample in proximity to the subject (102); and determining an amount of the analyte present in the breath sample and in the ambient air sample (103).

In some embodiments, the determining operation can include eluting the analyte from the material by using an extraction solution, thereby providing a test fluid indicative of the amount of analyte present in the breath sample. In particular embodiments, the determining operation is performed without further diluting the test fluid. Rather, the test fluid obtained during elution is directly used to perform the assay to determine the amount of the analyte. By employing the extraction solution as the assay buffer, further dilution of the analyte can be avoided, and sensitivity of the assay can be improved. Thus, in some embodiments, the determining operation includes conducting an assay in the presence of the extraction solution. Any assay described herein can be performed by using the extraction solution as the assay buffer.

In other embodiments, the method can further including capturing particles within the ambient air sample in a material and then eluting the analyte from the material by using an extraction solution, thereby providing a control fluid indicative of the amount of analyte present in the ambient air sample. Determining the amount of analyte in the control fluid can also be optionally performed without further diluting the control fluid.

Referring to FIG. 1B, a general flow chart for another method in accordance with the present disclosure is depicted. In addition to methods of isolating an analyte, the present disclose also encompasses methods for evaluating an analyte level in a breath sample.

According to various embodiments, the method involves determining an amount of an analyte captured from a breath sample obtained from a subject (121); comparing the determined amount of analyte captured from the breath sample to a threshold level for the analyte in breath and to a background level for the analyte in ambient air (122); and indicating whether or not the determined amount of analyte captured from the breath sample exceeds the threshold level and/or the background level (123). In one embodiment of this disclosure, a method includes capturing an exhaled breath sample from a subject in a point of care testing context.

Figure 2:
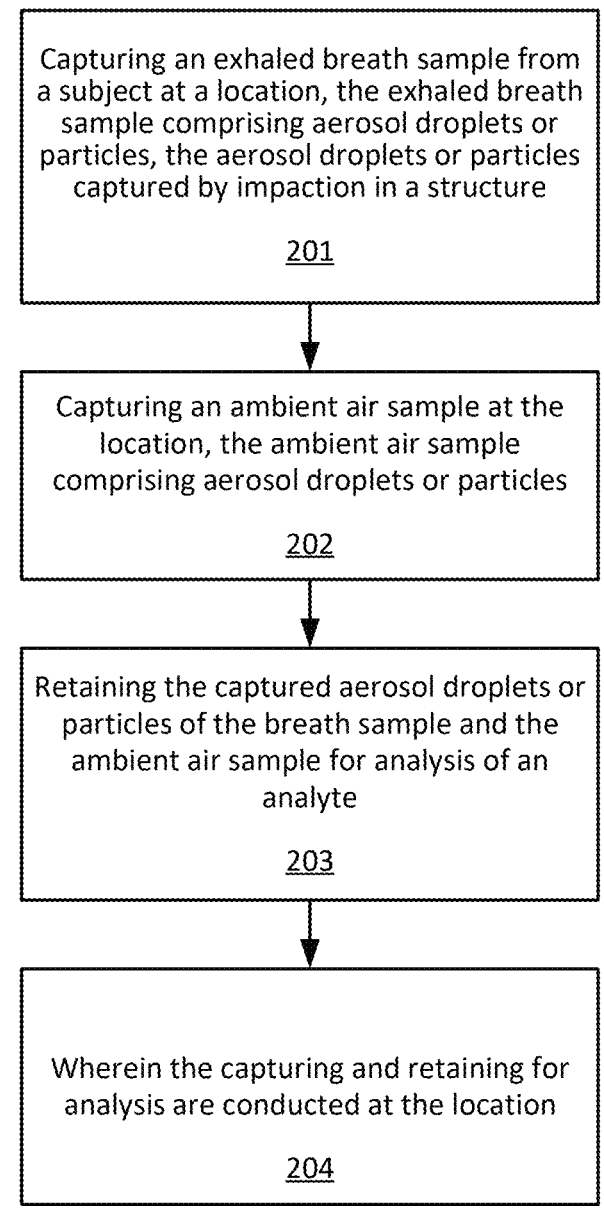
FIG. 2 depicts a general flow chart for a method in accordance with an aspect of the present disclosure.

The present disclosure also encompasses point of care methods, as well as apparatuses and systems for such point of care use. Referring to FIG. 2, a general flow chart for a method in accordance with this aspect of the present disclosure is depicted.

According to various embodiments, the method involves capturing an exhaled breath sample from a subject at a location, such as a point of care for the subject, wherein the exhaled breath sample comprises aerosol droplets or particles that are captured by impaction in a structure (201); capturing an ambient air sample at the location, such as a point of care for the subject, wherein the ambient air sample comprises aerosol droplets or particles (202); retaining the captured droplets or particles in a structure (e.g., a handheld unit, cartridge, fluidic structure, or microfluidic plate) for analysis for an analyte therein (203); and wherein the capturing and retaining for analysis are conducted at the location (204). The retaining operation includes retaining the captured droplets or particles for the breath sample and for the ambient air sample in a separate manner, thereby not mixing these two samples. In one instance, the droplets or particles for the breath sample are captured in a first structure at a first region in a device; and droplets or particles for the ambient air sample are captured in a second structure at a second region in the device, in which the first and second regions are located in different positions within the device.

Point of care methods can further include measuring an amount of the target analyte and a reference analyte (or biomarker) in the breath sample or in the captured aerosol droplets, the reference analyte known to exist at a stable concentration in the subject, and the determining involves a comparison of the target analyte measurement and the reference analyte measurement. As further described herein, this concept of using a reference analyte (or normalizing measurand, NM) can be used to facilitate quantitative measurement of analytes in captured breath samples. Examples of a NM include: sodium ion, potassium ion, chloride ion, total protein, albumin, total ionic strength, conductivity, pH, etc.

Thus, in some embodiments, the present disclosure also relates to use of an ambient analyte measurement (e.g., of THC in ambient air) and a reference analyte measurement (e.g., of an NM in a breath sample) to assist in accurately measuring and calibrating a level of the desired analyte in breath.

Figure 3:
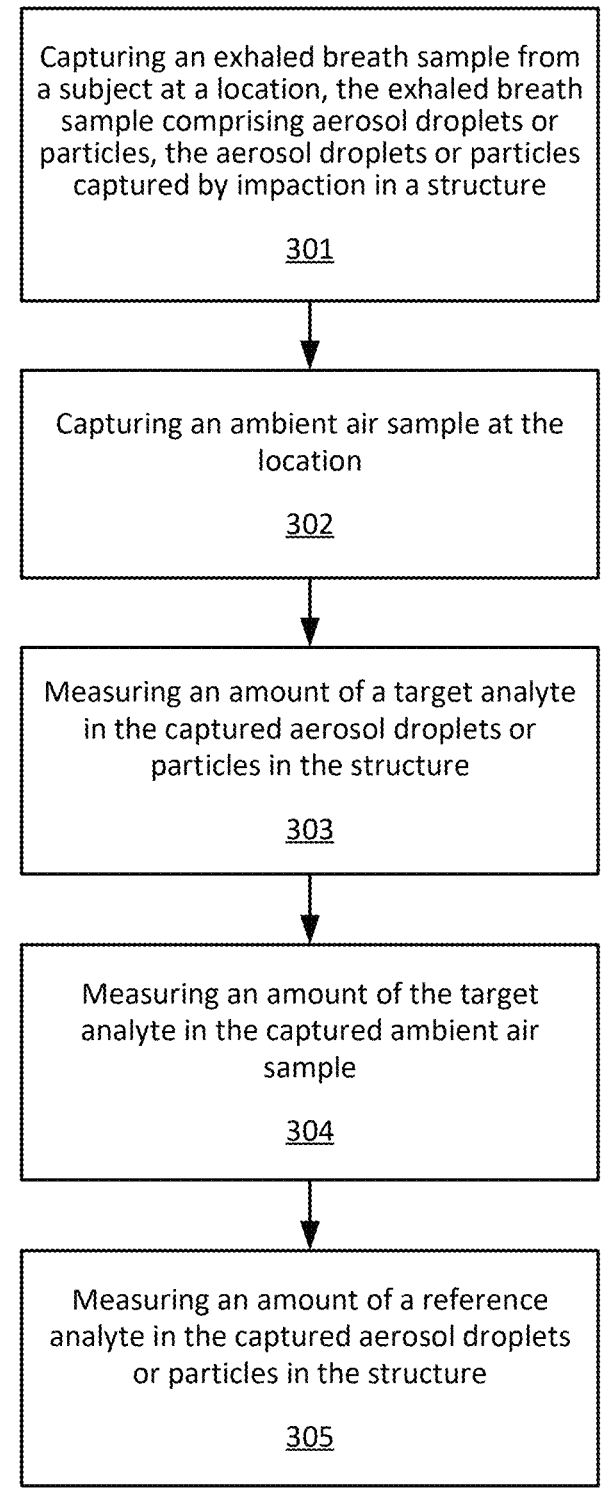
FIG. 3 depicts a general flow chart for a method in accordance with another aspect of the present disclosure.

Referring to FIG. 3, a general flow chart for a method in accordance with this aspect of the present disclosure is depicted. According to various embodiments, the method involves capturing an exhaled breath sample from a subject at a location, such that the exhaled breath sample comprises aerosol droplets or particles, which in turn are captured by impaction in a structure (301); capturing an ambient air sample at the location (302); measuring an amount of a target analyte in the captured aerosol droplets or particles in the structure (303); measuring an amount of the target analyte in the captured ambient air sample (304); and measuring an amount of a reference analyte in the captured aerosol droplets or particles in the structure (305).

In some embodiments, a concentration of the analyte in the exhaled breath sample is determined by comparing the measured amounts of reference analyte levels. In other embodiments, the determination operation further includes comparing the measured amounts of background analyte levels in ambient air.

In some embodiments measurement, the sample capture (e.g., of the breath sample and the ambient air sample), and determination can all be conducted at a single location, for example the point of care of the subject, for example using portable (e.g., handheld) devices and systems configured to capture and analyze the sample and provide the measurement/result at or near the time and place of sample collection from the subject—the point of care. And in some embodiments of this aspect, the concentration of the analyte may indicate a physiological condition of the subject.

Non-limiting analytes include THC, as well as other markers, such as cannabinol (CBN), cannabidiol (CBD), carboxy THC or 11-nor-9-carboxy-Δ9-tetrahydrocannabinol (THC-COOH), 11-hydroxy-$\Delta^9$-tetrahydrocannabinol (11-hydroxy THC), 9-carboxy THC or $\Delta^9$-tetrahydrocannabinolic acid (THC-9-COOH), tetrahydrocannabinolic acid (THCA, THC-2-COOH), and similar compounds, as well as isomers thereof.

Figure 4:
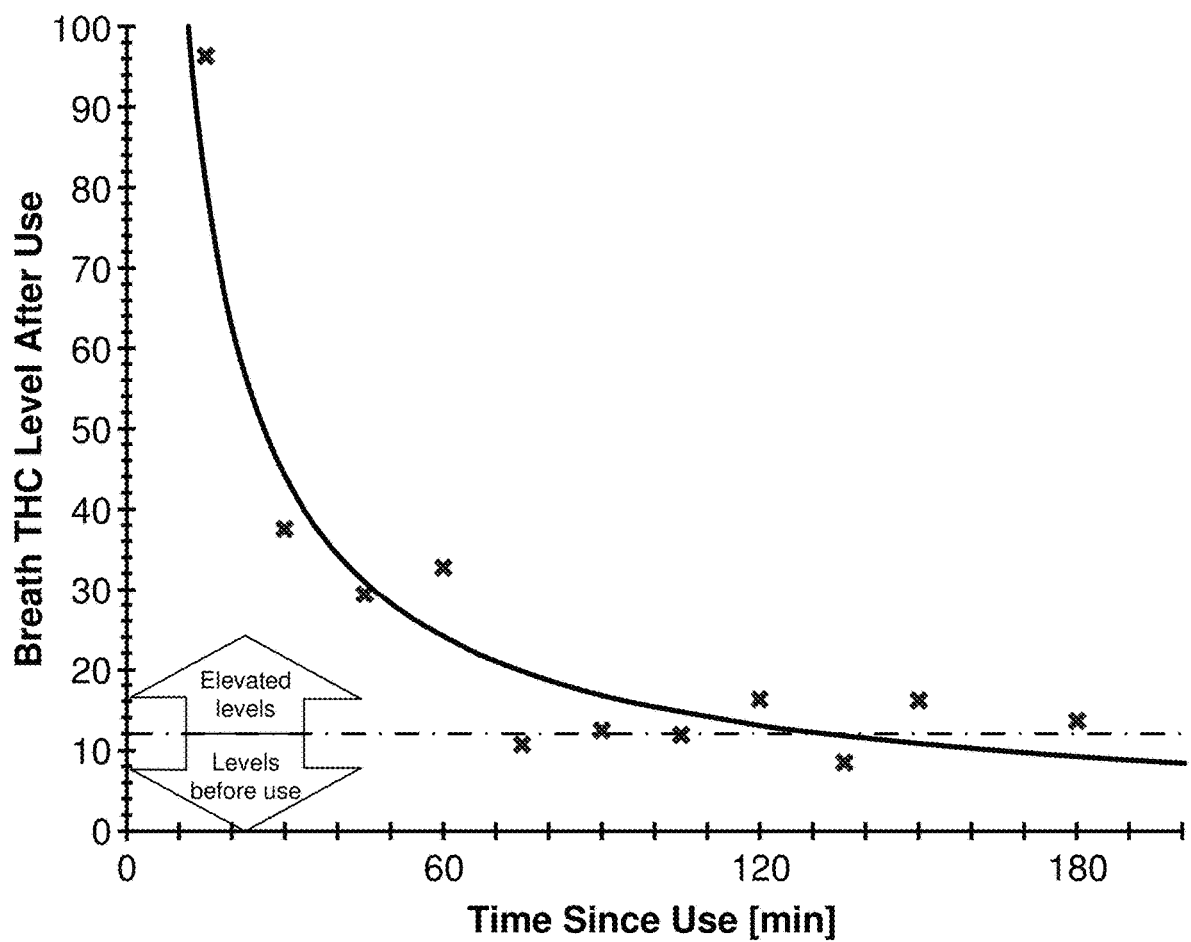
FIG. 4 depicts a plot showing breath THC level vs. time since use.

FIG. 4 depicts a plot showing breath THC level in picograms (pg) per breath (5 L) vs. time in minutes (min) since use in chronic or frequent THC smokers. From the plot, it can be seen that THC level in breath drops substantially in the first hour, and after 2 hours it drops below the maximum baseline threshold for chronic users. Testing has determined a maximum baseline THC level in breath for chronic users to be in the picogram per liter of breath range. Based on data obtained through testing, it appears that the threshold may represent a baseline mean level of residual THC in breath associated with consumption of THC across a broad demographic, regardless of use frequency, outside a window from inhalation to between 2 and 3 hours after inhalation, which has been associated with THC impairment. The threshold referenced in the comparison of the disclosed method may be less than 10 picogram/liter (pg/L) of breath, or from 2 to 5 pg/L of breath, or from 2 to 3 pg/L of breath, for example, about 2.4 pg/L of breath. The maximum baseline 12 pg/5 L (2.4 pg/L) breath is superimposed on the plot. The threshold may vary depending upon the capture efficiency of the device or system with which the method is conducted, and can be tuned in practice.

The principles of operation of the methods, systems, and apparatus described herein, while primarily developed and described with reference to inhalation of THC via marijuana smoking, are also expected to be applicable to ingestion of THC. While timeframes and biochemistry are different for edibles, the same thresholds correlated with THC breath concentration in breath are contemplated to be applicable in such contexts as well. Edibles generally contain a form of THC that is not psychoactive when ingested, but is subsequently metabolized to a psychoactive form. Antibodies for THC, or other THC binders as described herein, also bind to the THC metabolite rendering the methods described herein effective for measuring THC breath associated with edibles and comparing to a breath THC concentration threshold that has been associated with impairment.

It should also be understood that breath-testing for THC at the roadside may be combined with breath-testing for alcohol where another portion of the breath sample is tested for blood alcohol content (BAC) according to any suitable BAC analysis, such as are well-known in the art, as further discussed below.

In various embodiments, the method may include obtaining and processing the breath sample and the ambient air sample from the subject in manner suitable to conduct measurements in the picogram range in a roadside sobriety testing context, in particular using a device having a handheld form factor for obtaining the breath sample and the ambient air sample in a prescribed period of time and conducting an analysis on-site. Such a method may involve drawing a portion of the breath sample exhaled by the subject into a fluidic circuit or a reaction channel in a test cartridge with negative pressure, as well as drawing a portion of the ambient air sample (obtained in proximity to the subject) into a reaction channel in a test cartridge with negative pressure. So that sufficient analyte can be captured from a breath sample and/or the ambient air sample for use in a roadside sobriety testing context, the reaction channel or fluidic circuit may be configured to have a particular hydraulic diameter and length and/or shape and/or volume for to enhance capture efficiency.

In some embodiments, a fluidic circuit can be configured to include reservoirs, passages, reaction channels, etc. having boundaries (e.g., defined by permanent, temporary, or dynamic seals) to sufficiently capture and analyze samples (e.g., breath samples and/or ambient samples). The fluidic circuit, in some instance, can include a flexible material to provide a flexible fluidic circuit.

In use, For instance, the working volumes of such collapsible fluidic structures can be provided on-demand when pressurized fluid is introduced into such structures. In effect, the entire fluidic circuit may selectively transition between a "flat" state in which they have low, and in many cases, zero volume, and a "pressurized" state in which they have non-zero volumes. This avoids the need to displace a prior fluid, e.g., air, that was contained within such a fluidic structure prior to introduction of the sample of interest, thereby reducing the amount of fluids needed and/or reducing the likelihood of air bubbles being present in the fluid of interest. Additional details for fluidic circuits, especially pertaining to flexible fluidic structures, are described herein (see, e.g., FIGS. 15-21 and associated text).

In another embodiment, a reaction channel is employed. One way to configure the reaction channel, e.g., to facilitate analyte capture and analysis, is according to the following parameters: For a minimum channel volume of 15 μL, the hydraulic diameter (d) may range from 0.1-1 mm, and the channel length may range from 15 $\mu L/(d^2)$ to 45 $\mu L/(d^2)$ (assuming d in mm). In specific implementations, the reaction channel may have a hydraulic diameter of less than 1 mm and a length of at least 15 mm, and at least 0.5 μL of the sample (e.g., a breath sample and/or the ambient air sample) may be flowed through the reaction channel in no more than 90 s. In some embodiments, the reaction channel may have a hydraulic diameter of less than 0.8 mm and a length of at least 40 mm, for example a hydraulic diameter of about 0.7 mm and a length of about 57 mm, and at least 0.7 μL of the breath sample and/or the ambient air sample may be flowed through the reaction channel in about 60 s. Such reaction channels can be provided in any useful device, such as a microfluidic device, a minifluidic device, a flexible fluidic structure, and others described herein.

The preceding discussion of channel configuration relates to straight channels. But it should also be understood that the shape of a channel may also be manipulated to enhance capture efficiency. Other channel geometries, including hydraulic diameters, lengths and shapes may be desired depending on a particular capture target(s). The size, shape and form of the molecule or particle, etc. to be captured is generally a significant factor in configuring the channel to enhance capture efficiency. In general, larger targets would be better captured in channels that are not straight, such as zigzag, serpentine, curved, spiral, etc.-shaped channels. It should be understood that the channel geometry can be designed to improve capture efficiency, and can change depending upon the capture target(s).

Also a device can have multiple channels with same or different geometry configured to enhance the capture of different analytes or different forms of the same analyte (e.g., molecular vs. aerosol analyte), or one or more other analytes. In one example, a test for a plurality of different disease conditions from a single breath sample is contemplated. A device for implementing such a test might have a plurality of channels configured and/or designed for capture of a plurality of different breath-borne substances, which could then be processed in a manner as described herein. Furthermore, the device can have multiple channels configured for parallel processing of samples (e.g., parallel capture or assaying of different analytes in the same sample, parallel capture or assaying of the same analyte in different samples, parallel assaying and storing of aliquots of the same sample, etc.).

The samples herein (e.g., a breath sample and an ambient air sample) can be captured, and then captured components should then be released to determine the amount of analyte present within the sample. In particular, disclosed herein are extraction solutions configured to elute or extract an analyte obtained from a breath sample and/or an ambient air sample. Whereas a breath sample generally includes droplets containing various lung proteins and surfactants, an ambient air sample can include particulate matter. In particular, the analyte can be confined within droplets or trapped on particulate matter, thereby making the analyte more difficult to access.

Obtaining such analytes can include physical trapping of aerosol droplets or particles, followed by extracting analytes from the droplets or particles. Described herein are trapping structures that can trap such droplets, as well as extraction solutions that can extract and solubilize the analyte from the structure. Without wishing to be limited by mechanism, the extraction solution includes one or more detergents to break down or process captured aerosol droplets or particles, thereby releasing the desired analyte into solution. Furthermore, the pH of the extraction solution can be modified to facilitate solubility of the analyte within the solution. For instance, the pH can be optimized to be near the pKa of functional groups that will provide a charged species, thereby increasing solubility of the analyte within an aqueous solution.

In one non-limiting instance, the analyte is THC; and the extraction solution includes a detergent that releases THC from aerosol droplets or particles. The extraction solution can also possess a pH of about 9 to enhance solubility of THC in the solution. Non-limiting detergents include an anionic detergent, such as a bile acid, a bile salt, or a derivative thereof, as well as other detergents described herein.

In some embodiments, the extraction solution allows for a minimal working volume, thereby reducing the risk of further diluting the analyte in the systems, apparatuses, and devices described herein. Furthermore, detection (e.g., by use of an immunoassay) can be performed in the presence of the extraction solution, thus reducing the number of separating and/or rinsing steps that can further dilute the sample.

In use, the extraction solution can facilitate the isolation of the desired analyte from the captured breath sample or the captured ambient air sample. For instance, the extraction solution can be optimized to separate the analyte from surfactant molecules that are present in the breath sample, thereby releasing the analyte to allow for further measurements. In another instance, the extraction solution can be optimized to separate the analyte from the surface of particular matter that are present in the ambient air sample, thereby releasing the analyte.

Furthermore, if a droplet trap is used, then the extraction solution must also effectively elute the adsorbed analyte from the material forming the trap. Finally, to allow for a sufficient amount of analyte that can be detected, the solution must effectively solubilize the analyte.

One non-limiting extraction solution includes: (i) a detergent at a concentration of about 0.1 to about 1% by weight (e.g., about 0.1 (w/w) % to about 1 (w/w) %); and (ii) a buffering agent at a concentration to provide a pH from about 8-10 (e.g., about 9.0-9.5). In one embodiments, the same formulation of the extraction solution is employed to process both the breath sample and the ambient air sample. In further embodiments, the same extraction solution is employed with an immunoassay without further diluting the eluted breath sample or the eluted ambient air sample.

In some embodiments, the detergent includes a bile acid, a bile salt, or a derivative thereof, as well as any described herein. In particular embodiments, the detergent includes deoxycholic acid, cholic acid, or a salt thereof. In other embodiments, the detergent includes a structure of formula (I):

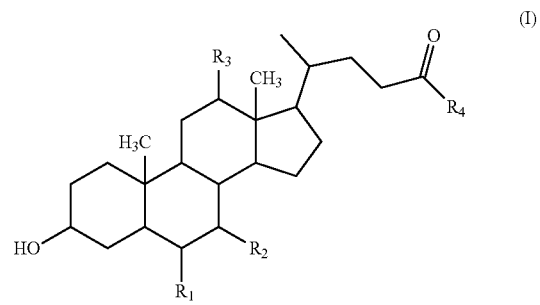

or a salt thereof and/or an isomer thereof, wherein: each of $R_1$, $R_2$, and $R_3$ is, independently, H, hydroxyl, or optionally substituted alkyl; and $R_4$ is H, hydroxyl, optionally substituted alkyl, optionally substituted heteroalkyl, optionally substituted amino, or optionally substituted heterocyclyl. In other embodiments (e.g., for formula (I) or a salt thereof and/or an isomer thereof), $R_4$ includes an anionic moiety. By anionic moiety is meant a monoatomic or polyatomic species having one or more elementary charges of the electron.

In some embodiments, the buffering agent includes a buffering agent, e.g., a zwitterionic buffering agent. Non-limiting zwitterionic agents include 3-(cyclohexylamino)-2-hydroxy-1-propanesulfonic acid (CAPSO), 3-(cyclohexylamino)-1-propanesulfonic acid (CAPS), 3-([1,1-dimethyl- 2-hydroxyethyl]amino)-2-hydroxypropane sulfonic acid (AMPSO), a free acid form thereof, or a salt form thereof, as well as any others described herein.

The extraction solution can include one or more other additives. Non-limiting additives can include a non-ionic detergent, an anionic detergent, a cationic detergent, a zwitterionic detergent, an ionic detergent, a buffering agent, a solvent (e.g., an aqueous solvent), a phospholipase, a chelating agent, an antioxidant, a salt, a protein, an amino acid, an enzyme, a denaturant, a protease inhibitor, a reducing agent, a sugar, a polyol, a betaine, and the like, as well as combinations thereof. Further extraction solutions, as well as methods and apparatuses using such solution, are described in U.S. Provisional Application No. 63/201,389, filed Apr. 27, 2021, titled "BREATH ANALYTE DETECTION AND MEASUREMENT," which is incorporated herein by references in its entirety.

Described herein are components of an extraction solution for use in isolating and/or evaluating an analyte obtained from a breath sample and/or an ambient air sample. The extraction solution can include one or more detergents, which can assist in releasing the analyte from surfactant molecules present in the breath sample and/or the ambient air sample.

In some instances, the concentration of the detergent can be close to the critical micelle concentration (cmc). The cmc indicates the concentration at which micelles form within a solution. The cmc can depend on the structure of the detergent, as well as various conditions, such as temperature, salt concentration, pH, buffer component, etc. Non-limiting cmc values can include from about 0.01 (w/w) % to 1.0 (w/w) %; or from about 0.5 mM to 25 mM in water at 25° C. Non-limiting concentrations of one or more detergents in the extraction solution can include, e.g., from about 0.01 (w/w) % to 2.5 (w/w) %; or from about 0.5 mM to 50 mM.

Capturing the liquid drops can include the use of a droplet trap, as described herein. In particular, the droplet trap includes the use of a material that facilitates trapping of aerosol drops, as well as the elution of target analytes in the presence of the extraction solution. In one embodiment, the droplet trap includes a material, which is provided as a substrate having one or more channels. Of these channels, one or more can be configured to facilitate droplet capture through inertial impaction. Another channel can include at least one elution passage, which is in fluidic communication with the trapped aerosol droplets.

The extraction solution can be delivered to the droplet trap in any useful manner to solubilize components of the trapped sample within the droplet trap. For instance, during elution, the extraction solution can be delivered through the elution passage.

In various embodiments, in order achieve picogram sensitivity, the determining aspect of the method may involve an immunoassay or other highly sensitive detection and measurement technique, such as chemical assays, enzymatic assays, electrochemical detection/sensors, etc. Suitable immunoassays may include surface-based antibody-down immunoassays, surface-based antigen-down immunoassays, noncompetitive immunoassays, heterogeneous competitive immunoassays, and homogeneous competitive immunoassays. Several suitable immunoassays will now be described with reference to FIGS. 5-9. The operation of these immunoassays and their generalization to other recognition elements and analytes will be well understood, and implementation details for suitable immunoassays will be readily ascertained, by those of ordinary skill in the art.

As described herein, any appropriate assay or sensor, including immunoassays, chemical assays, enzymatic assays, amplification assays, ligation assays, polymerase-based assays, electrochemical detection/sensors, piezoelectrical detection/sensors, nanopore-based detection/sensors, mass spectrometry, Raman spectroscopy, infrared spectroscopy, near infrared spectroscopy, etc., may be used to detect and quantify a wide range of analytes in breath and in ambient air that are captured as described herein. The immunoassays described with specific reference to the example of the analyte THC may be readily adapted to other analytes in breath, such as are further referenced and described below, as will be well understood by those of ordinary skill in the art given the disclosure provided herein.

The assay can include any that can be used to determine an amount of the analyte or to evaluate an analyte level. In particular embodiments, the assay is an immunoassay that employs a capture agent that can directly or indirectly bind the target analyte. Further, multiple capture agents (e.g., optionally employed with one or more linkers and/or detectable labels) can be used to bind the target and provide a detectable signal for such binding. Exemplary linkers include any useful linker, such as polyethylene glycol (e.g., $(CH_2CH_2O)_m$, where $m$ is from 1 to 50), a covalent bond, an alkylene group (e.g., an optionally substituted $C_{1-2}$ alkylene or alkynyl chain), a heteroalkylene group, a carbocyclic ring (e.g., an aromatic ring, such as a phenyl group), and/or a polypeptide (e.g., a dipeptide, tripeptide, etc.). Such linkers can be installed in any useful manner, such as by using aromatic electrophilic substitution reactions, click-chemistry reactions, azo coupling reactions, etc.

Non-limiting capture agents include one or more of the following: a protein that binds to or detects one or more targets (e.g., an antibody including monoclonal or polyclonal forms thereof, an affibody, an enzyme, or fragments or recombinant forms of any of these), a globulin protein (e.g., bovine serum albumin), an amino acid, a peptide (e.g., a polypeptide, including modified forms thereof, such as glycosylated polypeptides or multimeric polypeptides), a polysaccharide (e.g., a cyclic polysaccharide), a nucleic acid (e.g., a nucleotide, a single stranded DNA, a single stranded RNA, an oligonucleotide, DNA probes, RNA probes, including modified forms of any of these), an aptamer, a thioaptamer, a lectin, a cell surface receptor, a nanoparticle, a microparticle, a sandwich assay reagent, a label (e.g., one or more fluorescent labels, colorimetric labels, quantum dots, nanoparticles, microparticles, barcodes, radio labels (e.g., RF labels or barcodes), avidin, streptavidin, biotin, tags, dyes, an enzyme that can optionally include one or more linking agents and/or one or more dyes, as well as combinations thereof), a catalyst (e.g., that reacts with one or more targets), a lipid (e.g., a glycosylated lipid), and/or an enzyme (e.g., that reacts with one or more targets, such as any described herein). The capture agent can optionally include one or more labels, e.g., any described herein. In some embodiments, more than one capture agent, optionally with one or more linking agents, can be used to detect a target of interest.

In particular embodiments, the assay is an immunoassay, in which the capture agent is an antibody that specifically binds to the target analyte. For instance, for the target analyte that is THC, the antibody can be an anti-THC antibody.

The assay can be conducted to determine an amount of the analyte. In some embodiments, the assay is conducted in the presence of the extraction solution, thereby forming a complex. In some embodiments, the complex is formed between the target analyte (e.g., an antigen) and the capture agent configured to bind the analyte (e.g., an antibody). The target analyte can include those particular analyte compounds present within the test sample or the control sample, as well as those present as immobilized compounds on any surface within the system, apparatus, or device (e.g., immobilized on surfaces of a channel, a bead, a particle, etc.). Furthermore, the complex can be formed by binding between an immobilized capture agent and a target analyte; between an immobilized target analyte and the capture agent(s); or between a target analyte and a detectable label, as can be present during various embodiments of sandwich assays, antigen-down assays, competition assays, or other immunoassay formats, as described herein.

A further operation can include forming a labeled complex having a detectable label. The labeled complex can include a target analyte bound directly or indirectly to a detectable label, which can be formed by exposing the analyte to the detectable label. Such labeled complexes can be captured by immobilized capture agents, in a direct binding or competitive binding format. In other embodiments, the labeled complex can include a target analyte, one or more capture agents, and a detectable label (e.g., which can bound directly or indirectly to the target analyte and/or the capture agent(s)).

The complex or the labeled complex can be further treated with any useful reagent to conduct a detection assay that can improve the limit of detection. For instance, one such reagent can be a signal amplification reagent, which provides a detectable signal indicative of the formation of the complex. Such a signal amplification reagent can be a tyramide reagent to conduct a tyramide signal amplification reaction, which provides a detectable signal in the presence of an enzyme (e.g., horseradish peroxidase) that can be present within the complex. In another instance, the reagent can be a connector oligonucleotide to conduct a proximity ligation assay, which provides a detectable signal in the presence of the complex having oligonucleotide tags. Other reagents and detection assays are described herein.

The labeled complex can optionally include a bead or a particle, as described herein; and the target analyte(s), capture agent(s), and/or detectable label(s) can be disposed on the bead (e.g., disposed on a surface of a bead by way of one or more optional linkers). Such beads and particles can include nanoparticles, microparticles, and such in any useful format (e.g., solid, core-shell, multilayer particles) and any useful material (e.g., metallic, polymeric, silica, magnetic, and/or fluorescent materials).

Any useful detectable label can be employed. In certain instances, the detectable label can be any that provides a detectable signal indicative of a presence or an absence of the target analyte after conducting the assay. The labels can provide a fluorescent signal, a chemiluminescent signal, an electroluminescent signal, a luminescent signal, a radiation signal, an electric signal, an electrochemical signal, an optical signal, or a colorimetric signal. Such detectable labels can be provided (e.g., by way of flow) to a reaction channel configured to conduct the assay. In some embodiments, the label is a substrate, which can include a chromogenic substrate, a fluorogenic substrate, a fluorescent substrate, a chemiluminescent substrate, and others. Such a substrate can be configured to provide a detectable signal upon performing a reaction (e.g., a binding reaction, a covalent reaction, an enzymatic reaction, etc.).

Non-limiting detectable labels can include a dye, such as an electroactive detection agent, a fluorescent dye, a luminescent dye, a chemiluminescent dye, a colorimetric dye, a radioactive agent, a particle (e.g., such as a microparticle, a nanoparticle, a latex bead, a colloidal particle, a magnetic particle, a fluorescent particle, a coated particle), a quantum dot, a nanoparticle, a microparticle, a barcode, or a label, such as an electroactive label, an electrocatalytic label, a fluorescent label, a colorimetric label, or a radio label (e.g., an RF label or barcode), an enzyme (including fragments or recombinant forms, as well as enzymes that can optionally include one or more linking agents and/or one or more dyes), a globulin protein (e.g., bovine serum albumin), an amino acid, a peptide (e.g., a polypeptide), a polysaccharide (e.g., a cyclic polysaccharide), a nucleic acid (e.g., a DNA probe, RNA probe, including modified forms of any of these), a sandwich assay reagent, a capture agent (e.g., configured to bind to the target analyte or another capture agent), avidin, streptavidin, biotin, a tag, a catalyst (e.g., that reacts with one or more reagents that can provide a detectable signal), as well as combinations thereof. Non-limiting enzymes include a peroxidase, a phosphatase, an oxidase, a lactase, a caspase, or a caspase, including horse radish peroxidase, alkaline phosphatase, glucose oxidase, beta-galactosidase, and the like.

A detectable label can include direct or indirect binding in the complex (e.g., by way of a linker or another capture agent). Furthermore, the detectable label can be bound in the complex by way of non-covalent or covalent interactions. In one embodiment, the detectable label is provided employing click-chemistry reactions, azo coupling reactions, or other reactions to directly label the analyte or the capture agent.

A click chemistry reaction can be conducted by providing a click-chemistry reaction pair having a first group and a second group. Whereas one group of the pair is provided as part of the detectable label, the other group is provided as part of the analyte or the capture agent. The first and second groups can react to from a bond. Non-limiting click-chemistry reaction pairs include those selected from a Huisgen 1,3-dipolar cycloaddition reaction between an alkynyl group and an azido group to form a triazole-containing linker; a Diels-Alder reaction between a diene having a $4\pi$ electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a $2\pi$ electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group. Either of the groups described in the reactions above can constitute the first An azo coupling reaction can be conducted by providing a reaction pair having a first group and a second group, thereby forming an azo compound. Whereas one group of the pair can be provided as part of the detectable label, the other group can be provided as part of the analyte or the capture agent. For instance, the first group can be an amino group extending from an aromatic ring, which can be converted into a diazonium group ($-N_2^+$) in the presence of nitrous acid (HONO), which is typically generated by use of sodium nitrite ($NaNO_2$) and an acid (e.g., HCl, $H_2SO_4$, and the like). The second group can include an aromatic ring, in which functional groups present in the aromatic ring can direct the position in which the azo group ($-N=N-$) is present in the resulting azo compound. For instance, if the second group includes a phenol, then the azo group is typically attached to the ortho- or para-position of the second group. Any of the detectable labels herein can be modified to include an aromatic amine, which in turn can be converted into a diazonium group for participating in an electrophilic aromatic substitution reaction with an aromatic group present in the analyte and/or the capture agent. For instance, THC includes an aromatic phenol group, which can serve as the second group in the azo coupling reaction; and a detectable label can include any having an aromatic amine. For instance, the detectable label can be NH$_2$—Ar-Lk-[D]$_b$, in which Ar is an aromatic; Lk is a multivalent linker (e.g., a bivalent, trivalent, or tetravalent linker); D is an enzyme, biotin, avidin, a dye, a label, a quantum dot, a barcode, and/or a particle; and b is 1, 2, 3, 4, or greater. In particular embodiments, Lk is an optionally substituted alkylene, optionally substituted heteroalkylene, or a polyethylene glycol. The valency of the linker Lk can correspond to the number of D components included in the detectable label. For instance, if Lk is a trivalent linker, then b can be 2 to provide two D components.

Another further operation can include measuring a detectable signal arising from the labeled complex, wherein the detectable signal is indicative of a presence or an absence of the analyte. The measuring operation can include exposing the labeled complex to a source that provides the detectable signal. The source can be configured to produce the detectable signal from the detectable label. In some embodiments, a reaction channel including the detectable label or labeled complex is exposed to the source. Non-limiting sources can include a source of radiation (e.g., electromagnetic radiation), light, optical energy, a magnetic field, an electric field, and the like.

Yet in other embodiments, a detectable signal is provided in a label-free methodology. For instance, such methodology can include mass spectrometry, Raman spectroscopy, infrared spectroscopy, or near-infrared spectroscopy, in which a label is not required. Rather, the analyte itself provides a chemical signature that indicates the presence of that analyte. For example, mass spectrometry provides one or more a molecular ion signals indicative of the ion fragments formed by a particular compound having a particular chemical structure. Similarly, Raman spectroscopy, infrared spectroscopy, and near-infrared spectroscopy provide corresponding signals indicative of the chemical structure for the analyte. Further examples are provided herein.

Such detection methodologies can be used with an immunoassay in some instances. FIGS. 5A-D depict a surface-based antibody-down, direct diazonium reporter immunoassay. According to this immunoassay, a binder for an analyte of interest in breath, in this example THC, such as a monoclonal or polyclonal antibody, peptides, or aptamers, is/are surface-bound to the reaction channel walls or beads according to well-known techniques. Such beads can include any described herein, including magnetic beads. Surface binding to the reaction channel walls or beads may be accomplished by passive adsorption, covalent binding, or a combination, for example. THC from the breath sample portion or the ambient air sample portion can be eluted using the extraction solution, which is then drawn into the reaction channel is captured by binding to the THC antibody, as depicted in FIG. 5A. In particular embodiments, this capture step is performed in the presence of the extraction solution. Suitable reagents and reaction conditions are well or readily ascertained by those of ordinary skill in the art given the description provided herein. For example, in one implementation, mouse monoclonal anti-THC antibody is immobilized on the surface via passive adsorption. In solution, THC from breath sample or the ambient air sample binds to the antibody immobilized on the capture surface.

Determining an amount of THC captured from a breath sample obtained from a subject or from an ambient air sample via this immunoassay can include flowing a detectable label. Here, this operation involves flowing a diazotized label (e.g., a diazotized fluorophore) into the reaction channel and forming a solution, such that the diazotized label binds to any THC from the breath sample portion or the ambient air sample portion that is captured by binding to the THC antibody to form a diazotized label-THC adduct, as depicted in FIG. 5B. This adduct is a labeled complex, as well as a captured complex, as described herein.

In various embodiments, the diazotized label has the formula:

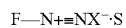

wherein:
F is a functionalized fluorophore, enzyme, biotin, avidin, dye, label, capture agent, quantum dot, barcode, and/or particle;
N+≡N is a diazonium functional group;
X⁻ is a negatively charged ion balancing the charge on the diazo functional group; and
S is a diazonium functional group stabilizer.

F can be an amine-functionalized label, such as a primary amine-functionalized label, in which the amine can be converted to form the diazonium functional group. The label can be a fluorophore, which can be any one of: xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium selenide sulfide/zinc sulfide alloy quantum dot, cadmium telluride quantum dot, cadmium sulfide quantum dot, lead sulfide quantum dot, or indium phosphide/zinc sulfide alloy quantum dot derivatives, and mixtures thereof. In particular examples, the fluorophore is a xanthene, for example a rhodamine, for example rhodamine 123, for example rhodamine 123 diazotized at a primary amine group. The label can also be a protein, such as an enzyme (e.g., a peroxidase, a phosphatase, an oxidase, a lactase, a caspase, or a protease). In other embodiments, the label can be a substrate configured to provide a detectable signal upon performing a reaction (e.g., a binding reaction, a covalent reaction, an enzymatic reaction, etc.). Non-limiting substrates can include a chromogenic substrate, a fluorogenic substrate, a chemiluminescent substrate, and others.

The F—N+≡N group of a suitable diazotized label is selected to bind to a cannabinoid. In various embodiments, the F—N+≡N binds to the para or ortho position of a phenol ring of tetrahydrocannabinol forming an N═N azo bond, such that an adduct is formed having the following formula:

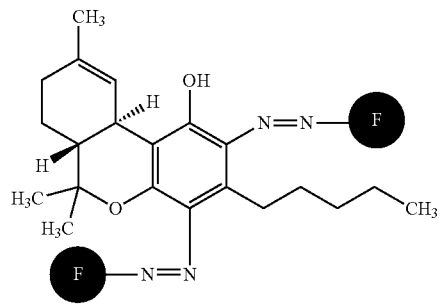

wherein F is the functionalized label, and only one or the other —N=N—F group is present.

The acidic diazotized label solution is formed from constituent materials in an acidic solution. For example, the acidic solution may contain dilute HCl, such as 100 µM HCl. Indicators/labels containing stabilized N⁺≡N diazo functional groups can be been synthesized to rapidly (e.g., <2 min) and selectively bind to THC and/or derivatives thereof at the para or ortho position of the phenol ring forming an N=N azo bond. The binding produces a chemically bonded F-labeled THC adduct. The diazotized label is generally of the form:

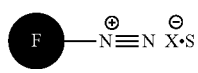

where:
- F is a fluorophore, examples of which may include xanthene, cyanine, naphthalene, coumarin, oxadiazole, anthracene, pyrene, oxazine, acridine, arylmethine, tetrapyrrole, green fluorescent protein, red fluorescent protein, yellow fluorescent protein, cadmium selenide quantum dot, cadmium selenide/zinc sulfide alloy quantum dot, cadmium selenide sulfide quantum dot, cadmium seleninde sulfide/zinc sulfide alloy quantum dot, cadmium telluride quantum dot, cadmium sulfide quantum dot, lead sulfide quantum dot, or indium phosphide/zinc sulfide alloy quantum dot derivatives; an enzyme, examples of which may include a peroxidase, a phosphatase, an oxidase, a lactase, a caspase, or a protease; biotin, avidin, or derivatives thereof; a dye, such as any described herein; a label, such as a radiolabel or any described herein; a capture agent, such as any described herein; a barcode; a particle, such as a nanoparticle or a microparticle, or any combination thereof;
- N⁺≡N is a diazonium-functional group that is chemically attached (e.g., bonded, grafted, functionalized, or conjugated) to F;
- X⁻ is a negatively charged ion that charge balances the positively charged diazo functional group N⁺≡N, examples of which may include a halide, fluoride, sulfide, chloride, nitride, bromide, iodide, arsenate, phosphate, arsenite, hydrogen phosphate, dihydrogen phosphate, borate, sulfate, nitrate, hydrogen sulfate, nitrite, thiosulfate, sulfite, perchlorate, iodate, chlorate, bromate, chlorite, hypochlorite, hypobromite, carbonate, chromate, hydrogen carbonate, dichromate, acetate, formate, cyanide, amide, cyanate, peroxide, thiocyanate, oxalate, hydroxide, or permanganate ion derivatives, or any combination thereof; and
- S is a N⁺≡N stabilizer, for prevention of decomposition of the diazo compound, composed of salts and/or polymers, examples of which may include tin chloride, cadmium chloride, manganese chloride, zinc chloride, sodium fluoroborate, aromatic, aliphatic, or heterocyclic sulfonic acids, sulfates, and chlorides, polymers with free terminal halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocarbonate ester, amide, amine, ammonium, imine, imide, azide, azo, diazo, cyanate, nitrate, nitrile, nitro, pyridine, thiol, sulfide, disulfide, sulfoxide, sulfone, sulfinic acid, sulfonic acid (e.g., naphthalene sulfonic acids, such as naphthalene-1,5-disulfonic acid and naphthalene-1,3,6-trisulfonic acid), camphosulphonic acid, thiocyanate, thione, thial, sulfonyl chloride, carbonyl chloride, phosphine, phosphonic acid, phosphate, phosphodiester, borohydrofluoric acid, boronic acid, boronic ester, boronic acid, borinic ester, fluoroborate (e.g., sodium fluoroborate), crown ether (e.g., 18-crown-6 ether), or any combination thereof.

Indicators including stabilized N⁺≡N diazo functional groups can be synthesized, for example, by a process including the combination of a primary amine (—NH₂) functionalized F (listed above), in an acidic solution (H⁺X⁻) with sodium nitrite (NaNO₂) and stabilizers, S (listed above):

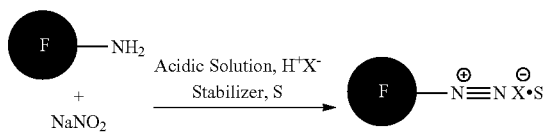

The diazotized label-THC adduct is then exposed to a source (e.g., a light source) in situ in the reaction channel to produce a detectable signal (e.g., fluorescence), as depicted in FIG. 5D. For example, the diazotized label may be rhodamine 123 diazotized at a primary amine group, the excitation wavelength may be 511 nm and the emission wavelength may be 534 nm. The fluorescence may be measured, the amount of THC captured from the sample (e.g., the breath sample or the ambient air sample) determined based on the measured fluorescence. Depending on the label or dye employed as F, different sources may be used having differing excitation wavelengths for the electromagnetic radiation, as well as differing sources of radiation, magnetic field, or electric field.

In this direct immunoassay, the measured detectable signal (e.g., fluorescence) is directly proportional to the amount of THC captured from the breath sample or the ambient air sample.

In various embodiments, prior to exposing the diazotized label-THC adduct to the light source to produce the detectable signal (e.g., fluorescence), any unbound breath constituents and unbound diazotized label are washed away from the reaction channel, as depicted in FIG. 5C. For example, the washing operation may involve flowing a buffer such as Phosphate Buffered Saline (PBS) with a surfactant, e.g., such as 0.01% Tween® 20. Other suitable buffers include tris-buffered saline and similar buffers. Particularly suitable wash buffer is generally derived empirically by the person of ordinary skill. While the detectable signal of the adduct has a spectral difference from unbound diazotized label and so can be likely detected in a homogeneous assay (without a wash step), a wash step is generally used to remove any other breath constituents that could also bind the diazotized label and therefore contaminate the assay.

FIGS. 6A-C depict a surface-based competitive antibody-down, chemiluminescence immunoassay. According to this immunoassay, a THC binder, such as a monoclonal or polyclonal antibody, peptides, or aptamers, is/are surface-bound to the reaction channel walls or beads according to well-known techniques. Such beads can include any described herein, including magnetic beads. Surface binding to the reaction channel walls or beads may be accomplished by passive adsorption, covalent binding, or a combination, for example. THC from the sample portion (e.g., the breath sample portion or the ambient air sample portion) can be eluted using the extraction solution, which is then drawn into the reaction channel is captured by binding to the THC antibody, as depicted in FIG. 6A. In particular embodiments, this capture step is performed in the presence of the extraction solution. Suitable reagents and reaction conditions are well or readily ascertained by those of ordinary skill in the art given the description provided herein, for example, as described above.

Determining an amount of THC captured from a sample (e.g., a breath sample obtained from a subject or an ambient air sample) via this immunoassay involves flowing a known amount of a detectable label. Herein, the detectable label is an enzyme, which is attached to an analyte to form a labeled complex (an enzyme-conjugated synthetic THC antigen). Other detectable labels may be employed, such as any described herein.

This complex can be flowed into the reaction channel and then form a solution. In use, any (unlabeled) THC from the sample portion (e.g., the breath sample portion or the ambient air sample portion) captured by binding to the THC antibody competes with the enzyme-conjugated synthetic THC antigen to bind to the surface-bound THC antibody, as further depicted in FIG. 6A. Here, the labeled and captured complex includes the THC antibody and the labeled-synthetic target analyte.

Then, as depicted in FIG. 6B, any unbound THC from the sample portion (e.g., the breath sample portion or the ambient air sample portion) and any unbound enzyme-conjugated synthetic THC antigen are washed away from the reaction channel.

After the wash operation, a substrate (e.g., a chemiluminescent substrate) for the enzyme is flowed into the reaction channel, and the enzyme is allowed to activate the substrate, as depicted in FIG. 6C. The resultant detectable signal (e.g., chemiluminescence for a chemiluminescent substrate) is measured, and the amount of THC captured from the sample (e.g., the breath sample or the ambient air sample) determined based on the measured chemiluminescence. Instead of chemiluminescence, other labels and dyes may be employed (e.g., fluorescent, luminescent, electroactive, colorimetric, radioactive, electrocatalytic labels or dyes) to provide other detectable signals (e.g., fluorescence, luminescence, electrical signals, color changes, radiation signals, etc.).

In various embodiments, the measuring may be done in situ in the reaction channel. In various embodiments, the measuring is done ex situ of the reaction channel in a separate fluidically-connected channel or chamber.

In this competitive immunoassay, the measured detectable signal (e.g., chemiluminescence or fluorescence) is inversely proportional to the amount of THC captured from the breath sample or the ambient air sample.

Figure 7A:
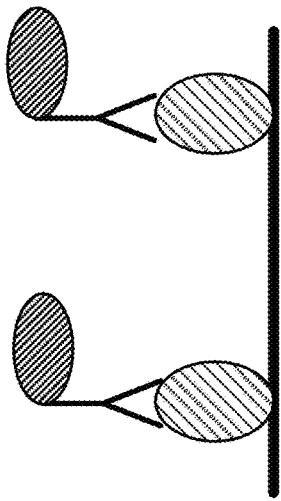
FIGS. 7A-C depict a surface-based antigen-down, heterogeneous, competitive single-antibody immunoassay.
Figure 7B:
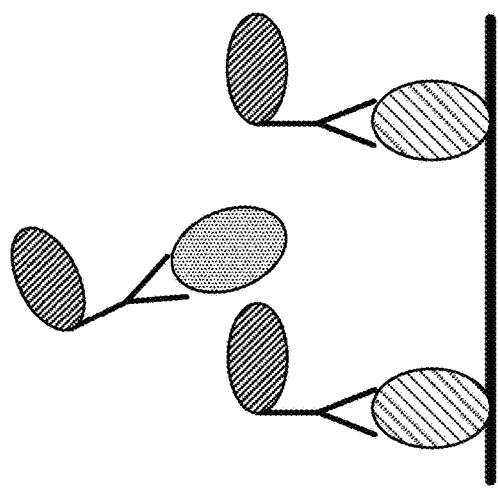
Figure 7C:
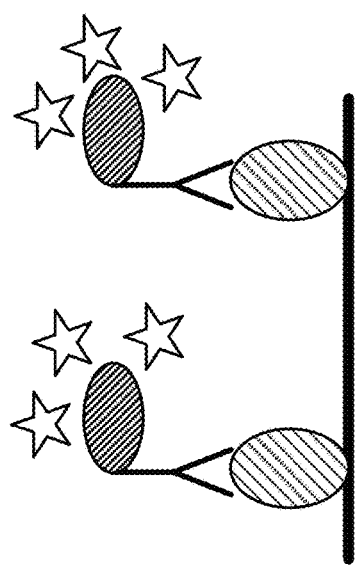

FIGS. 7A-C depicts a surface-based antigen-down, heterogeneous, competitive single-antibody immunoassay. According to this immunoassay, a synthetic THC antigen, such as THC-BSA hapten, is surface-bound to the reaction channel walls or beads. Such beads can include any described herein, including magnetic beads. Surface binding to the reaction channel walls or beads may be accomplished by passive adsorption, covalent binding, or a combination. Suitable reagents and reaction conditions are well or readily ascertained by those of ordinary skill in the art given the description provided herein.

THC from the sample portion (e.g., the breath sample portion or the ambient air sample portion) can be eluted using the extraction solution, which is then drawn into the reaction channel to be captured by adsorption on the reaction channel walls or beads. Determining an amount of THC captured from a sample (e.g., a breath sample obtained from a subject or an ambient air sample) via this immunoassay involves flowing a known amount of a detectable label. Herein, the detectable label is an enzyme, which is attached to a capture agent to form a labeled complex (an enzyme-conjugated THC antibody). Other detectable labels may be employed, such as any described herein.

This complex can be flowed into the reaction channel to form a solution with any THC from the breath sample portion or the ambient air sample portion. Any THC from the breath sample portion or the ambient air sample portion competes with the surface bound THC antigen for the enzyme-conjugated THC antibody in the solution, as depicted in FIG. 7A. Here, the labeled and captured complex includes the immobilized target analyte and the labeled-THC antibody.

Then, as depicted in FIG. 7B, any unbound THC from the sample portion (e.g., the breath sample portion or the ambient air sample portion) and any unbound enzyme-conjugated THC antibody are washed away from the reaction channel.

After the wash operation, a chemiluminescent substrate for the enzyme is flowed into the reaction channel, and the enzyme is allowed to activate the chemiluminescent substrate, as depicted in FIG. 7C. The chemiluminescence is measured, and the amount of THC captured from the sample (e.g., the breath sample or the ambient air sample) determined based on the measured chemiluminescence. Instead of chemiluminescence, other labels and dyes may be employed (e.g., fluorescent, luminescent, electroactive, colorimetric, radioactive, electrocatalytic labels or dyes) to provide other detectable signals (e.g., fluorescence, luminescence, electrical signals, color changes, radiation signals, etc.).

In various embodiments, the measuring may be done in situ in the reaction channel. In various embodiments, the measuring is done ex situ of the reaction channel in a separate fluidically-connected channel or chamber.

In this competitive immunoassay, the measured detectable signal (e.g., chemiluminescence or fluorescence) is inversely proportional to the amount of THC captured from the breath sample or the ambient air sample.

Figure 8F:
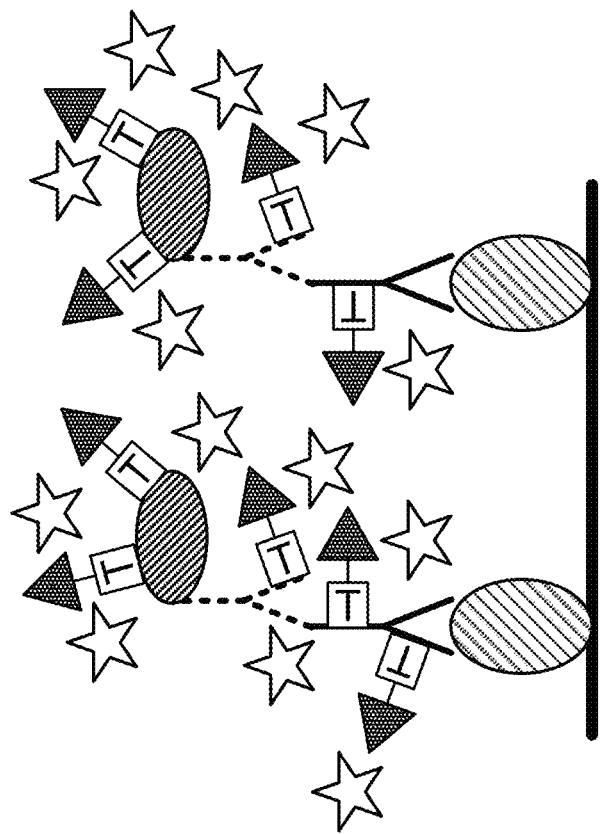
Figure 8E:
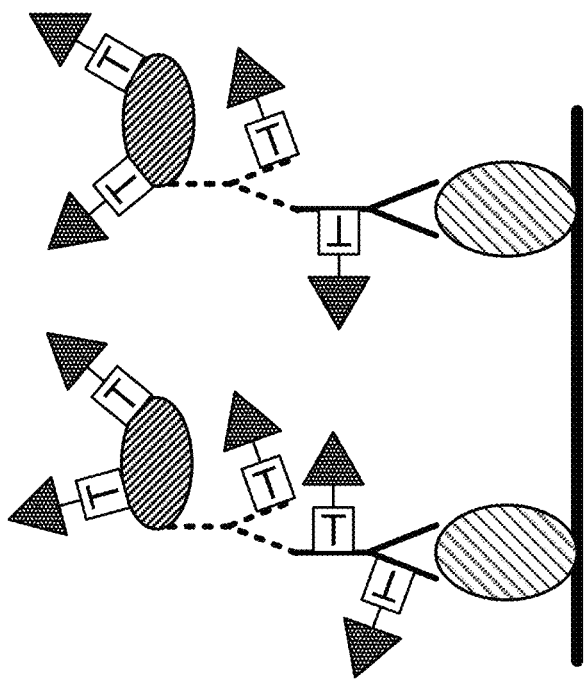

FIGS. 8A-D depicts a surface-based antigen-down, heterogeneous, competitive two-antibody immunoassay; and FIGS. 8E-F depicts an optional embodiment including a signal amplification reagent (e.g., a tyramide reagent). According to this immunoassay, a synthetic THC antigen is surface-bound to the reaction channel walls or beads according to well-known procedures, such as described above. Such beads can include any described herein, including magnetic beads. Suitable reagents and reaction conditions are well or readily ascertained by those of ordinary skill in the art given the description provided herein.

THC from the sample portion (e.g., the breath sample portion or the ambient air sample portion) can be eluted using the extraction solution, which is then drawn into the reaction channel and captured by adsorption on the reaction channel walls or beads. Determining an amount of THC captured from the sample (e.g., a breath sample obtained from a subject or an ambient air sample) via this immunoassay involves flowing a known amount of a THC antibody into the reaction channel and forming a solution with any THC from the breath sample portion or the ambient air sample portion, such that any THC from the sample portion competes with the surface bound THC antigen for the THC antibody in the solution, as depicted in FIG. 8A.

Then, as depicted in FIG. 8B, any unbound THC from the sample portion (e.g., the breath sample portion or the ambient air sample portion) and any unbound THC antibody are washed away from the reaction channel.

After this wash operation, a detectable label is flowed into the reaction channel. Here, the detectable label is an enzyme-conjugated second antibody, which is flowed into the reaction channel forming a solution, such that the enzyme-conjugated second antibody binds to the THC antibody on the surface bound THC antigen, as depicted in FIG. 8C. Here, the labeled and captured complex includes the immobilized THC antigen, the capture agent bound to the antigen, and a secondary capture agent that includes a detectable label (the enzyme-conjugated second antibody).

Then, any unbound THC from the sample portion (e.g., the breath sample portion or the ambient air sample portion) and any unbound THC antibody are washed away from the reaction channel.

After this second wash operation, a chemiluminescent substrate for the enzyme is flowed into the reaction channel and the enzyme is allowed to activate the chemiluminescent substrate, as depicted in FIG. 8D. The chemiluminescence is measured, and the amount of THC captured from the sample (e.g., the breath sample or the ambient air sample) determined based on the measured chemiluminescence. Instead of chemiluminescence, other labels and dyes may be employed (e.g., fluorescent, luminescent, electroactive, colorimetric, radioactive, electrocatalytic labels or dyes) to provide other detectable signals (e.g., fluorescence, luminescence, electrical signals, color changes, radiation signals, etc.).

In various embodiments, the measuring may be done in situ in the reaction channel. In various embodiments, the measuring is done ex situ of the reaction channel in a separate fluidically-connected channel or chamber.

In this competitive immunoassay, the measured detectable signal (e.g., chemiluminescence or fluorescence) is inversely proportional to the amount of THC captured from the breath sample or the ambient air sample.

Tyramide signal amplification can be employed, in which a tyramine- or tyramide-based reagent (referred herein as a tyramide reagent) is employed in the presence of an enzyme to activate the tyramide reagent. For instance, in the presence of an enzyme, such as HRP, the tyramide reagent becomes activated (e.g., peroxidated), which in turn reacts with electron rich moieties (e.g., tyrosine or tryptophan) and forms covalent bonds. If the enzyme is conjugated to an antibody, then introduction of the tyramide reagent can result in reaction with the enzyme, thereby providing a bound tyramide reagent. In this way, tyramide reagent (as well as any label attached to the tyramide reagent) is deposited.

The tyramide reagent, in turn, can include further detectable labels, thereby amplifying a detectable signal indicative of the presence of the target. Detection systems and signal amplification agents, such as detectably labeled phenols, activated conjugates, are described in U.S. Pat. Nos. 5,731,158, 5,583,001, and 5,196,306, as well as PerkinElmer Inc., "TSA Signal Amplification (TSA) Systems," Document No. 007703_01, 16 pages, accessed at perkinelmer.com/lab-solutions/resources/docs/BRO_tsasignalamplification systems.pdf, each of which is incorporated herein by reference in its entirety.

In one embodiment, the assay can include conducting an immunoassay with HRP-conjugated antibody but adding a tyramide reagent at the end (instead of luminol), as depicted in FIG. 8E in which "T" indicates the tyramide reagent. These reagents can then react with HRP to bind a fluorophore or other molecule nearby, as depicted in FIG. 8F.

Such a tyramide reagent can be employed in cycles to exponentially boost a detectable signal. For instance, a biotin-labeled tyramide reagent and a streptavidin-labeled HRP can be introduced to the chamber or channel in cycles. One non-limiting embodiment can include steps to incubate with the biotin-labeled tyramide reagent, wash, incubate with a streptavidin-labeled HRP (which will bind to all of the new biotin-labeled reagents deposited near the antibodies), wash, incubate with a biotin-labeled tyramide reagent again with all of the just deposited HRPs participating during the biotin deposition reaction, and then repeat as needed.

In various implementations of the chemiluminescent embodiments described above with reference to FIGS. 6, 7, and 8, the enzyme may be horseradish peroxidase (HRP) and the substrate may be, for example, TMB (3,3', 5,5'-tetramethylbenzidine), which gives blue reaction products upon reaction with HRP that have major absorbance peaks at 370 nm and 652 nm; OPD (o-phenylenediamine) which gives a yellow-orange, water-soluble reaction product with an absorbance maximum of 492 nm upon reaction with HRP; or ABTS (2,2'-azinobis [3-ethylbenzothiazoline-6-sulfonic acid]) which gives a green, water-soluble end reaction product upon reaction with HRP that gives two major absorbance peaks at 410 nm and 650 nm. These reagents are available from Sigma-Aldrich.

FIGS. 9A-C depicts a homogeneous competitive immunoassay. According to this immunoassay, THC from a sample portion (e.g., the breath sample portion or the ambient air sample portion) drawn into the reaction channel is captured by adsorption on the reaction channel walls, as depicted in FIG. 9A. Determining an amount of THC captured from a sample (e.g., a breath sample obtained from a subject or an ambient air sample) via this immunoassay involves a luminescent oxygen channeling immunoassay (LOCI™) or AlphaLISA™ immunoassay, such as are described in *Luminescent oxygen channeling assay (LOCIT™): sensitive, broadly applicable homogeneous immunoassay method*, E. F. Ullman et al., Clinical Chemistry, 42:9, 1518 (1996); and *AlphaLISA immunoassays: the no-wash alternative to ELISAs for research and drug discovery*, L. Beaudet et al., Perkin Elmer Application Notes, December 2008; incorporated by reference herein for background and details of the two assays. Antibody specific to THC is immobilized on donor beads, either by direct adsorption or via Streptavidin-Biotin linkage. Acceptor beads are prepared by adsorbing a synthetic THC antigen.

In this context, these immunoassays involve flowing donor beads and acceptor beads into the reaction channel and forming a solution with any THC from the breath sample portion or the ambient air sample portion, such that any THC from the sample portion competes with synthetic THC bound to the acceptor beads to bind to antibody immobilized on the donor beads, as depicted in FIG. 9B. Donor beads bind either to free THC from the sample portion or to the acceptor beads' immobilized THC. The higher the concentration of free THC from breath sample or the ambient air sample, the lower the concentration of donor bead—acceptor bead pairs.

The donor bead-acceptor bead pairs in the solution are then exposed to a light source in situ in the reaction channel to produce a fluorescence, as depicted in FIG. 9C. For example, the, the excitation wavelength may be 680 nm, and the emission wavelength may be 615 nm. This fluorescence signal is only emitted when the donor and acceptor beads are in close proximity to each other. This results in only bound pairs emitting light, while free beads do not emit any light. This reaction, which only occurs between beads which are in close proximity is what allows the homogenous phase immunoassay, without the requirement for washing, which is integral to traditional surface-based immunoassays.

The detectable signal (e.g., fluorescence) may be measured and the amount of THC captured from the breath sample or the ambient air sample determined based on the measured fluorescence.

In this competitive, homogeneous immunoassay, the measured fluorescence is inversely proportional to the amount of THC captured from the breath sample or the ambient air sample.

Following completion of one of the immunoassay formats described above, the determined amount of THC captured the breath sample may be compared to a threshold level for THC in breath, such as described above with reference to FIG. 4, for example, less than 10 picogram/liter (pg/L) of breath, or from 2 to 5 pg/L of breath, or from 2 to 3 pg/L of breath, for example, about 2.4 pg/L of breath. However, as noted above, the threshold may vary depending upon the capture efficiency of the device or system with which the method is conducted. In other embodiments, the determined amount of THC captured the breath sample may be compared to a background level of THC in ambient air.

Then, it may be indicated whether or not the amount of THC captured from the breath sample exceeds the threshold level or the background level. A result wherein the amount of THC in the breath sample exceeds the threshold and/or the background levels may be a positive test result for recent inhalation of THC, which may be correlated to THC impairment. In various embodiments, the indicating may include a visible and/or audible signal and/or readout on a display associated with a device on which the determination and comparison is conducted.

Any useful detection methodology can be employed with an immunoassay. In one embodiment, a proximity ligation assay (PLA) can be employed to detect oligonucleotide-labeled targets. For instance, PLA involves tagging molecules with DNA sequences that can be ligated if they come into close proximity. This ligated DNA (a circular DNA template) can be amplified by rolling circle amplification (RCA) to produce an amplicon, followed by LAMP or PCR, if desired. The amplicon can then be detected by using labeled oligonucleotide probes, which can be designed to hybridize with particular complementary sequences within the amplicon. Alternatively, the amplicon can be detected by using intercalating fluorophores to bind to double stranded regions within the amplicon.

In one embodiment, the assay can include conducting a competitive immunoassay (e.g., as described herein), in which both the synthetic THC antigen and the anti-THC antibody are labeled with oligonucleotide (oligo) probes to provide an oligo-labeled THC and an oligo-labeled anti-THC antibody. In use, the oligo-labeled THC can compete with THC from a sample (e.g., a breath sample or an ambient air sample), thereby resulting in a differential signal.

If both of the oligo-labeled THC and anti-THC antibody are in proximity to each other, then a hybridizing connector oligonucleotide is introduced (after conducting the immunoassay) to join the oligo probes. Then, a ligase is provided to ligate the oligo probes and the connector oligonucleotide, thereby forming a circular template amenable for RCA. The resulting amplicon can be then detected by using intercalating fluorophores or hybridizing fluorophore-labelled oligonucleotides.

In other embodiments, a piezoelectrical analysis system can be employed to detect changes in acoustic frequency based on the presence of a target in proximity to a piezoelectric material. Non-limiting piezoelectric materials include zinc oxide, lead zirconate titanate (PZT), aluminum nitride, indium nitride, and the like, which can be provided as a membrane, a film, or a substrate.

Generally, a current is applied to the piezoelectric material to provide an oscillating circuit that is characterized by a certain frequency. Adsorption of molecules on the piezoelectric material can change the mass of the material, which in turn can result in a detectable frequency change. In particular, this methodology can be optionally employed with a bead-based reagent, which can provide a larger change in mass with a commensurate larger frequency change. Furthermore, magnetic flux or magnetic fields can be employed to provide bead-based reagents to the piezoelectric material in a controlled manner.

In one embodiment, the assay can include conducting a competitive immunoassay in the presence of a piezoelectric material. THC from a sample (e.g., a breath sample or an ambient air sample) could compete with a synthetic THC antigen that is attached to a magnetic bead (e.g., via COOH chemistry) (a THC-bead reagent). The capture antibody can be attached to the piezoelectric material by way of chemisorption, physisorption, etc. The presence of the THC-bead reagent bound to the capture antibody can alter the oscillation frequency of the piezoelectric material when it is actuated (e.g., by applying an AC field to the piezoelectric material). THC from the sample would competitively displace the THC-bead reagent from the capture antibody (which is in turn attached to this membrane), thus resulting in a differential signal.

Non-limiting methods for a bead-based system with a piezoelectric membrane-based approach is described in, e.g., Jokerst J V et al., "A Magnetic Bead-Based Sensor for the Quantification of Multiple Prostate Cancer Biomarkers," *PLoS ONE* 2015; 10(9): e0139484 (15 pages), which is incorporated herein by reference in its entirety.

The principle of Electrochemical Impedance Spectroscopy (EIS) is that large proteins can be detected electrically. For instance, EIS can be employed to detect changes in impendence based on the presence of a target in proximity to an electrode. Such electrodes can be patterned in any useful manner on a substrate, and an anti-THC antibody can be attached to a surface of the electrode (e.g., directly or by way of a linker). Upon applying a current to the electrode, the resultant current response or impedance can be determined.

In one embodiment, the assay can include conducting a competitive immunoassay in the presence of an electrode having an immobilized anti-THC antibody. Here, THC from a sample (e.g., a breath sample or an ambient air sample) could compete with a synthetic THC antigen bound to a protein (e.g., BSA) (a protein-THC reagent) for binding to the anti-THC antibody. The protein can be detected by measuring the impedance at the electrode (the surface on which the antibody is bound) with an AC signal. Since the protein-THC reagent competes with the THC in the sample, the amount of protein on the electrode will be inversely proportional to the amount of THC in the breath sample or the ambient air sample.

Non-limiting methods for an EIS-based biosensor is described in, e.g., Stevenson H et al., "A rapid response electrochemical biosensor for detecting THC in saliva," *Sci. Rep.* 2019; 9:12701 (11 pages), which is incorporated herein by reference in its entirety.

Nanopore-based analysis can be employed to detect transient decreases in ionic conductivity when a target either blocks or translocates through a nanopore. Such transient conductivity events can be measured providing a nanopore within a fluid chamber, applying a voltage across the nanopore, and measuring current as a target from the fluid chamber enters the nanopore. To obtain specificity for the target, the surface of the nanopore can be functionalized, e.g., with an anti-THC antibody. Nanopores can be provided as a single nanopore or as an array (e.g., an m×n array of nanopores, in which each of m and n is 1 or more) within any useful substrate (e.g., a semiconductor substrate). The nanopore can have any useful shape, size, or length (through the substrate).

In one embodiment, the assay can include conducting a competitive immunoassay in the presence of a nanopore having an immobilized anti-THC antibody. Here, THC from a sample (e.g., a breath sample or an ambient air sample) could compete with a synthetic THC antigen bound to a bead (a THC-bead reagent). The extent of blocking provided by THC or a THC-bead reagent can be distinguished and, optionally, the number of such blocking events can be counted over time.

Alternatively, a magnetic bead can be employed, in which such beads can then be magnetically driven through the nanopores in a membrane. Immobilized antibodies that are not bound to free THC from the sample (e.g., the breath sample or the ambient air sample) can then be available to bind the THC-bead reagent. Then, the magnetic field can be reversed to remove unbound beads. The beads remaining on the membrane can then be detected with labelled anti-THC antibodies.

Non-limiting methods for a nanopore-based sensor is described in, e.g., Chuah K et al., "Nanopore blockade sensors for ultrasensitive detection of proteins in complex biological samples," *Nat. Commun.* 2019; 10: 2109 (9 pages), which is incorporated herein by reference in its entirety.

Other label-free spectroscopy methods can be used to detect the analyte. For instance, mass spectrometry (MS) can be employed to obtain a spectrum, and detection can include assessing whether the spectrum includes a chemical signature (e.g., molecular ion signals) indicative of the presence of the analyte. Such methods can be combined with other analytic methods, such as in gas chromatography-mass spectrometry (GC-MS), liquid chromatography-mass spectrometry (LC-MS), and the like.

In another instance, Raman spectroscopy can be employed, including surface-enhanced Raman spectroscopy (SERS) by using a SERS-active substrate that causes excitement of localized surface plasmons upon exposure to a laser light, thereby enhancing Raman signals and allowing for trace detection of THC. Such SERS-active substrates can include a metal, including a metal film or metal particles, including metal nanoparticles. Non-limiting methods and devices relating to SERS detection is described in, e.g., U.S. application Ser. No. 17/302,801, filed May 12, 2021, "Systems and methods using surface-enhanced Raman spectroscopy for detecting tetrahydrocannabinol", which is incorporated herein by reference in its entirety.

In yet another instance, infrared (IR, from 40 to 13,000 $cm^{-1}$) or near IR (from 10,000 to 4000 $cm^{-1}$) spectroscopy can be employed, including Fourier Transform (FT) forms thereof. Any of these spectroscopic analyses can include further data analysis, such as by way of principal component analysis (PCA) or principal component regression (PCR).

Non-limiting methods for spectroscopic analysis of analytes, such as with FTIR, is described in, e.g., Townsend D et al., "Application Note: The Determination of Total THC and CBD Content in *Cannabis* Flower by Fourier Transform Near Infrared Spectroscopy," 2018; Document No. 014329_01, 5 pages, accessed at perkinelmer.com/lab-solutions/resources/docs/app_determination_of_thc_and_cbd_cannabisflower.pdf, which is incorporated herein by reference in its entirety.

In various embodiments, the test cartridge on which methods described herein, particularly immunoassays, are conducted may be a microfluidic device or a minifluidic device. The device can include any useful fluidic structure, including those having a rigid material or a flexible material.

In various embodiments, data (e.g., any described herein related to an amount of the analyte, the threshold level, and/or the background level) may be wirelessly transmitted to a remote location. In some instances, one or more processors and memory may include at least one processor and memory that are part of a device associated with the test cartridge. In such cases, there may be processors and memory distributed between two or more components, and the components may communicate with one another, either through a wireless communications interface or a wired connection.

In some implementations, one or more of the components may also have a wireless communications interface, e.g., a cellular interface, that allows the one or more processors to wirelessly communicate information to a remote device, e.g., a server. For example, the device associated with the test cartridge may include a wireless interface that may transmit data (as either entered manually by a user or as obtained automatically, e.g., through use of a GPS receiver located in the device or in another nearby piece of equipment, such as a paired smartphone or police car), and possibly other data such as one or more fingerprints of a subject, and/or a picture of the subject providing the sample, e.g., as taken by a paired smartphone or by a camera that may be built in to the device.

The same wireless communications interface, or a different wireless communications interface, may also communicate test results to the same remote device in association with such information or in association with a record identifier linking such further information to previously transmitted information, allowing test results to be associated with a particular subject and sampling time/location. In some implementations, the wireless interface that may allow for such long-range communications, e.g., a cellular interface, may be integrated into only one of the components of the device, and the other components may communicate wirelessly with the base station using shorter-range communications systems, e.g., Bluetooth, and the base station may then act as a relay and send data collected by the other components on to the remote device.

In various embodiments, the breath sample obtained from the subject is also tested for a second substance, in particular ethanol, such that both THC and ethanol are measured from the same breath sample. According to such embodiments, another portion of the breath sample may be routed through a blood alcohol concentration (BAC) sensor for ethanol measurement. BAC sensors (e.g., a fuel call-based BAC sensor) and their operation are well known in the art. Any suitable BAC sensors may be integrated with a device associated with the test cartridge, for example fuel cell based sensors from PAS Systems, Inc.

In various embodiments, the breath sample may be obtained from the subject after exposing the subject to a well-ventilated area (for example, outdoors) for at least 15 minutes. Subjects exposed to secondhand smoke will only have THC in their breath for a very brief time, and it disappears after a person is no longer exposed to this smoke. Accordingly, subjects exposed to secondhand smoke can be placed outdoors or in a well-ventilated area for 15 minutes before a breath test is performed to avoid a false positive associated with secondhand smoke exposure. In further embodiments, the ambient air sample can be obtained from the well-ventilated area.

In various embodiments, in order to meet the evidentiary standards associated with roadside sobriety tests, an equal portion of the breath sample as drawn into the reaction channel may be drawn into an evidence channel on the test cartridge. This "B" sample can be retained for future testing to validate the test result. The "B" sample may be eluted from the evidence channel into a solution in a separate receptacle, or left in the evidence channel on the test cartridge channel, for storage or off-site analysis. A similar process can be used to provide separated ambient air samples. For instance, an equal portion of the ambient air sample as drawn into the reaction channel may be drawn into an evidence channel on the test cartridge.

The methods, systems and apparatus described herein may also be adaptable as a platform for detection and evaluation of other airborne/breath-borne substances, including controlled substances, in a breath sample and/or an ambient air sample. In this regard, this disclosure also relates to a method for evaluating a substance (or analyte), more generally, in human breath, the method involving determining an amount of a substance captured from a breath sample obtained from a subject, comparing the determined amount of the substance captured from the breath sample to a threshold level for the substance in breath or a background level for the substance in ambient air, and indicating whether or not the determined amount of the substance captured from the breath sample exceeds the threshold and/or the background levels.

In view of the above, it will be understood that methods, systems, and apparatuses for measuring or detecting breath-borne analytes or target substances from an exhaled breath sample and an ambient air sample are disclosed herein. In various implementations, this disclosure also relates to systems and apparatus for measuring tetrahydrocannabinol (THC) level from a breath sample in accordance with the methods herein described. Such a system, and variants thereof, is discussed in more detail below.

Figure 10:
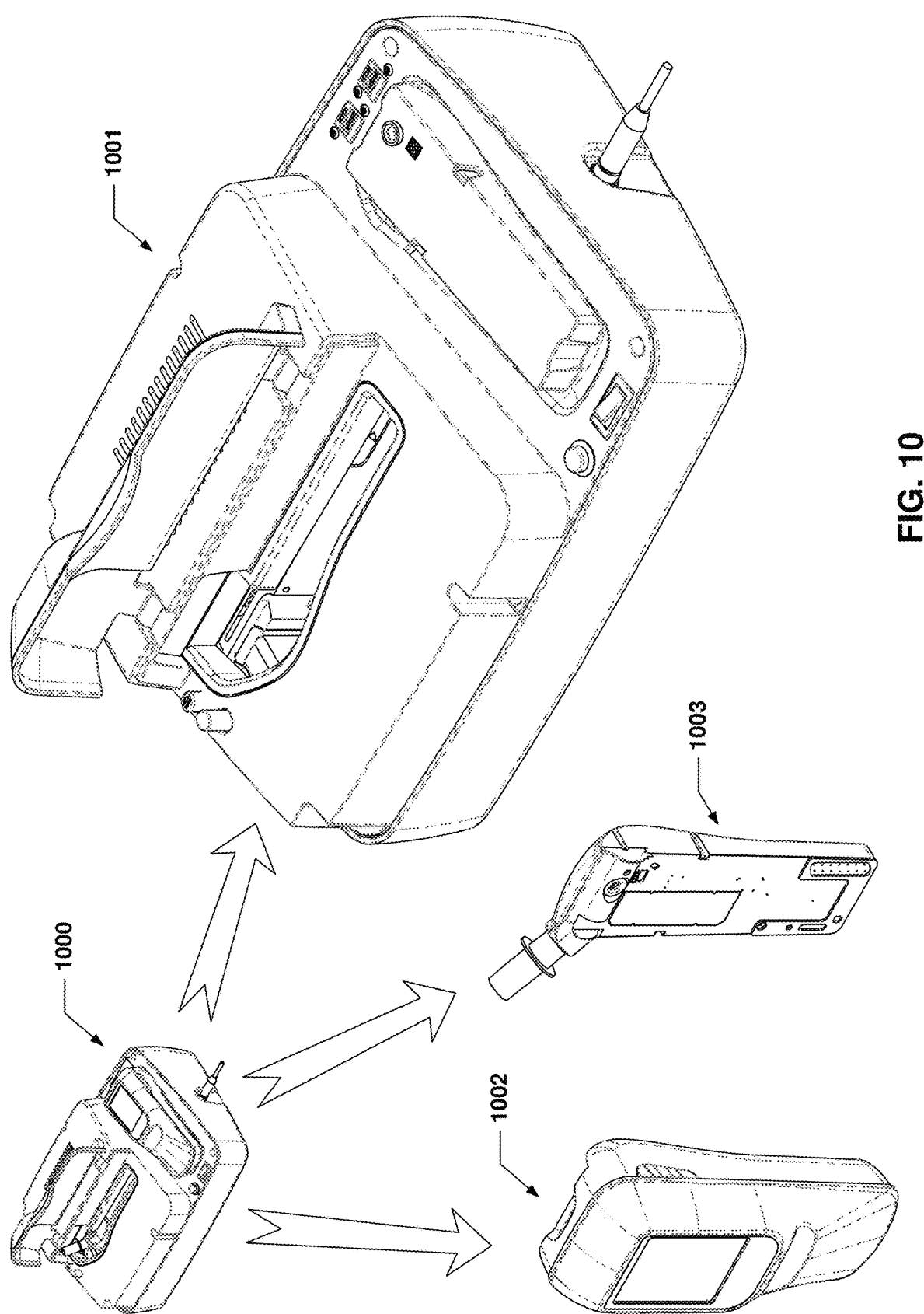
FIG. 10 depicts an example breath sampling and analysis system.

FIG. 10 depicts an example breath sampling and analysis system. In the depicted example system 1000, the system includes three main components—a base station 1001, a handheld unit 1002, and a cartridge, or disposable, 1003. This example breath sampling and analysis system will be used herein to discuss various aspects of breath sampling and analysis systems according to the present disclosure in general, but it will be understood that other implementations of breath sampling and analysis systems according to the concepts disclosed herein may take other forms. For example, while the example system features the base station 1001, the handheld unit 1002, and the cartridge 1003, other systems may combine or otherwise distribute the functionality of one or more of these elements into other components. For example, the handheld unit 1002 may be connected with the cartridge 1003 in order to collect a breath sample and/or an ambient air sample, as the handheld unit 1002 is small, relatively lightweight, and easily wielded by whomever is obtaining the breath sample. The cartridge 1003 may then be removed from the handheld unit 1002 and both elements separately docked in the base station 1001 in order to perform the analysis and report out the results. However, it will be understood that, for example, the base station 1001 and the handheld unit 1002 could be combined into one device, although the resulting apparatus would not be as portable as the handheld unit 1002 and obtaining a breath sample using such an apparatus would likely require extra effort on behalf of the subject. Similarly, the functionality of the cartridge 1003 could be combined with the handheld unit 1002, although doing so may complicate cleaning and re-use of the handheld unit 1002.

While the breath sampling and analysis system 1000 discussed herein as an example is designed for use as a THC and alcohol detection system, it will be understood that similar systems, with appropriate modification, may be used to detect one or more additional or alternative analytes, as noted earlier. For example, the breath sampling and analysis system architecture discussed herein may also be used generally to capture breath samples and ambient air samples that may then be analyzed to determine amounts of other controlled substances (or byproducts of using such controlled substances). In general, the systems and architecture provided herein allow for breath samples and ambient air samples containing potentially very small volumetric densities or concentrations of analytes, e.g., with magnitudes on the picogram-per-liter scale, to be captured and concentrated in reaction volumes on the order of microliters or tens of microliters within microfluidic circuits/plates. Once captured, such volumes may be analyzed to determine the presence and quantity of a particular analyte of interest, e.g., according to any of the assay techniques discussed earlier. As discussed, while most of the discussion herein is with reference to an example such system for detecting THC, the principles set forth herein, and the overall architecture, may be applicable to systems for detecting a variety of different analytes, and the concepts laid out herein should not be viewed as being solely directed to THC detection systems and methods.

The cartridge 1003 can include a substrate that is a microfluidic plate containing a microfluidic circuit, which in turn includes one or more optical measurement chambers that are fluidically connected or connectable with the first and/or second elution passage within the microfluidic plate. Furthermore, the base station 1001 may include an optical measurement module that may be communicatively coupled with a controller and positioned so as to obtain optical signal measurements from one or more locations of the cartridge 1003.

As used herein, a cartridge generally refers to a device for processing and analyzing sample. Such a cartridge can include any type of material (e.g., flexible, rigid, as well as combinations thereof) to define any useful fluidic circuit to provide fluidic communication. In particular embodiments, the fluidic circuit can be provided within a flexible fluidic structure with an associated fluidic system, as described herein (see, e.g., FIGS. 15-21).

Fluidic communication, as the phrase is used herein, refers to a state in which two or more volumes are connected by one or more passages, orifices, or other features such that fluid may flow between them. Generally speaking, the phrase should be understood to imply that there is some form of structure providing the fluidic communication, rather than just exposure to the ambient environment. For example, two open-topped buckets positioned side-by-side in upright positions would not be considered to be in "fluidic communication" (even though fluid, e.g., gas, could conceivably waft of diffuse from one bucket to the other), whereas placing an end of a hose into each of those same two open-topped buckets would cause the buckets to be viewed as being in "fluidic communication" with each other since there is structure that serves to provide a fluid flow passage between them.

Fluidically interposed, as the phrase is used herein, refers to a condition where fluid flowing from a first component to a second component generally flows through a third component before reaching the second component; the third component would be described as being fluidically interposed between the first and second components. For example, a furnace may be connected with a heating register by a duct; the duct would be described as being fluidically interposed between the furnace and the heating register since the heated air from the furnace would generally flow through the duct before reaching the heating register. In systems using gas as the fluid, there may be some leak paths or other flow paths that allow for the fluid to flow from one component to another without flowing through a component that is fluidically interposed between those two components, but it should be understood that if the majority of the fluid that flows between those two components passes through a third component before reaching the latter of the two components, then that third component may still be deemed to be "fluidically interposed" between the two components. It will be further understood that a component that is fluidically interposed between two other components does not necessarily mean that the component is physically located in between the other two components. For example, components A, B, and C may be physically arranged in a line in that order, with B physically located between A and C. However, hoses may connect A to C and then C to B such that C is fluidically interposed between A and B.

In particular implementations, the cartridge may be specially adapted for obtaining adequately sized breath samples within a 60 to 90 second sampling interval for an average human male. In such implementations, the reaction channels may be sized so as to each have hydraulic diameters of 0.8 mm or less, 0.75 mm or less, 0.7 mm or less, 0.65 mm or less, or 0.6 mm or less and be approximately, e.g., within ±5 mm of, 40 mm, 50 mm, 60 mm, or 70 mm in length, although longer channel lengths may also be used. Other hydraulic diameters, channel lengths, and/or channel geometries can be provided to provide a desired capture efficiency of the droplets or particles.

The cartridge 1003 can include a fluidic circuit (e.g., a flexible fluidic circuit) having fluidic sub-circuits. In particular, a first fluidic sub-circuit can be configured to introduce a sample collected from exhaled breath; and a second fluidic sub-circuit can be configured to introduce a sample into the fluidic structure that has been collected from ambient air (as opposed to from a subject's lung exhalations). Such a fluidic structure may be used to simultaneously obtain samples from, for example, a human subject's lungs, e.g., a breath sample, as well as from ambient air. In the latter case, a vacuum pump may be used to draw ambient air through a sampling system similar to that used to collect a breath sample from the test subject. Such a structure may permit the amount of biomarker in the test subject's sample to be adjusted to account for the amount of biomarker that may be in the ambient air. For example, if a reading of 40 units of biomarker is measured from the test subject's sample, but the ambient air is measured to have 30 units of biomarker present, then the test subject's biomarker measurement may be corrected to remove the portion thereof that may have been preexisting, i.e., 40 units minus 30 units, which would leave a corrected measurement of 10 units.

While numerous specific fluidic structures have been described above in conjunction with the implementations depicted in the figures, various other implementations of fluidic structures will also be understood to fall within the scope of this disclosure, including fluidic structures that combine two or more of the fluidic structures discussed herein, or that may blend the features of two fluidic structures together.

Methods herein can be implemented (e.g., within the handheld unit, cartridge, fluidic structure, and/or base station) or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

This application incorporates by reference the following applications for their disclosure relating to implementation of biomarker (which may be considered an analyte) capture, collection, detection, measurement and analysis methods and apparatus that are suitable for implementation of the disclosed methods and devices: U.S. application Ser. No. 16/425,938, filed May 29, 2019, titled "SINGLE-USE MICROFLUIDIC CARTRIDGE FOR DETECTION OF TARGET CHEMICAL PRESENCE IN HUMAN BREATH" and U.S. application Ser. No. 16/425,943, filed May 29, 2019, titled "MECHANICAL BREATH COLLECTION DEVICE" and International Application No. PCT/US2020/013553, filed Jan. 14, 2020, published as International Publication No. WO 2020/159698, titled "MECHANICAL BREATH COLLECTION DEVICE" and U.S. application Ser. No. 16/776,501, filed Jan. 29, 2020, titled "NONINVASIVE POINT OF CARE BIOMARKER DETECTION FROM BREATH SAMPLES," each of which claims priority to U.S. Provisional Patent Application No. 62/799,675, filed Jan. 31, 2019, titled "NON-INVASIVE POINT OF CARE BIOMARKER DETECTION FROM BREATH SAMPLES"; U.S. application Ser. No. 16/729,116, filed Dec. 27, 2019, titled "ANALYTE DETECTION FROM BREATH SAMPLES," which claims priority to U.S. Provisional Patent Application No. 62/786,222, filed Dec. 28, 2018, titled "ANALYTE DETECTION FROM BREATH SAMPLES"; U.S. application Ser. No. 16/823,113, filed Mar. 18, 2020, titled "BIOMARKER DETECTION FROM BREATH SAMPLES," which claims priority to U.S. Provisional Application No. 62/821,900, filed Mar. 21, 2019, titled "BIOMARKER DETECTION FROM BREATH SAMPLES"; from U.S. application Ser. No. 16/124,181, filed Sep. 6, 2018, titled "ANALYTE DETECTION FROM BREATH SAMPLES," which claims priority to U.S. Provisional Application No. 62/646,798, filed Mar. 22, 2018, titled "ANALYTE DETECTION FROM BREATH SAMPLES"; U.S. application Ser. No. 16/655,182, filed Oct. 19, 2019, titled "ROTARY VALVE ASSEMBLIES AND METHODS OF USE FOR BREATH SAMPLE CARTRIDGE SYSTEMS," which claims priority to U.S. Provisional Application No. 62/746,858, filed Oct. 17, 2018, titled "BREATH SAMPLE CARTRIDGE AND SYSTEM"; U.S. Provisional Application No. 63/201,062, filed Apr. 9, 2021, titled "FLEXIBLE FLUIDIC CIRCUITS"; U.S. Provisional Application No. 63/201,389, filed Apr. 27, 2021, titled "BREATH ANALYTE DETECTION AND MEASUREMENT"; and U.S. application Ser. No. 17/302,801, filed May 12, 2021, titled "SYSTEMS AND METHODS USING SURFACE-ENHANCED RAMAN SPECTROSCOPY FOR DETECTING TETRAHYDROCANNABINOL," which claim priority to U.S. Provisional Application No. 63/024,423, filed May 13, 2020, SYSTEMS AND METHODS USING SURFACE-ENHANCED RAMAN SPECTROSCOPY FOR DETECTING TETRAHYDROCANNABINOL."

This application also incorporates by reference the following applications for their disclosure relating to implementation of biomarker (or analyte) collection and detection methods and apparatus that are suitable for implementation of the disclosed methods and devices: U.S. Provisional Application No. 62/557,056, filed Sep. 11, 2017, titled "IMMUNOASSAY METHODS FOR DETECTING THC IN BREATH"; U.S. Provisional Application No. 62/557,060, filed Sep. 11, 2017, titled "DIAGNOSTIC AND ANALYTICAL ASSAY PERFORMANCE FOR THC IMMUNOASSAY"; U.S. Provisional Application No. 62/616,380, filed Jan. 11, 2018, which is titled "METHOD AND DEVICE FOR MEASURING THC LEVEL FROM BREATH SAMPLE"; U.S. Provisional Patent Application No. 62/337,286, filed May 16, 2016, and titled "BREATH COLLECTOR MODULE"; U.S. Provisional Patent Application No. 62/351,858, filed Jun. 17, 2016, and titled "COMPOSITIONS AND METHODS FOR DETECTION OF TARGET CONSTITUENT IN EXHALED BREATH"; U.S. Provisional Patent Application No. 62/351,821, filed Jun. 17, 2016, and titled "SYSTEM AND METHOD FOR TARGET SUBSTANCE IDENTIFICATION"; U.S. patent application Ser. No. 15/217,151, filed Jul. 22, 2016, and titled "COMPOSITIONS AND METHODS FOR DETECTION OF TARGET CONSTITUENT IN EXHALED BREATH"; U.S. Provisional Patent Application No. 62/351,858, filed Jun. 17, 2016, and U.S. patent application Ser. No. 14/997,405, titled "METHOD, DEVICE AND SYSTEM FOR TARGET SUBSTANCE DETECTION" and filed Jan. 15, 2016; U.S. Provisional Application Nos. 62/104,813, filed Jan. 18, 2015, and 62/107,331, filed Jan. 23, 2015, both of which are titled "METHOD, DEVICE AND SYSTEM FOR TARGET SUBSTANCE DETECTION"; U.S. Provisional Application No. 62/277,854, filed Jan. 12, 2016, and titled "PORTABLE, HAND-HELD INSTRUMENT FOR DETECTION AND QUANTIFICATION OF CANNABINOIDS AND ALCOHOL IN EXHALED HUMAN BREATH"; and U.S. Provisional Application Nos. 62/508,864, filed May 19, 2017, and 62/514,618, filed Jun. 2, 2017, both of which are titled "SYSTEM AND METHOD FOR TARGET SUBSTANCE IDENTIFICATION."

EXAMPLES

The following examples provide additional contextual and supporting material relating to the subject matter of this disclosure. The information presented in these examples should be understood to in no way limit the generality of this disclosure.

Example 1: Immunoassay Method for Detecting THC

A summary of details about the materials and processes used in an example immunoassay method for detecting THC in breath samples is presented.

Materials

Primary (anti-THC antibody): There are two broad types of Antibodies used in Immunoassays—Polyclonals and Monoclonals. Polyclonal antibodies are more diverse and can detect a wider range of molecules. This makes them insensitive to minor changes to molecular structure, which can be important for a small molecule such as THC. Monoclonal antibodies are highly specific to the exact antigen. They are also more consistent from batch to batch since they mostly consist of one type of antibody. As a result, they can be produced by synthetic methods (e.g., Hybridomas).

For detection of THC from breath, either type of antibody can be used. Since breath samples are quite clean, especially after filtering out any saliva, molecular variants and other proteins which can bind to the anti-THC antibody are mostly absent. The selection of antibody for THC is mostly driven by practical considerations such as availability, lot-to-lot consistency, etc. A variety of suitable commercially available kits may be adapted for this use, including MaxSignal-THC-ELISA-Test-Kit or Cannabinoids ELISA Kit, available from mybiosource.com, or others available from fitxgerald-fii.com, novusbio.com and biossusa.com.

Antigen: Synthetic THC (Delta 8-, Delta 9-) or any of its variants (THCA, for example) can be directly adsorbed on to the surface for the antigen-down formats. THCA may offer some advantages over THC since it has a higher resistance to oxidation. The choice between Delta 8- or Delta 9- in conjunction with selection of antibody allows one to fine-tune the relative binding affinities between the antibody and the competitive antigen v/s antibody and the sample. THC/THCA can also be conjugated to a protein such as BSA to enhance strength of adsorption to the immobilization surface.

Reporter: For good sensitivity at low analyte concentrations, fluorescence and luminescence are the preferred signal generation schemes, since both methods offer good low-end sensitivity. Luminescence has the further advantage from a system perspective of not requiring an illumination source and spectral filters. Among luminescence reporters, Horseradish Peroxidase (HRP) and Alkaline Phosphatase (AP) are most commonly used. AP is a better candidate in formats where the total reporter concentration is low.

In a competitive assay, absolute concentrations of reporter enzyme are relatively high. In this case, HRP may be a better choice since it has much faster kinetics allowing for shorter assay times.

Assay Optimization

Clinical data can be used to define the optimal cut-off concentrations for THC detection. A primary goal of assay optimization is to maximize modulation (slope of the dose-response curve) at this desired cut-off concentration. In addition to selection of the different components (discussed above), the concentration of reagents can be optimized to maximize modulation. Two parameters to be optimized are (1) Ratio of analyte concentration in sample to the concentration of competitive antigen and (2) Ratio of concentration of competitive antigen to concentration of primary antibody.

For a qualitative assay with a defined cut-off concentration, when the competitive antigen and primary antibody concentrations are of the same order of magnitude (in Molar concentrations) as the cut-off concentration it results in the dose response curve having a maximum slope at the cut-off to maximize assay sensitivity and specificity.

Based on models, it is estimated that the maximum dose response is achieved by maintaining a primary antibody concentration which is in excess of the target analyte concentration, while keeping a molar ratio of close to unity for the competitive antigen and the primary antibody.

The optimization process involves varying concentrations of competitive antigen and primary antibody until a maximum is observed in the dose response curve at the cut-off concentration. Mathematical models can be used as a starting guess for these concentrations, which are fine-tuned by experimental data.

THC Immunoassay in a Flowcell

A flowcell may be used as the reaction geometry for the immunoassay. The flow cell will have an inlet and outlet port. A fluid manifold acts as the reservoir for all reagents, and directs fluid to and from both the flowcell and the breath collection module (BCM). The detector directly reads the final signal from the flow cell.

Miniature flowcells, having cross-sectional dimensions of about 100 μm—few millimeters, are a good platform for immunoassays. The small dimensions of the flow channel results in a high surface area to volume, which is favorable for surface reactions such as those in immunoassays. Custom flowcells may be fabricated to integrate with particular microfluidics architecture.

Prior to using the flowcell for a THC assay, the flowcell is coated with the surface moiety (antigen or anti-body depending on the format). In this example, an antigen-down format is assumed. The antigen is diluted to working concentration, and is flown into the flowcell, ensuring that the flow cell is completely filled. This is followed by incubation to ensure that the antigen is immobilized onto the surface. Any excess antigen is washed away by flowing a buffer solution through the flowcell multiple times. A blocking buffer is then introduced into the flowcell and incubated, to cover any bare surfaces which are not occupied by the antigen. This reduces non-specific binding and improves assay precision. The blocking step is particularly important in the flowcell geometry, due to the high surface area/volume ratio, which facilitates both specific and non-specific binding. The flow cell is finally washed and dried, and is ready for use.

Sample, diluted to an appropriate concentration, is introduced into the coated flow cell, and allowed to bind with the coated antigen. The rest of the assay process is like a standard microtiter plate assay. The volumes used in the flowcell may be considerably lower (about 10-50 uL) compared to what is used in a standard 96-well microtiter plate (about 100-200 uL).

The final signal is generated in the flow cell, which is read by a detector positioned either underneath or above it. The footprint of the complete device can be very small due to the small dimensions of the flowcell.

Assay and Process Optimization

Transitioning the assay from a standard microtiter plate to a flow cell may involve further optimization of reagents and processes. As briefly stated before, the blocking step can be important in ensuring that non-specific binding is minimized. Both the concentration and composition of the blocker might have to be modified to maximize dose response and minimize variability. The wash steps during the assay also enhance the performance of the assay. Wash parameters such as number of wash steps, composition of wash buffer, flow rates, residence times, etc. are all important to the performance. These steps may be optimized empirically.

Example 2: THC in Breath: Data from Development of a Marijuana Breathalyzer

THC is detected in breath for about 2-3 hours on average. Data on breath THC was collected after smoking indoors or outdoors, rather than in a laboratory setting. People have high levels of THC in their breath immediately after smoking. Breath THC drops to almost zero after 2-3 hours. Studies by the National Institute of Health (NIH) in 2013 and a European group in 2016 show a similar 2-3 hour time period. The 2-3 hours that THC is measured in breath correlates to the window of greatest impairment, as defined by NHTSA. The data were collected in 430 tests, more than all published studies combined. All samples were collected using a device developed by Hound Labs, Inc. and analyzed using mass spectrometry (MS).

Frequent smokers have virtually no THC in their breath if they have not smoked for several hours. Baseline breath THC in chronic smokers was found to be a maximum of 12 pg/5 L breath. A suitable breathalyzer can be calibrated so that very low THC levels will not trigger a positive test. This means frequent smokers—who often have substantial THC in their saliva, blood and urine long after the 2-3 hour window of impairment—do not have appreciable THC in breath after 2-3 hours and will not test positive on such an appropriately calibrated device.

The precise level of THC in breath is not important. Unlike alcohol, someone with a higher level of THC in breath is not necessarily "more stoned" than someone with a lower level. Environment plays an important role in THC breath levels. People who stay indoors after smoking have much higher levels than those who go outdoors—their peak levels may be 100 times higher. But breath THC levels drop substantially once they are outside, even though impairment is not affected by being outdoors versus indoors. A marijuana breathalyzer should be ultrasensitive so that it can accurately detect people who smoke outdoors, where levels often are very low during the 2-3 hour window of impairment.

People exposed to secondhand smoke will only have THC in their breath for a very brief time, and it disappears after a person is no longer exposed to this smoke. It is important that people exposed to second hand smoke be placed outdoors or in a well-ventilated area for 15 minutes before a breath test is performed. This is akin to alcohol testing, where the subject is observed for a minimum of 15 minutes so that alcohol in mouth vapors (which may dramatically elevate the level) dissipates before the breathalyzer is administered.

The science necessary to measure THC in breath is enormously complex. THC is measured in parts per trillion (picograms, pg), which means it is up to one billion times less prevalent in breath compared to alcohol. To put it another way, measuring THC in breath is like cutting a single raisin into 1 trillion pieces or finding one specific drop of water in 20 full sized Olympic swimming pools. The level of sensitivity required to measure THC is unprecedented.

POCTs

Disclosed herein are methods, devices, and systems to capture and analyze breath-borne analytes using noninvasive point of care testing (POCT), for example in medical treatment context or for self-administered testing for THC and/or alcohol impairment prior to engaging in activities for which impairment is contraindicated, such as driving. Embodiments for implementation may include functional elements (or modules) including breath capture, detection method, and chemistry modules, including noninvasive point of care testing devices and systems, particularly portable (e.g., handheld) such modules, devices and systems. The sample capture and analysis (e.g., measurement, determination and/or result reporting) can all be conducted noninvasively at the point of care, for example using portable, including handheld, devices and systems configured to capture and analyze the sample and provide the measurement/result at or near the time and place of sample collection.

According to various embodiments, the method involves capturing an exhaled breath sample from a subject at a location, such as a point of care for the subject, wherein the exhaled breath sample comprises aerosol droplets or particles, which are captured by impaction in a structure. In some embodiments, the structure may be in a disposable cartridge in a handheld device.

In some embodiments, the location is a point of care for the subject.

In some embodiments, the capturing of the aerosol droplets or particles by impaction involves capturing of the droplets through a plurality of impaction ports that are fluidically connected in parallel.

In some embodiments, the analysis for the analyte in the captured aerosol droplets is conducted using no more than a very small fluid volume, for example on the order of less than 100 µL, e.g., no more than 10 to 20 µL. In some embodiments, this may be accomplished by integrating the impaction sites directly into a microfluidic structure (e.g., a microfluidic circuit or plate) configured for analysis of the collected sample, such that droplet traps allow the collected samples to be eluted and transported within the microfluidic structure using a very small fluid volume.

Disclosed embodiments may also achieve capture, analysis (e.g., measurement, determination and/or reporting) of an analyte in the captured aerosol droplets at the point of care without any post-collection concentration operations.

Point of care testing (POCT), also referred to as bedside testing, is commonly defined as medical diagnostic testing performed at or near the time and place of patient care. POCT typically involves portable equipment and on-site sample collection and analysis. This may be contrasted with conventional medical diagnostic testing which is mostly confined to a medical laboratory, involving sending specimens away from the point of care to the laboratory and then waiting hours or days to learn the test results, during which time care would necessarily have to continue without the results. POCT is generally accomplished through the use of portable, including handheld, instruments, and can sometimes be conducted by patients themselves (e.g., at home) or by medical personnel whose primary training is not in the clinical laboratory sciences. Potential benefits include more rapid and effective decision making in hospital, clinical and home contexts, and improved safety.

Capture by impaction provides a versatile approach that is readily adaptable to the capture of analytes including THC in breath. Breath borne analytes have been found to exist primarily in a non-volatile state in aerosolized droplets formed in the deep lung. As a result, the capture target is aerosolized droplets that can be viewed as particles having a an aerodynamic behavior based almost entirely on their size and shape, rather than the particular chemical or other affinity properties of an analyte of interest, as would be the case for a volatile target species. Since the capture is primarily based on the size of the aerosol droplets in the exhaled breath sample, the capture device may be configured in the same or similar manner to capture virtually any analyte, by impaction. Then, the detection methodology may be tailored to the particular analyte(s) of interest in the aerosolized droplets captured by impaction, as further described below.

The described methods, devices and systems also have the merit of high yield capture of the component of an exhaled breath sample containing the analytes of interest, namely the aerosolized droplets originating in the deep lung. By contrast, alternative prior or potential methods of detecting breath-borne analytes have relied on affinity methodologies optimized for collection of volatile species in breath, or collection of breath condensate samples. Affinity-based collection techniques have low yield since breath borne analytes have been found to primarily be in non-volatile form and so with limited to no availability for affinity-based collection. Further, affinity-based collection of analytes requires very specific chemical or immunological targeting of the species to be collected, which limits the generality of the approach. Breath condensate collection, on the other hand, while general, lacks the specificity of capture by impaction and so provides a sample this is much less concentrated in and focused on the analytes of interest. This is a substantial impediment when attempting to meaningfully and reliably detect and measure very small quantities of analyte, such as exist in breath.

Described methods, devices and systems have the merits of sample capture by impaction and/or in a point of care format.

In one embodiment of this disclosure, a method includes capturing an exhaled breath sample from a subject, wherein the exhaled breath sample comprises aerosol droplets or particles that are captured by impaction, measuring an amount of an analyte in the captured aerosol droplets or particles, the analyte associated with existence of THC or a metabolite in the subject, and determining, based on the measurement, ingestion of THC by the subject within a reference timeframe. The sample capture, measurement, and determination can all be conducted at the point of care, for example using portable devices and systems configured to capture and analyze the sample and provide the measurement/result at or near the time and place of sample collection.

Thus in another embodiment of this disclosure, a POCT method includes non-invasively capturing a biological sample from a subject, measuring an amount of a target analyte in the captured biological sample, the target analyte associated with existence of a physiological condition in the subject, measuring an amount of a reference analyte in the captured biological sample, the reference analyte known to exist at a stable concentration in the subject, and determining, based on the measurements, the existence of the physiological condition in the subject, wherein the sample capture, measurement, and determination are conducted at the point of care. The biological sample may be an exhaled breath sample comprising aerosol droplets comprising the target and reference analytes, and the aerosol droplets may be captured by impaction.

Where the determining includes comparing the target analyte and reference analyte amounts, the concentrations of those analytes may be measured to determine a concentration ratio.

In further embodiments, a POCT method includes measuring an amount of a target analyte in ambient air in proximity to a location of the subject and a time of obtaining a breath sample from the subject (e.g., at the point of care). Thus, the determining can further includes comparing the target analyte and reference analyte amounts with a background level amount of the target analyte and/or reference analyte in ambient air.

In some embodiments, measuring an amount of a target analyte in the captured biological sample may include measuring a plurality of target analytes associated with existence of a plurality of physiological conditions in the subject, and the determining may include determining the existence of any of the plurality of physiological conditions in the subject.

In some embodiments, the reference analyte may be known to exist at a stable concentration in the subject regardless of the existence of the physiological condition in the subject.

In some embodiments, the reference analyte may be known to exist at at least a minimum concentration in the subject. Non-limiting reference analytes include In some embodiments, the biological sample is an exhaled breath sample comprising aerosol droplets comprising the target and reference analytes, and the aerosol droplets are captured by impaction.

In some embodiments, the target analyte is any described herein.

In some embodiments, the measuring is conducted using one or more of a chemiluminescence assay, an immunoassay, an enzymatic assay, and by electrochemical detection.

In some embodiments, the sample capture, measurement and determination are all conducted with a portable point of care device.

In other embodiments, a device in accordance with this disclosure includes a sample capture module configured for capture of an exhaled breath sample from a subject and an ambient air sample, wherein the exhaled breath sample comprises aerosol droplets and the aerosol droplets are captured by impaction, and a sample component analysis module configured for measuring an amount of a target analyte in the captured aerosol droplets, the target analyte associated with existence of THC or a metabolite in the subject, and determining, based on the measurement, ingestion of THC by the subject within a reference timeframe. The sample capture and analysis modules may be comprised in a portable point of care device.

In one implementation of this embodiment, the device is further configured to measure an amount of a reference analyte in the captured aerosol droplets, the reference analyte known to exist at a stable concentration in the subject, and the determining involves a comparison of the target analyte measurement and the reference analyte measurement.

In one implementation of this embodiment, a device includes a sample capture module configured for non-invasive capture of a biological sample from a subject, a sample component analysis module configured for measuring an amount of a target analyte in the captured biological sample, the target analyte associated with existence of a physiological condition in the subject and for measuring an amount of a reference analyte in the captured biological sample, the reference analyte known to exist at a stable concentration in the subject, and for determining, based on the measurements, the existence of the physiological condition in the subject. The sample capture and analysis modules may be comprised in a portable point of care device.

In other embodiments, a system in accordance with this disclosure includes, a point of care device, the device including, a sample capture module configured for capture of an exhaled breath sample from a subject, wherein the exhaled breath sample comprises aerosol droplets and the aerosol droplets are captured by impaction, and a sample component analysis module configured for measuring an amount of an analyte in the captured aerosol droplets, the analyte associated with THC or a metabolite in the subject, and determining, based on the measurement, ingestion of THC by the subject within a reference timeframe. The sample capture and analysis modules may comprised in a portable point of care device, the point of care device operating to: capture an exhaled breath sample from a subject, wherein the exhaled breath sample comprises aerosol droplets and the aerosol droplets are captured by impaction, measure an amount of an analyte in the captured aerosol droplets, the analyte associated with existence of THC or a metabolite in the subject, and determining, based on the measurement, ingestion of THC by the subject within a reference timeframe. The sample capture, measurement and determination may be conducted at the point of care.

In one implementation of this embodiment, the system device is further configured to measure an amount of a reference analyte in the captured aerosol droplets, the reference analyte known to exist at a stable concentration in the subject, and the determining involves a comparison of the target analyte measurement and the reference analyte measurement.

In one implementation of this embodiment, a system device includes a sample capture module configured for non-invasive capture of a biological sample from a subject, a sample component analysis module configured for measuring an amount of a target analyte in the captured biological sample, the target analyte associated with existence of a physiological condition in the subject and for measuring an amount of a reference analyte in the captured biological sample, the reference analyte known to exist at a stable concentration in the subject, and for determining, based on the measurements, the existence of the physiological condition in the subject. The sample capture and analysis modules may be comprised in a portable point of care device.

Details for implementation of some embodiments of the described methods, devices and systems follow. One of the challenges encountered when attempting to perform analyte detection in breath samples is that many analytes are present in very small quantities in a typical exhaled lung volume (as noted earlier with respect to THC). In view of this, an efficient and effective capture mechanism for obtaining breath samples, e.g., a breath capture module (or, alternatively, breath collection module) may be used to collect breath samples that can then be analyzed using any of the techniques discussed herein.

Design of a breath capture module (BCM) begins with considerations on source and form of the target analyte in breath. With the exception of volatile small molecules, all other small molecules and macromolecules are present in breath encapsulated in aerosolized liquid drops in the range of about 0.5-10 μm. The composition of the liquid drops consists primarily of water with other macromolecules associated with the respiratory tract.

For aerosolized liquid droplet targets, a mechanism of capture based on inertial impaction may be particularly effective, and a BCM may be designed with channels incorporating turns and bends to facilitate droplet capture through inertial impaction, as will be discussed in more detail below. A two-stage mechanical filtering system may be used in some implementations to help screen out droplets that are larger and/or smaller than a desired size range of droplets. For example, a saliva trap, such as saliva traps used with blood alcohol sensors, may be placed upstream of an inertial impaction droplet trap to filter out droplets that are larger than the upper end of the desired size range, e.g., larger than 100 μm, and the inertial impaction droplet trap may then be used to filter out those smaller droplets that pass through the saliva trap but are larger than the lower end of the desired size range, e.g., larger than 0.1 μm. The droplets that are captured by the inertial impaction droplet trap may generally be of the desired size range and may then, for example, be eluted out of the inertial impaction trap in order to be conveyed to a downstream analysis system or may, in some implementations, simply be analyzed in-situ. Example inertial impaction droplet traps are discussed in more detail later below.

In addition to the channel geometry, substrate material used for the fabrication of BCMs may be selected, in some implementations, based on the properties of the target of interest. For molecular capture, the substrate material may be chosen such that the target has an affinity for the surface of the material and is immobilized on that surface after contact. The material may also facilitate release of the target into solution during elution or assay steps. Generally, the material may be weakly hydrophilic for a hydrophilic target and weakly hydrophobic for a lipophilic target.

However, for various non-volatile aerosolized species discussed in this disclosure, the BCM material may be designed to capture liquid drops, the primary constituent of which is water. For hydrophilic targets, a weakly hydrophilic substrate will enable retention of liquid drops during capture while facilitating release of these drops during elution or reaction steps. For hydrophobic targets, a strongly hydrophilic surface will discourage the target from adhering to the surface during elution or reaction steps. Macromolecules, particularly large proteins, are amphiphilic, which means they consist of both hydrophobic and hydrophilic regions. A hydrophilic capture material is appropriate for these molecules as well.

In addition to surface characteristics, e.g., hydrophobicity or hydrophilicity of the material used for the sample collection sites of the BCM, analysis systems that interface with the BCM may be designed to facilitate efficient retrieval of collected samples, e.g., through use of properly selected eluents, e.g., elution buffers.

Typical captured droplets from exhaled breath may include a high percentage (>50% by mass) of surfactants such as phospholipids, such as DPPC (dipalmitoyl phosphatidylcholine). These surfactants may include long-chain aliphatic carboxylic acids which render them highly lipophilic. When aerosol droplets are captured on a surface, due to the extremely low volumes (pL or less) of droplets, the water contained in these droplets can evaporate very quickly (especially considering the flow of exhaled air that flows past them during droplet capture), resulting in a concentrated patch or "scab" of lipophilic surfactants on the surface(s) of the capture sites in the BCM. It is within these "scabs" that the analytes of interest may be trapped. The challenge with elution is to then encourage dissolution of the phospholipids in order to release the species of interest into solution for subsequent transport, reaction, and/or analysis.

As discussed above, surface modifications, e.g., surface treatments to render the surfaces on which the "scabs" form more or less hydrophilic or hydrophobic, may be used to increase or enhance the recovery of collected sample material.

Surface modification may be used to create a surface which prevents phospholipids from forming a "scab" on the surface of the BCM (or at least from forming a "scab" that is strongly adhered to that surface). Potential modifications include coating the surface with polymers such as tri-block copolymers containing repeating ethylene oxide and propylene oxide groups or biological macromolecules such as proteins (examples include BSA, casein, etc.). In these two cases, the mechanism of deposition of the surface treatment may be physical adsorption, wherein the coating agent is allowed to incubate with, for example, a bare plastic surface of a BCM, and the agent is allowed to adsorb onto the surface, forming a barrier. Alternately, the surface can be treated chemically to impart specific functionality. Silanizing is one such method of surface treatment. In this process, a silanizing agent such as trichloro silanol may be allowed to react with the plastic surface (or alternately air) to form a silanized coating on the surface. The silanized coating creates a barrier between the phospholipids and the bare plastic surface. Such coatings reduce the energy needed to decouple the collected sample from the BCM surfaces and place the constituents thereof into solution.

In some cases, the analyte may be present in alveolar lining fluid (ALF) which is present in exhaled breath as aerosolized droplets, for which a BCM geometry based on inertial impaction can produce high capture efficiency. A hydrophilic material may be used for capturing these droplets in order to facilitate re-suspension of these droplets during subsequent elution/reaction steps. Suitable materials for such a BCM may include Polystyrene, PETG, Glass, etc. A BCM with a hydrophilic material (treated polystyrene, PETG, glass, etc.) in a geometry designed for inertial impaction may provide good capture of droplets/particles of interest.

Another mechanism that may be used, alternatively or additionally to surface modification, involves selecting appropriate elution solvents targeted to solubilize the phospholipid "scab" and release the species of interest into solution. Addition of surfactants such as polysorbate 20 (such as Tween 20) or Triton (offered by Dow Chemical Company) in the range of 0.1-1% by mass can assist in solubilizing phospholipids dried on the surface of the BCM.

In addition to surfactants, other agents which may be alternatively or additionally used to solubilize phospholipids may also be added to improve elution efficiency. Of particular interest are a class of bile acid salts—sodium salts of cholic acid and deoxycholic acid, which have a biological function of digesting cellular membranes and are hence very effective in solubilizing phospholipids. Typical concentrations of these bile salts range between 0.1-1%. These bile salts can also be used in combination with other surfactants for potentially synergistic effects.

Phospholipases, a class of enzymes which are specific to digesting phospholipids, may also be used to solubilize DPPC and release the analyte of interest into solution. Phospholipases A, B, C, and D act on different regions of the phospholipid molecule. A combination of these enzymes in concentrations of 0.01-0.5 IU/mL may be used in the elution buffer in some implementations.

The pH of the elution buffer may also contribute to solubilization of the analyte of interest. For example, THC has higher solubility at pH>8, in which case the elution buffer used for THC collection may be selected to have a high pH, e.g., >8. Buffers such as MOPS, carbonate, borate, Tris, etc. can be adjusted to a pH between 8-10 and may thus be suitable for such usage. The higher pH may be combined with other strategies described above to maximize solubilization of target analyte.

A BCM for capture aerosol drops via inertial impaction may be designed, according to the principles and concepts outlined herein, to intercept aerosol particles >0.7 μm, for example, and retain them on the walls of a channel through which breath is flowed while the BCM is used to collect a breath sample. Multiple impaction sites may be incorporated into the BCM to provide for parallel capture of droplets, thereby allowing for higher droplet capture efficiency and greater breath throughput.

In addition to flow considerations, a handheld BCM design may, in some instances, also facilitate specific breathing profiles such as rapid inhalation, rapid exhalation, coughing, etc. to stimulate production of volatiles or aerosol drops from appropriate regions of the respiratory tract. This can be accomplished, for example, using sensors such as pressure, flow rate, and CO2 sensors to monitor breath sample collection.

Detection Method

Any appropriate assay or sensor, including immunoassays, chemical assays, enzymatic assays, electrochemical detection/sensors, etc., may be used to detect and quantify the analyte(s) sought. In various embodiments, in order achieve picogram sensitivity the measuring/determining aspect of the method may involve an immunoassay. Suitable immunoassays may include surface-based antibody-down immunoassays, surface-based antigen-down immunoassays, noncompetitive immunoassays, heterogeneous competitive immunoassays, and homogeneous competitive immunoassays. Several suitable immunoassays were described with reference to FIGS. 5-9, above. The operation of these immunoassays and their generalization to other recognition elements and analytes will be well understood, and implementation details for suitable immunoassays will be readily ascertained, by those of ordinary skill in the art. Such immunoassays, and others such as enzymatic assays or electrochemical sensors such as are referenced below, are readily adaptable by those of ordinary skill in the art to a full range of analytes such as described herein using well-known and readily available chemistry and techniques, given the disclosure provided herein.

In an enzymatic assay, the analyte of interest is either a substrate or co-factor for a specific enzyme resulting in a chemical reaction which generates signal. The progress of the enzymatic reaction can be tracked by either optical (absorbance, fluorescence, chemiluminescence) or electrical (potentiometry, amperometry) methods. For example, glucose can be assayed by the conversion of glucose into gluconic acid and hydrogen peroxide by the enzyme glucose oxidase. Detection methods involve either detecting the formation of hydrogen peroxide or gluconic acid by a secondary reaction or via change in electric potential.

Moreover, in some embodiments, the concept of using a normalizing measurand (NM) can be used to facilitate quantitative measurement of analyte concentrations in lung fluid using described methods, devices and systems. The reportable for these analytes is a concentration based on mass per unit volume of lung fluid (also known as Alveolar Lining Fluid —ALF). ALF is found in the deep lung and its composition is in equilibrium with blood. Exhaled breath samples carrying aerosolized droplets of ALF are collected at the impaction site on the BCM. Due to the nature of exhaled breath, the volume of ALF per unit volume of breath can be inconsistent, even for the same subject across multiple samples. So, a substantial challenge for quantifying an analyte of interest may be in determining the total volume of ALF collected.

This disclosure provides a solution to this challenge by, in some embodiments, quantifying the mass of another reference analyte, the concentration of which is constant across multiple samples and subjects. The analyte concentration of interest can then be represented as a ratio of mass of analyte to mass of this standard, or reference, analyte (which is also called the normalizing measurand—NM). Examples of a NM include: sodium ion, potassium ion, chloride ion, total protein, albumin, total ionic strength, conductivity, pH, etc.

After collection of a breath sample, an elution solvent is introduced into the BCM to solubilize all components. After elution, there are multiple approaches to measuring the mass of both the analyte of interest and the NM, for example:

i. Eluent is split into two channels, one for the analyte and one for NM; and
ii. Eluent consists of two separate recognition molecules (e.g., antibodies), one specific to the analyte and one for NM. The recognition molecules can have different labels (e.g., two different fluorophores), allowing for quantification of both markers in the same channel.

A specific example of this embodiment is to measure concentration of glucose in ALF. For this, an example NM is Na+ ion. For this application, the eluent can be directed to an electrochemical sensor chip, with specific locations to detect Na+ via potentiometry and glucose via enzyme-assisted amperometry. The ratio of the two analytes is used as the reportable to monitor variations in ALF glucose concentrations.

The choice of a particular detection method may be driven by limit of detection (LOD) requirements of the target analyte and relative complexity of disposable and durable design. The most common method of utilizing a binder to detect and quantify a target analyte is implemented using an immunoassay. For large macromolecules with multiple binding sites, a sandwich-format immunoassay with a capture binder and a detection binder may be used to detect and quantify low concentrations (e.g., 10-100 μg/mL) of the target analyte. Readout or interrogation mechanisms to perform such detection and/or quantification may be based on absorbance, fluorescence, or chemiluminescence. Chemiluminescence-based readout often gives the lowest LOD. For small molecules with only a single binding site, a competitive immunoassay format can be used, based on relative binding of the target and a competing molecule. For both sandwich and competitive formats, "no-wash" modifications such as LOCI are also possible options.

In addition to optical-readout methods as discussed above, there are electrical readout methods, such as are described in Impedimetric Immunosensors-A Review, M. Prodromidis, Electrochimica Acta, Vol. 55, Issue 14, Pg. 4227, which is hereby incorporated by reference herein in its entirety. Both sandwich and competitive formats may be coupled with an electrochemical readout. For sandwich assays, the capture binder may be immobilized on the electrode. Sample and detection binder are brought to the electrode site. A sandwich construct of capture-analyte-detector is formed at the electrode surface. The presence of this large molecular construct is detected using impedance spectroscopy, where impedance is measured as a function of frequency. The molecular construct results in a signature impedance frequency profile. The magnitude of this profile is proportional to the surface concentration of the molecular construct which is in turn proportional to the concentration of the target analyte in sample. For a competitive format, the competing antigen is immobilized on the surface with the binder bound to it. When the sample is introduced to the electrode site, the binder dislodges from the surface antigen and binds to target analyte in solution. The number of binder molecules getting dislodged from the electrode surface is proportional to the concentration of target in solution. The dislodged binder causes a change to the impedance spectrum which is measured as the signal.

Choice of detection method affects design of both disposable and durable components. A laminate for conducting detection may be designed around the process steps for the assay based on the detection method. Details such as the number of liquid lines, sequencing of different reagents, mixing, etc. are considerations for designing layout of the laminate. The molded shell design may be based on number of discrete liquid reagents and process details of the assay.

Base station components may be determined by the readout mechanism. For optical readouts as in traditional immunoassays, the base station may be equipped with an optical detector with the appropriate sensitivity and noise characteristics, and a light source for absorbance and fluorescence readouts. For electrical readouts, the base station may be equipped with hardware to measure frequency-dependent impedance.

Typical detection ranges using absorbance readout are in the range of 10-1000 µg/mL. Since typical levels in breath samples are expected to be significantly (100-1000×) lower than in blood, a sensitive chemiluminescence assay or impedance-spectroscopy based method is expected to be required.

As noted above, any appropriate assay or sensor (including immunoassays, chemical assays, enzymatic assays, electrochemical detection, etc.) may be used to detect and quantify the analyte(s) sought. In other implementations, quantification of other analytes may be used to improve measurement or quantification of an analyte of interest. For example, measurement of the amount of phospholipids in a sample may be performed in order to normalize a measurement of THC in the same sample to produce a THC/phospholipid ratio measurement, which may be a more useful metric of potential THC presence in the test subject than a THC/liters of breath sampled metric.

Chemistry

The target-specific binders are fundamental reagent components. The selection and optimization of these binders is fundamental to the immunoassay method and is a well-established area. Once selected, the same binders can be used in all formats as discussed above in relation to THC. In addition to binders, other constituents such as buffers, wash solutions, diluents, detection substrate, etc. are used based on the assay format. The selection of these components may also impact the design of the laminate and molded shell components.

In some embodiments, the aerosol drops may be captured by a device configured for impact and capture of aerosol drops forcefully exhaled into the device, as further described below.

Generally speaking, BCMs for droplet capture may feature, as discussed above, turns and bends to facilitate the capture of droplets of particular size ranges. In the context of a largely planar structure or substrate, such as a microfluidic plate that may be suitable for analyzing collected samples having very small volumes, one particular type of droplet trap may utilize a plurality of small impaction ports that are positioned on an outer major surface (e.g., one of the larger, flat surfaces) of the planar structure and are in fluidic communication with a plenum volume that is adjacent to, and partially defined by, that outer surface-such a plenum volume may, for example, include a portion of a housing or valve structure that is adapted to interface with, for example, a mouthpiece or saliva trap, such as is discussed earlier herein. In practice, a test subject (person) may place their lips around the mouthpiece or saliva trap to form a generally airtight seal, and may then exhale therethrough and into the plenum volume. The plenum volume may then serve to distribute the air from a person's exhaled breath to the plurality of small impaction ports. Each impaction port may overlap with an elution channel located within the planar structure and be in fluidic communication therewith, i.e., the impaction ports may be fluidically interposed between the elution channel and the plenum volume.

Generally speaking, sample droplets that are captured by a droplet trap are typically post-processed after capture to allow the analyte samples within them to be resuspended in a solution for conveyance from the droplet trap to downstream functional components, e.g., optical interrogation cells, mixing chambers, etc., or to allow for mixing with one or more reactants or other labeling mechanisms. Post-processing can be performed by flowing an eluent, such as one of the eluents discussed elsewhere in this disclosure, through an elution passage. During sample collection (a breath sample or an ambient air sample), the elution passage may be kept free of eluent (or other liquid) to allow for free flow of the sample (exhaled breath or ambient air) through the elution passage. Once the desired droplet sample has been captured, then the liquid eluent may be flowed into the eluent passage in order to elute the captured droplets (or the analyte-containing "scab" left behind after the water in a captured droplet or droplets evaporates). Such eluent may be flowed into the eluent passage via a passage inlet port.

Figure 11:
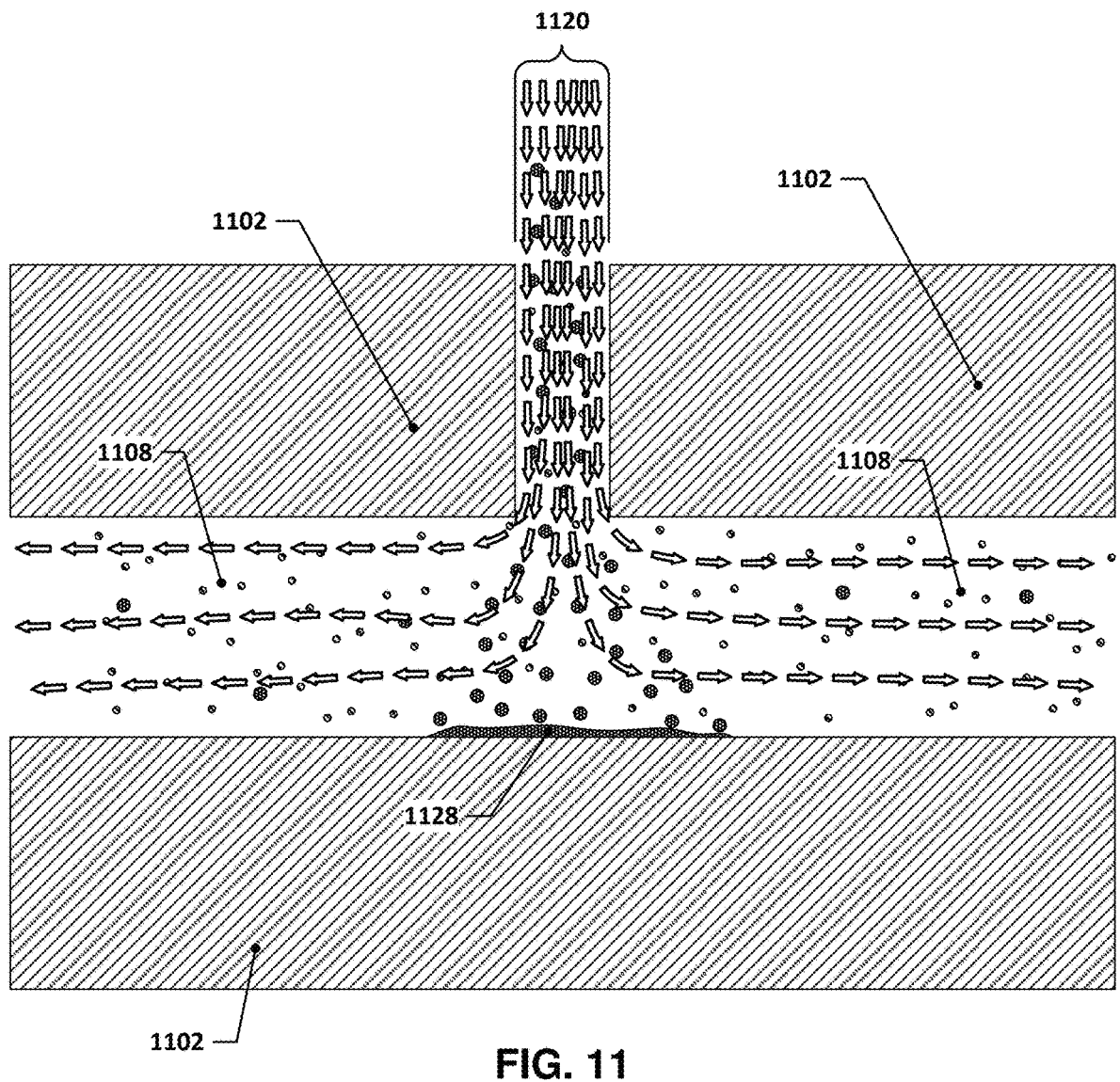
FIG. 11 depicts a cross-section view of a portion of a droplet trap.
Figure 12:
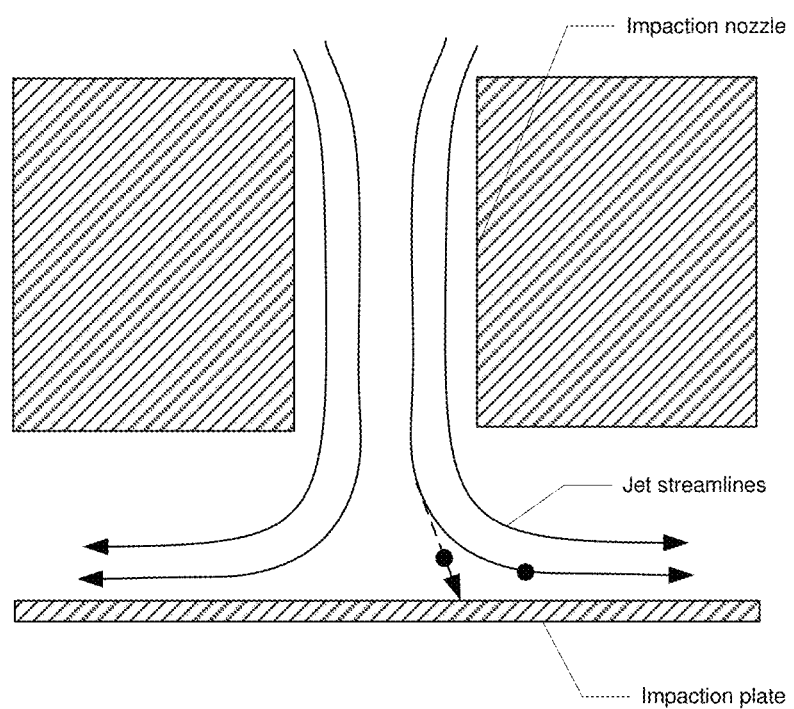
FIG. 12 shows a cross-sectional diagram of an inertial impaction BCM collection site.
Figure 13:
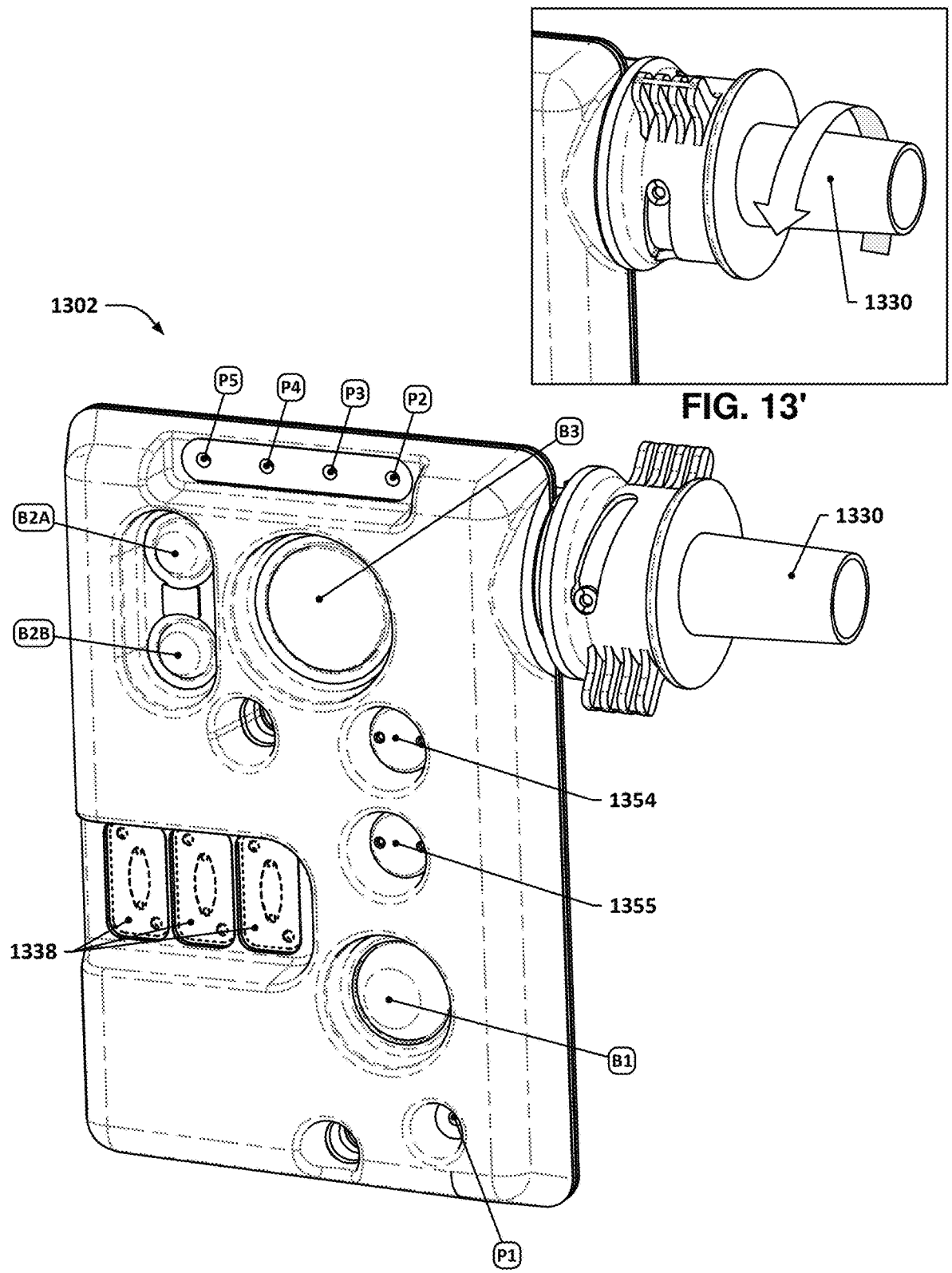
FIG. 13 depicts a perspective view of an exterior of another example cartridge.
Figure 14:
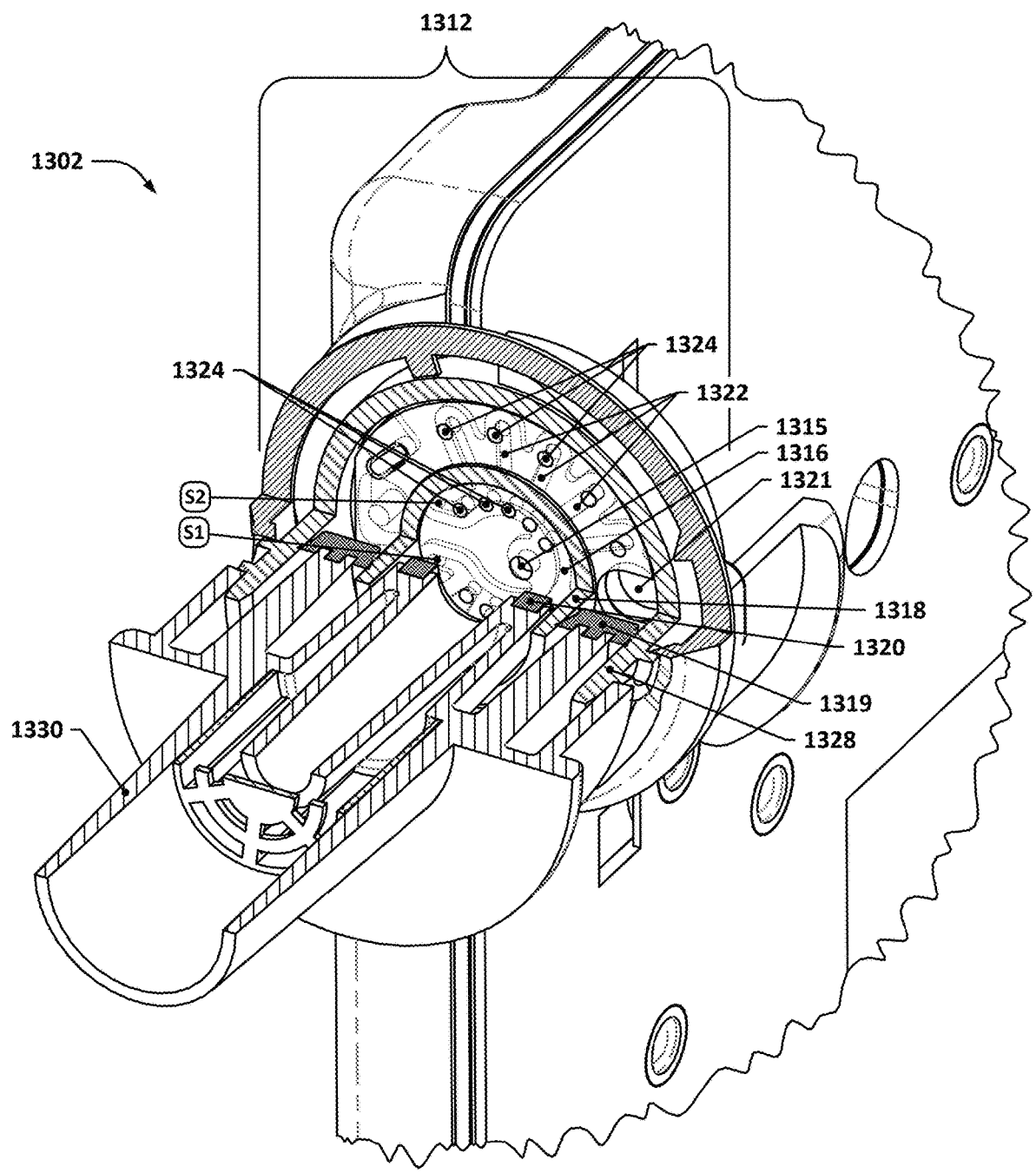
FIG. 14 depicts a detail cutaway view of the mouthpiece/BCM of the example cartridge of FIG. 13.

FIG. 11 depicts a cross-section view of a portion of a droplet trap. As can be seen, the impaction port 1120 extends through a substrate 1102 and intersects with the elution passage 1108. A sample that flows through the impaction port 1120 may enter the elution passage 1108 and then make a 90° turn (arrows are added to indicate the general flow directions of the sample). Particles suspended in the sample, e.g., droplets or particles, may experience varying degrees of success in navigating this turn depending on the sharpness of the turn, the flow rate of the sample, and the size and mass of the droplets (the size and mass of the droplets will generally be directed related, as the droplets will tend to be spherical in nature and have similar densities). Larger, heavier droplets will have greater inertia than smaller, lighter droplets and will be more resistant to external forces encouraging them to change direction, i.e., turn the corner.

Smaller particles (droplets), indicated by smaller-sized circles with lighter shading, in the sample flow may successfully navigate the 90° turn, whereas larger particles/droplets, indicated by larger-sized circles with darker shading, will generally not be able to make the 90° turn and will impact the floor of the elution passage 1108 and adsorb onto it, forming a trapped portion of sample 1128.

One key issue with capturing droplet samples from breath samples or ambient air sample is that a very large volume, relatively speaking, of the breath/air sample, e.g., several liters, must be flowed through the droplet trap in order to capture a quantity of droplets that is sufficiently large enough to allow for a measurable quantity of the analyte that is of interest to be obtained. At the same time, it is simultaneously desirable to reduce the collected sample volume so that the concentration of the analyte in the working volume of the analysis system is increased, e.g., concentrated into a working volume on the order of 10 to 100 μL, e.g., ~10 μL, ~15 μL, ~20 μL, ~25 μL, ~30 μL, ~35 μL, ~40 μL, ~45 μL, ~50 μL, ~55 μL, ~60 μL, ~65 μL, ~70 μL, ~75 μL, ~80 μL, ~85 μL, ~90 μL, ~95 μL, or ~100 μL. In order to facilitate such concentrated sample capture, the droplet trap can use multiple impaction ports 1120, e.g., 10 ports, that are spaced apart from one another along the elution passage 1108 and that are each supplied air from the plenum volume in parallel.

Such configurations greatly increase the feasibility of providing a POCT system that is able to process breath samples and/or ambient air samples. By integrating the impaction sites directly into the microfluidic circuit, such droplet traps allow the collected samples to be eluted and transported within the microfluidic circuit using a very small fluid volume. In comparison, droplet traps that are not integrated into such microfluidic circuits generally require that much larger fluid volumes be used. For example, if an analysis system were to use a different design of droplet trap that was entirely separate from the analysis instrument (or portions thereof), it would likely be the case that a significantly larger amount of fluid would need to be used in order to a) elute the collected sample from such a droplet trap and b) convey the eluted sample to the analysis instrument for analysis. For example, there would likely need to be flow paths between such a droplet trap and the analysis instrument, and extra fluid would likely be needed to drive the eluted sample through such flow paths; the eluted sample would likely at least partially disperse throughout such a fluid volume, and the extra fluid would thus act to further dilute the concentration of the collected sample within the fluid volume. Such dilution, in turn, may cause the signals produced by whatever analysis is performed to be attenuated, reducing the sensitivity of the analysis and the accuracy of the result.

Moreover, the incorporation of the droplet trap into a microfluidic plate allows for very small working volumes to be used for sample elution, as discussed earlier. For example, such droplet traps may use working volumes on the order of 10 μL to 20 μL, which may, in many implementations, allow for the collected samples to be analyzed without performing additional separation or concentration operations. For example, in systems that use larger working volumes, e.g., milliliters or centiliters, of working fluid to elute a similar quantity of collected samples from breath or ambient air, the collected samples from breath may be diluted to a much greater extent, e.g., the concentration may be two or three orders of magnitude more dilute than with working fluid volumes in the tens of microliters or smaller range.

In systems that may use such larger working volumes, the resulting sample dilution will make it much more difficult, or impossible, to obtain accurate measurements of an analyte of interest contained within the collected sample. For example, if an assay is used that relies on a chemiluminescent intensity that is tied to the concentration of the analyte in the working fluid/collected sample mixture, such an intensity may be orders of magnitude lower per unit volume of collected sample/working fluid than it would be at higher concentrations of concentrations of the analyte in the working fluid/collected sample mixture. Such reduced chemiluminescent intensity would generally require the use of a more sensitive, and thus generally more expensive, optical detector, and would also tend to decrease the signal-to-noise ratio of the detected optical signal.

In order to improve the concentration of the collected sample in such larger-working volume systems, such equipment may include various systems that may be used to, in some way, decrease the amount of working fluid present without corresponding decreasing the amount of collected sample mixed therewith (thereby raising the concentration of the sample in the remaining working fluid). For example, post-collection concentration techniques such as centrifugal separation, gravity separation, and/or evaporative separation may potentially be used to remove the working fluid while potentially leaving most or all of the sample behind, thereby increasing the concentration of the collected sample (and analyte(s) of interest) in the remaining working fluid. Performing these techniques, however, requires additional mechanical and/or electrical equipment, increases complexity, and requires additional time, all of which increases the cost of the device and/or the time required to obtain and analyze a sample.

By integrating the droplet trap directly into a microfluidic circuit used in analysis of the samples collected using the droplet trap, the droplet traps discussed herein provide a higher concentration of collected sample within the working fluid used to elute the sample from the trap post-collection without requiring the additional complexity and cost of post-collection concentration systems.

While the above discussion has provided a detailed overview of one particular droplet trap using inertial impaction, various other droplet traps are also considered within the scope of this disclosure. Additionally, other types of sample collectors, such as those based on diffusion (discussed earlier herein), may be used if the biomarker or analyte being sought is a volatile specie.

Inertial impaction droplet traps, however, may be particularly well suited for capturing samples of non-volatile species, which may be carried in aerosolized droplets that originate from the deep lung area and are carried by aerosol drops generated in the deep lung. The current understanding is that aerosol drops are generated via a film-burst mechanism in the deep lung during the inhalation cycle; species which are present in the deep lung are incorporated into aerosol drops during this process. The aerosol drops are then carried into the breath stream during exhalation. In addition to the deep lung, aerosol drops can also be generated in the upper airways and oral cavity. The mechanism for creation of aerosol drops in these regions is typically during activities such as talking, coughing, laughing, etc. The distribution of droplet sizes generated by these activities is different, and thus droplet size may be used as a general proxy for the origination point of individual droplets (and thus the species contained within them).

In contrast to capturing volatile species, design of a BCM for capture of non-volatile species is agnostic to properties of the species itself, but can be dependent on the distribution of aerosol drops which carry the species of interest. Qualitatively, in the absence of other considerations, one can anticipate that the designs for inertial impaction BCMs to capture these distributions will be different.

Before diving into the design of BCMs for a particular distribution of aerosol droplets, it is useful to describe the basic mechanism of how aerosol droplets can be captured by inertial impaction. This technique involves driving a steam of fluid (in this case, air from a breath sample) containing the droplets or particles of interest towards a stationary surface. When the gas streamlines encounter the stationary surface, they turn parallel to the surface (see FIG. 12). The aerosol or particle droplets, however, have a higher inertia due to their higher densities, and are unable to make the turn necessary to stay with the gas/jet streamlines. As a result, they impact the stationary surface (impaction plate in FIG. 12), where they adsorb onto the stationary surface and are captured.

The process of inertial impaction is characterized by a universal dimensionless number called the Stokes' number (St), given by:

$$St=\rho_p d_p^2 v/9\ \mu D$$

where $\rho_p$ is the density of the aerosol droplet or particle, $d_p$ is the diameter of the aerosol droplet, v is the linear velocity of the air stream through the impaction nozzle/port perpendicular to the impaction surface, $\mu$ is the viscosity of the gas stream and D is the hydraulic diameter of the impaction nozzle/port.

For a given Stokes number, there is a capture efficiency (11) which represents the probability or fraction of particles with the particular Stokes number, that will be captured by the impaction surface. A characteristic property of the relationship between capture efficiency and St is a sharp transition between low and high capture efficiencies. This allows for inertial impaction to act as a binary collector, with very low capture efficiency for St numbers below a certain value and very high capture efficiencies for St above a certain threshold value. If we keep all other parameters fixed except for $d_p$ in the expression for St, the Stokes number St is only a function of the aerosol or particle size, $d_p$. For different values of $d_p$, we obtain different St values, which translates to a particular capture efficiency. Because of the sharp transition in capture efficiency as a function of St, there is a sharp transition in capture efficiency as a function of particle size, or $d_p$. The sharp-transition occurs around a particle size called as the cut-off diameter. An inertial impactor may thus act as a sieve, trapping all droplets above the cut-off diameter, and allowing smaller droplets to pass through completely.

BCMs designed for inertial impaction may utilize this strong relationship between St and capture efficiency. Based on this "sieve" property, the trivial solution is to design the BCM to capture the smallest droplet size desired, but as it will be seen in paragraphs ahead, there are practical limitations, and there is a trade-off between cut-off size and other parameters.

Another example of a cartridge format and analysis system that may be used to obtain and analyze breath samples for THC is discussed below, which depict various views of an example cartridge, or portions thereof, for performing THC detection and quantification in human breath. FIG. 13 depicts a perspective view of an exterior of the cartridge. FIG. 13' depicts a supplemental view showing the mouthpiece of the cartridge in a twisted, locked configuration. FIG. 14 depicts a detail cutaway view of the mouthpiece/BCM.

As can be seen in FIGS. 13 and 13', the cartridge 1302 may include a housing 1306 that contains a variety of components and interfaces that allow the cartridge to be interfaced with various systems, e.g., a base station and/or a handheld unit. For example, the cartridge 1302 may have optical windows 1338 that allow for an external device, e.g., an optical measurement unit, to optically interrogate or image fluidic samples that are housed within optical measurement chambers within the cartridge 1302. The cartridge 1302 may also have various burstable blisters B1, B2A, B2B, and B3 that may be able to be compressed (and eventually burst) through application of force to the externally accessible portions thereof. The cartridge 1302 may also have a plurality of vent ports P1-P5 that are able to be interfaced with various fluidic ports on, for example, a base station in order to allow positively pressurized air or a vacuum to be applied to various internal flow paths within the cartridge 1302, or to fluidically connect such flow paths to the ambient environment, e.g., to air at atmospheric pressure. The cartridge 1302 may also include an evidence cap 1354 that may be removable to access an evidence chamber within the cartridge 1302 that may be used to store a portion of sample for a prolonged period of time. Similar to an evidence cap, the cartridge 1302 may also include an ambient air cap 1355 that may be removable to access an ambient air chamber within the cartridge 1302 that may be used to store a portion of an ambient air sample for a prolonged period of time The cartridge 1302 may also have a mouthpiece 1330 (or an interface for receiving a mouthpiece) that is able to be rotated, e.g., as shown in FIG. 13', to as to cause the mouthpiece to rotate about an axis and simultaneously translate along the axis, e.g., due to the use of a sloped bayonet-style mechanical feature (as shown).

The mouthpiece 1330 may be connected with a mouthpiece interface 1328 and may include various features that interface with a breath collection module that facilitates breath sample collection, e.g., similar to the inertial-impaction-based BCMs discussed earlier herein. FIG. 14 depicts a partial cutaway detail view of the mouthpiece 1330 and mouthpiece interface 1328, as well as portions of a BCM 1312. The BCM 1312 includes an elution passage 1316 that is fluidically interposed, and fluidically connected with, sample ports S1 and S2 which serve to fluidically connect the elution passage 1316 with fluidic features contained within the cartridge. The elution passage 1316 in this example follows an arcuate or circular path for at least a portion of its length and has a plurality of exhaust passages 1322 that radiate outward from the elution passage 1316. The BCM 1312 also features a plurality of impaction ports 1324 and exhaust ports 1326, with each exhaust port 1326 being located at the end of, and fluidically connected with, one of the exhaust passages 1322 opposite from the end of that exhaust passage 1322 that is fluidically connected with the elution passage 1316, and each impaction port 1324 is fluidically connected with the elution passage 1316 such that each exhaust passage 1322 fluidically connects with the elution passage 1316 at a location that is fluidically interposed between two adjacent impaction ports 1324 or such that each impaction port 1324 is fluidically interposed between two locations where adjacent exhaust passages 1322 fluidically connect with the elution passage 1316.

The BCM 1312 may also feature an annular lower wall 1318 that extends from the surface or structure having the impaction ports 1324 towards the mouthpiece 1330. The annular lower wall 1318 may encircle the impaction ports 1324 and may extend away from the surface or structure having the impaction ports 1324 so as to overlap with an exhaust port seal 1319 and an impaction port seal 1320 (similar to the annular upper seal discussed earlier) when viewed from a direction perpendicular to the center axis of the mouthpiece 1330.

When the BCM 1312 is used to collect a breath sample, the test subject places their lips around the mouthpiece 1330 and exhales into it. The subject's exhaled breath will pass through the passage down the center of the mouthpiece and into the space between the surface having the impaction ports 1324 and the impaction port seal 1320. A gap exists between the surface having the impaction ports 1324 and the impaction port seal 1320, and the exhaled breath is therefor able to flow into the impaction ports 1324, through portions of the elution channel 1316, and out through the exhaust passages 1322 and the exhaust ports 1326, at which point it enters a generally annular plenum volume formed between the surface having the exhaust ports 1326 and the side of the exhaust port seal 1319 that faces the exhaust ports 1326 and then flows to a vacuum passage 1321. During sample collection, a vacuum source may be fluidically connected to the vacuum passage 1321 to apply a vacuum to the fluid volume between the vacuum passage 1321 and the mouthpiece 1330 through which the breath sample flows, thereby reducing the effort needed by the subject to provide a breath sample.

The BCM 1312 may also optionally include a BAC port 1315 that may interface with a BAC sensor during breath sample collection; the BAC port 1315 may divert a portion of the breath sample that is provided to the BCM 1312 to the BAC sensor for analysis.

Once the breath sample has been collected, the mouthpiece 1330 (or the structure to which it is connected) may be twisted relative to the rest of the cartridge, thereby causing the mouthpiece to simultaneously rotate and travel along the center axis of the mouthpiece 1330, i.e., towards the impaction ports 1324 and the exhaust ports 1326 of the BCM 1312. The exhaust port seal 1319 and the impaction port seal 1320 may thus be brought into contact with the surface or surfaces having the exhaust ports 1326 and the impaction ports 1324, respectively, so that the exhaust port seal 1319 and the impaction port seal 1320 may act to seal off the exhaust ports 1326 and the impaction ports 1324, respectively.

Once the breath sample has been captured in the BCM 1312 and the BCM sealed to capture the breath sample in the cartridge 1302, a vacuum pump can be used to draw ambient air through a cartridge to capture the ambient air sample. The ambient air sample can be collected in the cartridge 1302 within an ambient air sample chamber or in another cartridge. Then, the cartridge 1302 may be interfaced with a base station or other analysis device that may manipulate or otherwise cause the cartridge to operate in order to cause an analysis of the collected sample to be performed.

Flexible Fluidic Structures

A fluidic system may incorporate a fluidic structure and various systems or mechanisms for controlling how fluids flow within fluidic circuits defined within the fluidic structure. The fluidic structure of a fluidic system may be removable from the system in some cases, allowing for the fluidic structure to be replaced with a new fluidic structure in order to perform a subsequent analysis or fluid processing operation without risking contamination from the most recent previous such analysis or fluid processing operation. The fluidic circuits or flow paths within the fluidic structure may be configured to transport fluids processed within the fluidic system from one location within the fluidic structure to another responsive to inputs received from other components of the fluidic system. A fluidic circuit may be understood to be analogous to an electrical circuit, e.g., a collection of one or more fluid flow paths that fluidically connect together various other fluidic elements, e.g., reservoirs, chambers, etc., within a fluidic structure.

In traditional mini- and microfluidic systems, the channels that define the various fluidic flow paths or circuits of a fluidic system are typically formed in a fluidic structure that is composed of a rigid (or at least self-supporting—it may, for example, be made of molded elastomer, such as PDMS) substrate, e.g., an etched or machined substrate or an injection molded substrate or housing. Such a substrate may then be interfaced with a rigid plate and/or elastomeric membrane that seals the channels and/or provides volume change within portions of the fluidic circuit(s) in order to provide for valving and pumping control. Fluid flow in such fluidic systems is accomplished by using pump structures located either within the substrate or offboard of the substrate, with the pressure produced by the pump structures being communicated through the flow paths in order to move fluid from one location in the fluidic structure to another.

In certain embodiments, micro- and minifluidic structures are provided using a flexible substrate. Instead of using a rigid substrate with channels formed therein (or a substrate in which the flow channels are otherwise self-supporting, e.g., such as may be the case in a substrate made of cured silicone), in certain embodiments, one or more fluidic circuits are defined between two (or more) flexible, but relatively inelastic, portions of material, such as sheets of Mylar, that are selectively joined together, e.g., using heat-sealing, in order to create seals that define the perimeter(s) of various chambers and fluidic paths that make up a particular fluidic circuit (as used herein, "inelastic" material refers to material that possess a modulus of elasticity and/or thickness that result in the material stretching by 1% or less when subjected to a 10 psi pressure field; in some contexts, the inelastic material may be replaced with relatively inelastic material, which may have an elasticity and/or thickness that result in the material stretching by 10% or less when subjected to a 10 psi pressure field). By avoiding the use of a rigid or self-supporting substrate to define the fluidic circuits and other fluidic elements, such fluidic structures are able to transition between a flat, collapsed state when unpressurized (or at sub-atmospheric pressure), and an inflated/semi-inflated or un-collapsed state when pressurized (with the term "inflate" in this context referring to filling such fluidic flow paths with liquid or gas). For example, if two portions of material are sealed or joined together when the space in between the two portions of material is held at a vacuum or otherwise sub-atmospheric pressure level, the resulting fluidic structure may provide a fluidic circuit having one or more portions thereof that are held at a vacuum or partial vacuum (or may be held at a zero volume) until they are fluidically connected with a higher-pressure environment. It will be understood that the portions of material can be from separate sheets, or may be portions of material from the same sheet, e.g., a sheet that has been folded over on itself, with each portion of material lying on an opposite side of the fold line and facing the other portion of material.

There is considerable flexibility in where such seals are placed, as will be evident from later discussion below relating to various examples, but some implementations may feature, for example, portions of material that are joined together along two parallel seal lines that define between them a passage running down the middle, or near the middle, of two portions of material. The passage may have a width equal to the gap between the two seal lines (when pressurized, the passage may expand into a more cylindrical shape if both portions of material are thin and flexible, thereby causing the passage width to contract but the passage height to increase). The portions of material in such examples may be additionally joined together in other locations as well, e.g., along lines that outline a fluid reservoir located on either side of the passage, or along parallel lines that define passages between such reservoirs and or other reservoirs or passages.

As a result, the working volumes of such collapsible fluidic structures, i.e., the volumes that contain fluids needed in the operation of the fluidic structure, are provided on-demand when pressurized fluid is introduced into such structures. In effect, the entire fluidic circuit may be viewed as a collection of discrete bladders that selectively transition between a "flat" state in which they have low, and in many cases, zero volume, and a "pressurized" state in which they have non-zero volumes. This avoids the need to displace a prior fluid, e.g., air, that was contained within such a fluidic structure prior to introduction of the sample of interest, thereby reducing the amount of fluids needed and/or reducing the likelihood of air bubbles being present in the fluid of interest. There is also the further benefit that by having the various fluidic chambers and passages of the fluidic circuit empty of fluid prior to use, there is no need to either provide a contained volume in which to capture such pre-existing fluids when displaced by the working fluids of the fluidic system or provide venting features that allow such pre-existing fluids to be vented outside of the fluidic system when displaced by the working fluids of the fluidic system. In the context of fluidic systems that are used for biological and chemical assays, the ability to omit vents, e.g., openings or passages that allow a fluid to enter or exit from a fluidic circuit in a fluidic structure, e.g., to ambient atmosphere, is particularly advantageous, as vents may serve as both potential points of entry for contaminants into the fluidic system, which may render any fluidic analysis that is performed less accurate, and leak sources that may allow potentially dangerous biological and/or chemical substances to escape from the fluidic system, thereby posing a hazard to operators.

Some such "on-demand" fluidic structures may also be operated without the need for traditional, discrete pumps. For example, since the fluidic structure itself may be constructed from a flexible material, fluid may be moved around with the fluidic structure through the application of pressure on different portions of the fluidic structure, essentially squeezing the fluid from one portion to another portion of the fluid structure.

In some such implementations, such fluidic structures may be positioned between two clamping structures so as to create one or more zones of increased pressure on one or more portions of the fluidic structure. In such implementations, the fluidic structure and/or one or both of the two clamping structures may be configured to permit for relative movement between the fluidic structure and one or both of the clamping structures to allow the one or more zones of increased pressure to be moved from one location to another on the fluidic structure.

For example, in some implementations, such a fluidic structure may be placed with one side against a platen or other rigid surface. A roller may then be placed against the opposite side of the fluidic system and used to press the fluidic system against the platen or other rigid surface (the roller and the platen would be considered the "clamping structures," thereby generating a zone of increased pressure where the roller contacts the fluidic structure and compresses it against the platen or other rigid surface. By rolling the roller across the fluidic structure, the zone of increased pressure may be caused to move across the fluidic structure in the same direction, i.e., along the axis of movement of the roller. Fluid that is contained within the fluidic structure in one or more portions that are subjected to the moving pressure zone may, for example, be squeezed into one or more adjacent portions of the fluidic structure when the zone of increased pressure is applied to such fluid. In this manner, it is possible to use a roller (or other structure that is able to provide for a zone of increased pressure that can be caused to move relative to the fluidic structure) to move fluids between various parts of such a fluidic structure.

Figure 15:
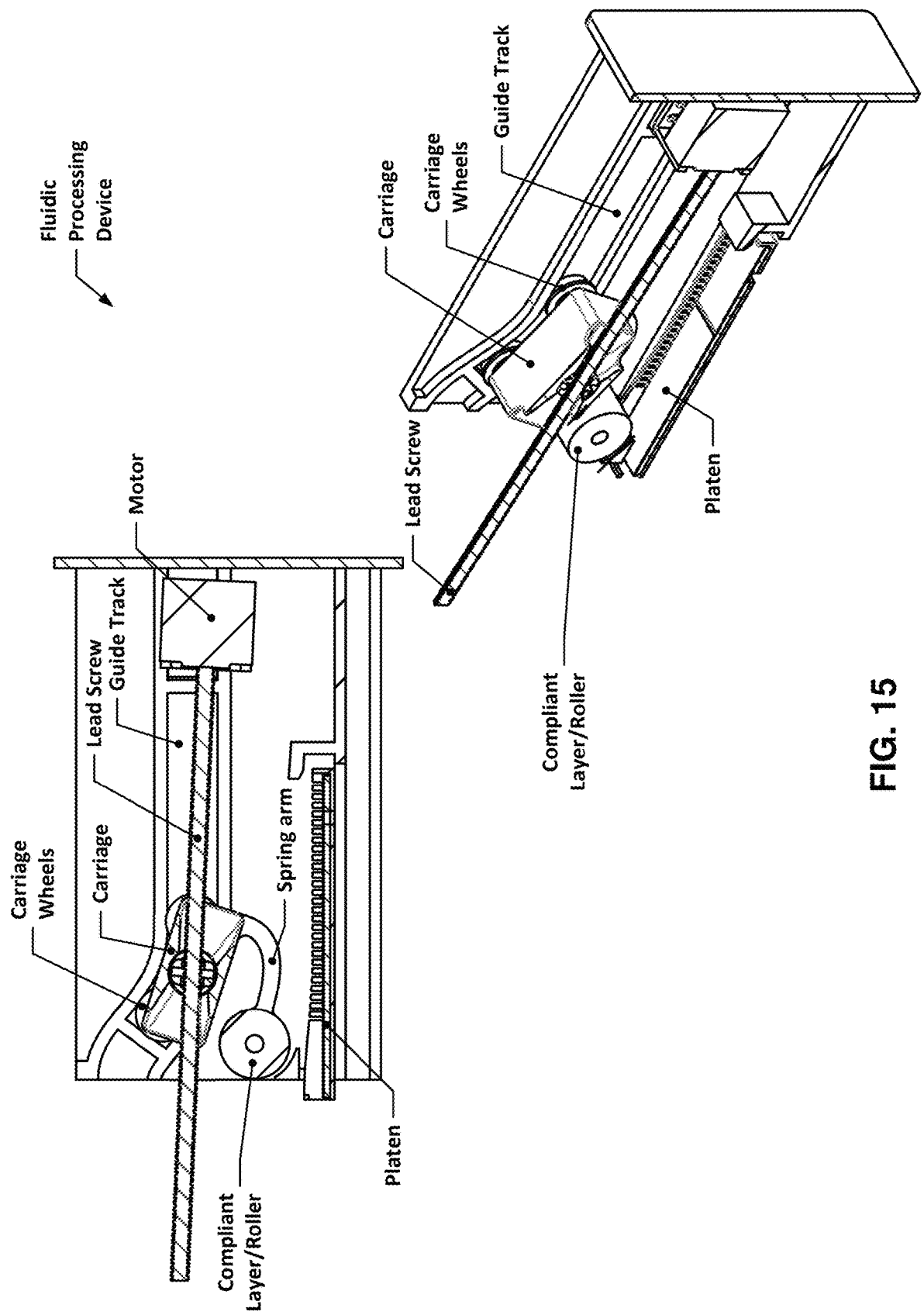
FIG. 15 depicts an example of a portion of a fluidic system that may be used to apply a movable clamping pressure zone to a fluidic structure.
Figure 16:
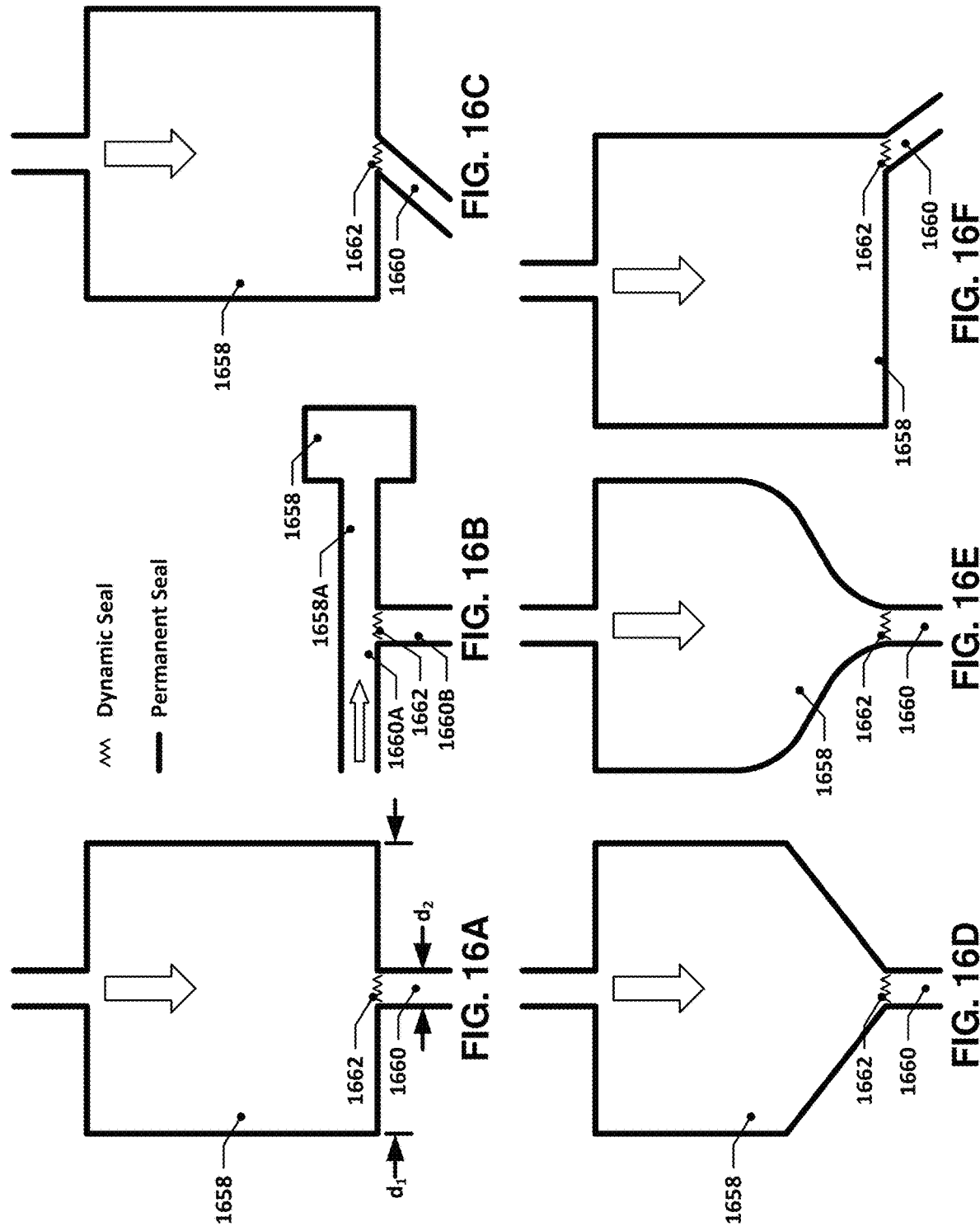
FIGS. 16A-16F depict example fluidic structures for providing dynamic seals.

FIG. 15 depicts cutaway views of a portion of an example fluidic system that may interface with the fluidic structures discussed herein and may be used to actuate the fluidic structures discussed herein. The depicted device may include a carriage that has wheels that are positioned within a guide track that may be configured to cause the carriage to move closer to, or further from (or maintain a constant distance from), a platen as the carriage is moved along the guide track. A motor may be used to actuate a lead screw that may be rotated in order to move the carriage along the lead screw, thus causing the carriage to transit along the guide track. The carriage may have a spring arm that may apply a spring force to a roller that may be pushed into contact with the platen as the carriage transits along the guide track. A fluidic structure may be placed in the fluidic system in between the platen and the roller, and the roller may be caused to apply a moving clamping pressure zone to the fluidic structure by actuating the motor and lead screw so as to cause the carriage to move along the guide track; as the carriage moves, the roller, which moves with the carriage, may exert a clamping pressure on the fluidic structure that generates the clamping pressure zone. Other mechanisms that provide similar functionality may also be used and are considered to be within the scope of this disclosure as well.

It will be further understood that the system shown in FIG. 15 is but one example system that may be used to interface with, and act on, the fluidic structures discussed herein. In other implementations, systems with multiple rollers, which may be staggered relative to each other along an axis perpendicular to their rotational axes and/or which may be configured to be movable independently of one another along one or more axes, may be provided to allow for multiple clamping pressure zones to be simultaneously applied to a single fluidic structure, thereby providing greater flexibility in how the fluidic circuit(s) of the fluidic structure are able to be operated. In yet other implementations, the clamping pressure zones that are applied may be provided by mechanisms other than the rollers discussed herein. For example, a roller that can swivel, e.g., a caster, may be used to allow the direction of movement of the roller to be adjusted so as to support multi-directional roller movement. In yet other implementations, mechanisms other than, or in addition to, rollers may be used, e.g., solenoids may be used to apply some clamping pressure zones, e.g., to fluid reservoirs or other such areas. In some implementations, as discussed below with respect to some implementations, rollers (or other clamping zone application mechanisms) may be caused to reverse direction. This may facilitate various operations, e.g., sealing a previously traversed passage segment (the clamping pressure zone may act to push the to-be-sealed area of the fluidic structure into good thermal contact with the heating element used to make the seal), mixing (as discussed with respect to FIG. 18, in which the clamping pressure zone was reciprocated back and forth), and/or wash operations (e.g., to drive fluids back out of an area of interest).

In some such implementations, the use of a movable zone of increased pressure allows for such fluidic structures to be operated using much simpler equipment than is typically required. For example, a typical fluidic structure may require multiple pumps and valves to be provided in order to operate, with each such pump and valve typically requiring a separate actuator or other actuation mechanism. In contrast, fluidic structures such as those described above may be operated with only a single actuation mechanism that may be used to cause the roller (or other clamping structure that provides a movable zone of increased pressure) to move relative to the fluidic structure.

In addition to simplifying the actuation mechanism needed to operate such fluidic structures, fluidic structures such as those described above may also be easily manufactured using available materials. Suitable flexible materials, e.g., Mylar, BoPET, or cellophane, may be easily assembled, e.g., using heat welding, laser welding, ultrasonic welding, heat pressing, etc., to produce the fluidic structures discussed above. Such structures may, for example, be provided by clamping two portions of such material between two heated platens that have raised patterns that define the desired bond lines between the two portions of material. The clamped portions of material may, in the regions of the raised patterns, be caused to bond together due to the localized application of heat in those areas, with the remainder of the portions of material remaining unbonded. Such fluidic structures are inexpensive to manufacture. In some implementations, non-polymeric materials, e.g., metal foils, may be used to provide a portion of material. For example, a thin aluminum, gold, or other film or foil may be used instead of a polymer like Mylar, BoPET, or cellophane. In such implementations, other types of joining operations may be used to provide permanent and temporary seals (temporary and permanent seals are discussed in more depth below), e.g., double-sided adhesive gaskets that adhere the portions of material together only in the regions where the seals are to be located or sandwiching a thin polymeric gasket defining the permanent and temporary seals in between such portions of material and then heat-sealing the polymeric gasket to both adjacent portions of material, thereby joining the two portions of material together. Techniques such as laser welding may also be used, when appropriate, to join the portions of material to one another to define the temporary and permanent seals.

Other benefits of such fluidic structures include reduced packaging size (for example, such fluidic structures may be stored in a rolled-up form, whereas traditional fluidic structures are rigid and cannot be transitioned to a more compact format), lighter weight, suitability for shipment via normal letter envelopes (as opposed to requiring a package), enhanced resistance to breakage, etc.

The seals may be designed to be "permanent," i.e., not intended to fail structurally during normal use, or "temporary," i.e., intended to fail structurally under certain conditions during normal use, e.g., when a particular pressure is reached within the portion of the fluidic structure adjacent to such temporary seals.

For instance, temporary seals may also be designed to fail or rupture in various ways. For example, if two sheets of Mylar are thermally bonded together to form a temporary seal, such a temporary seal will tend to rupture along most or all of its length when subjected to a pressure greater than its rupture pressure, "popping" open to provide a passageway in which very little of the temporary seal remains. In material such as cellophane, however, the same type of temporary seal may tend to rupture by forming one or more pinholes through the seal area, leaving most of the temporary seal intact. As a result, the temporarily sealed passageway may still be relatively obstructed even after the temporary seal ruptures, although the velocity of the fluid that is forced through the pinholes in the ruptured temporary seal in such cases may be significantly higher than it would otherwise be, e.g., if the entire temporary seal had ruptured along its length (thus providing a single, large passage with little flow restriction compared to the pinholes). Such temporary seals may, in some instances, be used to promote jetting and/or mixing of fluids used in the fluidic systems discussed herein.

Each temporary seal may be placed so as to extend between two different portions of the permanent seal(s) and/or another temporary seal or seals. The temporary seals may be used to create temporary chambers or working volumes that may, during use of the fluidic circuit, be fluidically isolated from one or more other chambers or working volumes adjacent thereto by way of such a temporary seal and which may then be caused to eventually fluidically connect with such one or more chambers or working volumes through intentional failure or bursting of the temporary seal, thereby allowing the contents thereof to be pumped or pushed, e.g., through movement of the roller or other force-application mechanism along an axis, from that temporary chamber to a downstream fluidic structure, e.g., another chamber or a fluidic channel. The temporary seals may have a burst or rupture pressure that is less than that of the permanent seals (in fact, the permanent seals may even have a burst or rupture pressure that exceeds that of the portions of material itself, i.e., the portion of material may fail before the permanent seal does)—this burst or rupture pressure may be significantly less, e.g., an order of magnitude or more less, than that of the permanent seals.

Fluidic structures such as those discussed herein may also utilize, in place of or in addition to temporary seals, dynamic seals. Dynamic seals are seals that are caused to come into being dynamically responsive to the pressurization of particular fluidic structure geometries; such dynamic seals effectively seal such a pressurized fluidic structure off from one or more downstream fluidic flow paths that would otherwise normally be fluidically connected with the pressurized fluidic structure. Various examples of such fluidic structures are shown in FIGS. 16A-16F, which are discussed further below. In each of FIGS. 16A through 16F, the dynamic seals are represented are represented by a sawtooth.

In FIG. 16A, a fluidic structure is shown that has a reservoir 1658 that has a passage 1660 that is fluidically connected thereto. Another passage, not marked, may provide fluid to the fluidic structure. The fluidic structure is, as with the previous fluidic structures discussed herein, composed of two portions of material that are sealed together using permanent seals along the paths indicated. The permanent seals define the reservoir 1658, the passage 1660, as well as the other passage. There may, of course, be other fluidic structures that are also defined between the two portions of material that are not depicted in FIG. 16A, such as any of the various other fluidic structures discussed herein, and that may be fluidically connected to, and upstream and/or downstream of, the fluidic structure depicted in FIG. 16A. This is similarly true for the fluidic structures of FIGS. 16B through 16F.

When the fluidic structure is first pressurized, e.g., when fluid is introduced into the reservoir 1658 through the inlet passage, the fluid will, through capillary action, wick into the reservoir 1658 but will not initially flow into the passage 1660 in any appreciable amount. In effect, a dynamic seal 1662 forms at the junction between the passage 1660 and the reservoir 1658. As fluid continues to flow into the reservoir 1658, the pressure in the reservoir 1658 may continue to increase, causing at least one portion of material forming the top or bottom of the reservoir 1658, if not both, to bulge outward. At the same time, the dynamic seal 1662 may continue to prevent, or effectively prevent, fluid flow into the passage 1660. However, at some point, the pressure within the reservoir 1658 may reach a threshold level that causes the dynamic seal to fail, causing the passage 1660 to become fluidically connected with the reservoir 1658.

Thus, the dynamic seal 1662 acts, in many respects, in a manner similar to the temporary seals discussed above. The two seals differ in that there is actually a non-permeable physical bond in the temporary seal that prevents fluid flow from occurring which is then ruptured or broken when the pressure on one side of the seal exceeds a threshold amount, whereas the dynamic seal does not have such a non-permeable physical bond and instead operates by, in essence, clamping the passage 1660 shut.

While the mechanism behind the operation of such dynamic seals has not yet been fully characterized, it is believed that the sealing behavior of such dynamic seals is likely provided by a combination of capillary/surface tension effects and separate mechanical clamping effects that arise from the use of at least one portion of material that is thin and flexible, yet relatively inelastic.

When the fluid first flows into the reservoir 1658 and encounters the location where the passage 1660 fluidically connects with the reservoir 1658, for example, there may be strong opposing capillary forces at play when the fluid tries to turn the corner (the corner or corners where passage 1660 intersects with the permanent seal that defines the reservoir 1658) that may act to discourage the fluid from flowing into the passage 1660. In effect, the surface tension of the fluid, assuming the fluid is liquid, needs to be overcome in order for the fluid to flow into the passage 1660. This effect may be particularly pronounced in fluidic systems formed between portions of material that are hydrophobic in nature. For example, fluidic systems defined by permanent seals formed between two sheets of flexible Mylar, for example, may be generally hydrophobic, and it was observed in such systems that a reservoir 1658/passage 1658 configuration as discussed above formed a dynamic seal even when the amount of fluid introduced into the reservoir 1658 was quite small. For example, when fluid is initially introduced into the reservoir 1658, the fluid may wick into the reservoir 1658 through capillary action, without really requiring active pressurization through the application of a moving clamping pressure zone upstream of the reservoir 1658. The dynamic seal may provide a sealing effect even under these low-pressure conditions.

When the reservoir 1658 is further pressurized, however, the resulting outward bulging of at least one portion of material (if not both portions of material—as discussed above, one or both portions of material may be made from a flexible yet relatively inelastic material, e.g., Mylar) that defines the reservoir 1658 results in sharp bends or creases to occur in the material portion(s) where the permanent seals are located that bound the reservoir 1658. When there is a smaller-aperture passage that intersects with one of these permanent seals, e.g., the passage 1660, it is believed that the creases that form along the boundaries of the reservoir 1658 span transversely over the passage 1660, thereby increasing the bending stiffness of the material portion(s) that spans over the intersection between the reservoir 1658 and the passage 1660. This is believed to prevent the material portion(s) that define the passage 1660 from bulging upwards, as those material portion(s) are not able to easily bend in a plane that is perpendicular to the page (with respect to the orientation of FIG. 16A) and parallel to the edge of the reservoir 1658 where the passage 1660 connects. For example, the material portion(s) that are creased may act, in effect, like a piece or pieces of angle channel that have bending stiffnesses that far exceed that of un-creased material portions. The creased portion(s) spanning over the passage 1660 may thus act like a rigid piece of material that presses against another rigid piece of material (such as another creased portion in the other material portion, or against a rigid material if one of the two material portions is rigid). While some small amount of fluid may still potentially squeeze past this clamped interface, such an amount may, for practical purposes, be negligible. When the pressure within the reservoir 1658 reaches a particular threshold level, however, the fluid pressure will eventually push back on the creased portions that span the passage 1660 and cause them to buckle, thereby allowing the material portions that define the passage 1660 to bulge up and allow the fluid to flow into the passage 1660 in a generally unobstructed manner.

Those with familiarity with traditional microfluidic systems looking at a structure that provides a dynamic seal in isolation, i.e., without the benefit of knowledge of how the fluid flow through the structure occurs and without the knowledge that the structure in question is part of a fluidic structure defined between two portions of material in which at least one, if not both, portions of material are made from a flexible, relatively inelastic material, may mistakenly believe that they are observing a "stop junction," which is a fluidic structure used in traditional microfluidic systems in a somewhat similar manner.

As noted earlier, traditional microfluidic systems are typically formed in a rigid fluidic structure, e.g., in an injection-molded housing or a laminated substrate or plate such that the fluidic passages and chambers within the microfluidic system retain their cross-sectional shapes regardless of whether there is liquid in them or not. As a result, small passages that are present in such traditional microfluidic structures may act, in effect, as capillary tubes, tending to try and retain fluid therewithin. This effect is typically enhanced further by the materials used in traditional microfluidic structures, which may be hydrophilic. As a result, when liquid is flowed through a small-size passage into a larger chamber in a traditional fluidic system, the liquid will tend to tend to "stop" at the junction between the small-size passage and the larger chamber, being encouraged to remain within the passage by capillary and surface tension forces. The liquid will, eventually, flow into the larger chamber once the pressure applied to the liquid is sufficient to overcome the capillary/surface tension forces that cause the liquid to remain at the mouth of the small passage. In contrast, liquid that is flowed into the small-size passage from the chamber, i.e., in the reverse direction, may tend to wick into the small-size passage-actively seeking to flow into the small-size passage as opposed to resisting flow into the small-size passage.

In contrast, dynamic seals in fluidic structures that are formed between two portions of material, with one or both portions of material being a flexible, relatively inelastic material, are provided when fluid is flowed from a chamber into a smaller-size passage (or from a passage into another passage that tees into the first passage). Thus, while both dynamic seals and stop junctions may be formed in regions where there are intersections of small passages with larger chambers, flow occurs in opposite directions with respect to each structure. Moreover, while stop junctions rely entirely on capillary effects, dynamic seals may derive additional sealing capability from the mechanical clamping effects that are believed to occur due to the creases formed at the permanent seals by the distension of the portion or portions of material that are flexible but relatively inelastic. This clamping effect may allow dynamic seals to obtain higher release pressures, i.e., the back pressure that must be applied to the fluid in order to cause the dynamic seal to release, than may be achievable with stop junctions that are used in traditional microfluidic structures (the release pressure for a stop junction being the back pressure that must be applied to the fluid in order to overcome the stop junction effect).

There may also be enhanced capillary forces in dynamic seals that arise in conjunction with a crease or creases formed in the portions of material that are flexible but relatively inelastic. As mentioned previously, capillary forces and surface tension may act to discourage a liquid from flowing from a larger chamber and into a smaller passage that fluidically connects therewith. This is believed to be due to such capillary forces and surface tension effects making it difficult for such a liquid to turn a corner, e.g., into the passage. When there is a relatively small amount of liquid present in the chamber leading to the passage, the structure may generally remain planar, with the "corners" being provided solely by the permanent seals that define the passage and the chamber. However, when the chamber is filled with sufficient liquid to cause the portion or portions of material that are flexible but relatively inelastic to distend and form creases, the creases may, in effect, act as additional corners that the liquid in the chamber must turn around in order to enter the passage. These additional corners may provide further opportunity for capillary and surface tension effects to act on the liquid so as to discourage the liquid from entering the passage.

Generally speaking, the smaller the width of the passage 1660 where the passage 1660 intersects with the permanent seals that define the reservoir 1658, the higher the pressure at which the dynamic seal that is formed at the intersection of the passage 1660 with the permanent seal that defines the reservoir 1658 will release, allowing fluid to flow into the passage 1658. For example, a dynamic seal that is formed where a passage 1660 that is 0.4 mm wide intersects with a permanent seal that defines a reservoir 1658 will release/open at a higher pressure than if the same passage 1660 were 0.7 mm in width at that point. Similarly, a dynamic seal that is formed where a passage 1660 that is 0.7 mm wide intersects with a permanent seal that defines a reservoir 1658 will release/open at a higher pressure than if the same passage 1660 were 1 mm in width at that point.

The length ($d_1$) of the permanent seal that defines part of the reservoir 1658 where the passage 1660 fluidically connects with the reservoir 1658 should be larger than the width ($d_2$) of the passage 1660 at that point. For example, a $d_1/d_2$ ratio as low as 1.5 was found to form a dynamic seal, but one that had a very low release pressure, e.g., a release pressure low enough that the reservoir 1658 could not actually be pressurized to the point where it was at its maximum volume. A $d_1/d_2$ ratio of at least 3 was found to provide a sufficiently high enough release pressure that the reservoir 1658 could be pressurized to the point where it was at, or very near to, its maximum volume (assuming no stretching of the portions of material), and a $d_1/d_2$ ratio of at least 8 was found to provide a release pressure that was high enough to cause a spring-loaded roller that was used to apply the moving clamping pressure zone by compressing the fluidic structure against a rigid platen to lift up off of the unpressurized portions of material/platen when traversing over the pressurized reservoir 1658 (this spring-loaded roller was applying approximately a 15-20 pound compressive force to the clamping pressure zone). In such a situation, the movable clamping pressure zone may be unable to actually apply pressure to the reservoir 1658 that is sufficient to overcome the release pressure, thereby causing the dynamic seal to remain sealed. In such situations, various approaches may be taken to address this issue—for example, the force exerted by the clamping pressure zone may be increased to meet the requirements of the higher release pressure. Alternatively, additional features may be included near the dynamic seal, such as the floating seals discussed elsewhere herein, to effectively limit or lower the release pressure for a particular dynamic seal.

The depth of the reservoir 1658 in a direction perpendicular to the permanent seal at which the passage 1660 fluidically connects with the reservoir 1658 may also vary. In some implementations, the depth of the reservoir 1658 in a direction perpendicular to the permanent seal at which the passage 1660 fluidically connects with the reservoir 1658 may be nominally equal to the width of the passage 1660, as shown, for example, in FIG. 16B.

In FIG. 16B, permanent seals define a passage 1660A that is fluidically connected with a reservoir 1658. A second passage 1660B intersects with the passage 1660A upstream of the reservoir 1658 along one of the longer walls formed by the permanent seals that define the passage 1660A. In such an arrangement, the passage 1660A may act, in effect, like the reservoir 1658 of FIG. 16A, causing a dynamic seal 1662 to develop at the intersection of the passage 1660B with the passage 1660A. As a result, fluid flowing through the passage 1660A will be constrained to flow into the reservoir 1658 until the reservoir 1658 (and the passage 1658A) is pressurized to a first threshold amount. Once the first threshold amount is reached, the dynamic seal 1662 that seals off the passage 1660B will release, allowing the fluid that is subsequently flowed through passage 1660A to flow into the passage 1660B (assuming the clamping pressure zone continues to advance so as to maintain the pressurization of the fluid-if the fluid pressure drops sufficiently, e.g., to a first threshold amount lower than the release pressure, the dynamic seal may re-seal until the pressure is again increase to the release pressure). As with the passage discussed with respect to FIG. 16A, the smaller the width of the passage 1660B where the passage 1660B intersects with the permanent seal that defines the passage 1660A, the higher the pressure at which the dynamic seal 1662 that is formed at the intersection of the passage 1660B with the permanent seal that defines the passage 1660A will release.

In cases where a passage fluidically connects with a much larger chamber or reservoir, the distension or bulging of the larger chamber or reservoir may result in a dynamic seal that has too high a release pressure to operate reliably. In such cases, the addition of a floating seal may be used to reduce the release pressure of the dynamic seal in that location.

The passages that are sealed by the dynamic seals discussed above do not necessarily need to intersect the permanent seal at which the dynamic seals are formed at a 90° angle, as shown in FIGS. 16A and 16B. In some implementations, the passages that are sealed by the dynamic seals discussed above may intersect the permanent seal that defines the upstream passage or reservoir that is sealed off from the downstream passage by a dynamic seal at an oblique angle, and thus have a smaller transverse width than the width of the dynamic seal. FIG. 16C depicts an example of this, where a passage 1660 intersects with the permanent seal that defines a reservoir 1658 at a 45° to form a dynamic seal 1662. Regardless, the behavior of such a dynamic seal may generally be governed by the width of the gap in the permanent seal where the passage 1660 fluidically connects with the reservoir 1658 (or another passage 1660, e.g., as shown in FIG. 16B). The reduced width of such a passage 1660 downstream of the dynamic seal 1662 may have little or no effect on the pressure at which the dynamic seal 1662 may release, although it may affect the flow rate of the fluid through the passage for a given pressure once the dynamic seal 1662 does release.

The permanent seal with which a passage fluidically connects to form a dynamic seal does not necessarily need to be straight, as shown in FIGS. 16A through 16C. Dynamic seals may also form where passages fluidically connect with a permanent seal that is non-linear-if the volume that is bounded by the permanent seal upstream of the passage represents, in effect, a large expansion in size of the passage, then a dynamic seal may still be caused to come into being where the passage starts to increase in size, e.g., at the intersection of the passage with the larger-cross-section upstream chamber or passage. FIG. 16D, for example, shows a reservoir 1658 in which the permanent seals that define the reservoir 1658 define a pentagonal shape instead of a rectangular shape. The two bottommost permanent seals of the reservoir 1658 are perpendicular to each other, forming somewhat of a funnel shape before they meet the passage 1660. A dynamic seal 1662 is formed where the two bottommost permanent seals of the reservoir 1658 meet with the passage 1660. The dynamic seals formed in such arrangements may, for a given width of the dynamic seal, be weaker than the same width of dynamic seal in a fluidic structure such as is shown in FIG. 16A.

Dynamic seals may also be formed where passages transition to larger-width volumes in a more gradual manner, e.g., as shown in FIG. 16E. In FIG. 16E, a reservoir 1658 is shown that is defined by permanent seals that smoothly transition from the larger width of the reservoir 1658 to the smaller width of the passage 1660. A dynamic seal 1662 may nonetheless still form where the passage 1660 ends, e.g., where the passage width starts to widen and expand in order to transition to the reservoir 1658. In such an implementation, the pressure at which the dynamic seal releases for a given passage width may, for example, be less than the pressure at which a dynamic seal for a passage of similar width releases in configurations such as are shown in FIGS. 16A-16D. In some such implementations, if the smooth transition from the larger width of the reservoir 1658 to the smaller width of the passage occurs over a long enough distance, e.g., the radii of curvature for such transitions is quite high, e.g., larger than the width of the reservoir 1658, then there may actually be no or almost no dynamic seal effect generated at all.

As is likely evident from the implementations of FIGS. 16D and 16E, dynamic seals also do not necessarily need to be formed in the middle of a permanent seal. As shown in FIG. 16F, a dynamic seal 1662 can also be formed at a corner of a reservoir, e.g., where a passage 1660 intersects two permanent seal walls defining a reservoir 1658. The dynamic seal of such an implementation may, in effect, behave similarly to the dynamic seal of the implementation of FIG. 16D.

It will be generally understood that implementations disclosed herein in which temporary seals or dynamic seals are used may also be practiced, with suitable modification, using dynamic or temporary seals instead (vice-versa) in many cases, and the use of either type of seal may be assumed in place of the other unless otherwise indicated.

Figure 17:
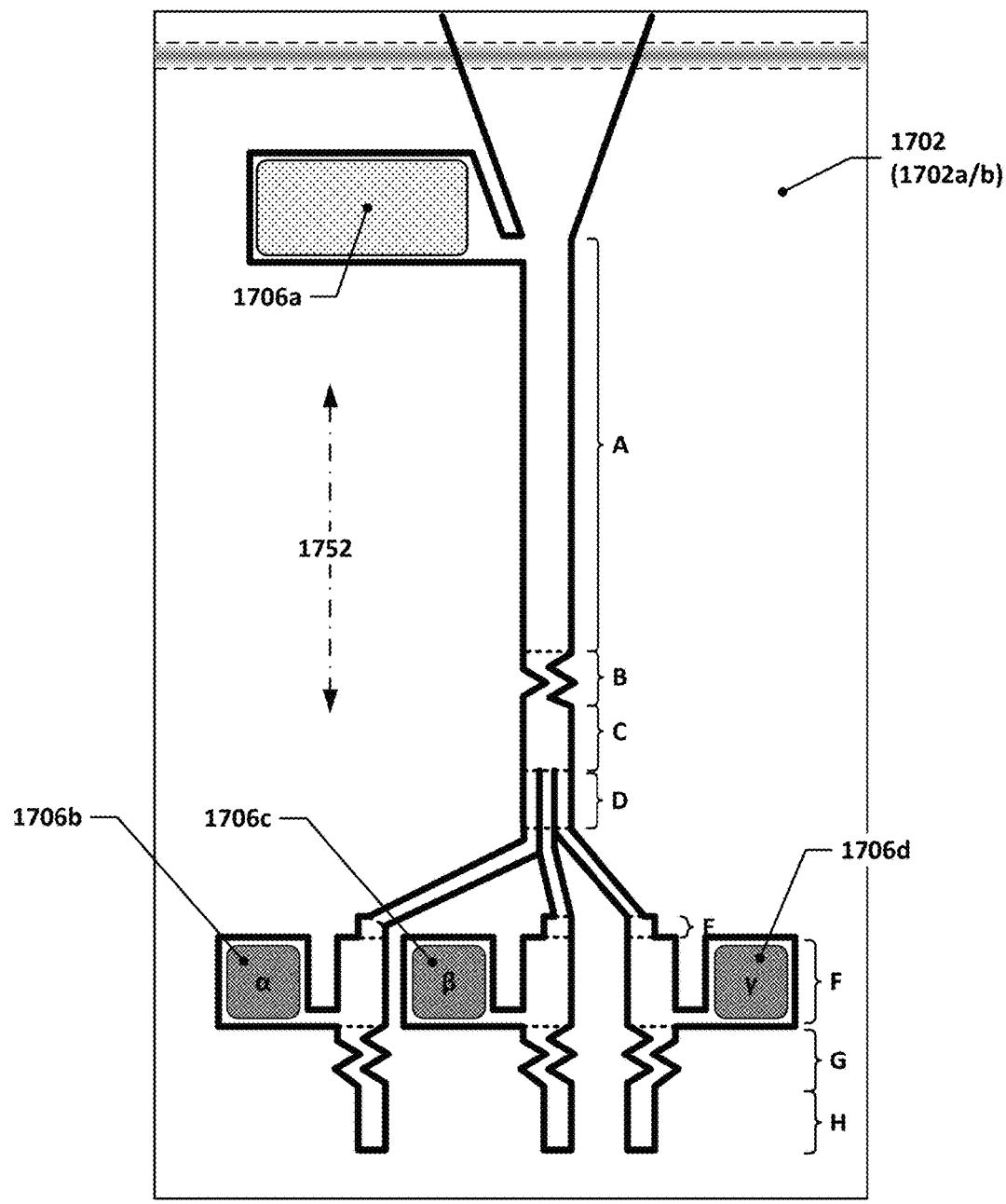
FIG. 17 depicts an example fluidic structure that may be used to perform multiple, different analyses.

While above-discussed example may be used to perform a single analysis on a sample, the fluidic structure architecture discussed herein may also be used to facilitate performing multiple analyses in parallel. FIG. 17 depicts a fluidic structure 1702 including a first fluid reservoir 1706a, as well as similar zones A, B, and C. Zone D of the fluidic structure 1702 features three metering volumes that will each receive generally equal volumes of fluid once the temporary seal between zones C and D ruptures and which will then provide those volumes of fluid to branching flow paths in between zones D and E instead of to a single flow path (in the event that different volumes of fluid are desired to be delivered to each branching flow path, the widths of each volume where the temporary seal between zones C and D is located may be adjusted to proportionately deliver more or less fluid to each volume). Each flow path leads to a different downstream fluidic circuit, each of which may be configured to perform different types of analysis or assays. For example, the three second fluid reservoirs 1706b/c/d may each contain different reagents or immunoassay materials ($\alpha$, $\beta$, and $\gamma$) that may be used to perform different analyses on the fluid that is provided to each downstream fluidic circuit. It will be apparent that the roller, as it causes the pressure zone to move along the fluidic circuit by moving along axis 1752, will cause the fluids within the fluidic structure 1702 to flow into all three downstream fluidic circuits. It will also be apparent that more or fewer such downstream circuits may be provided.

Figure 18:
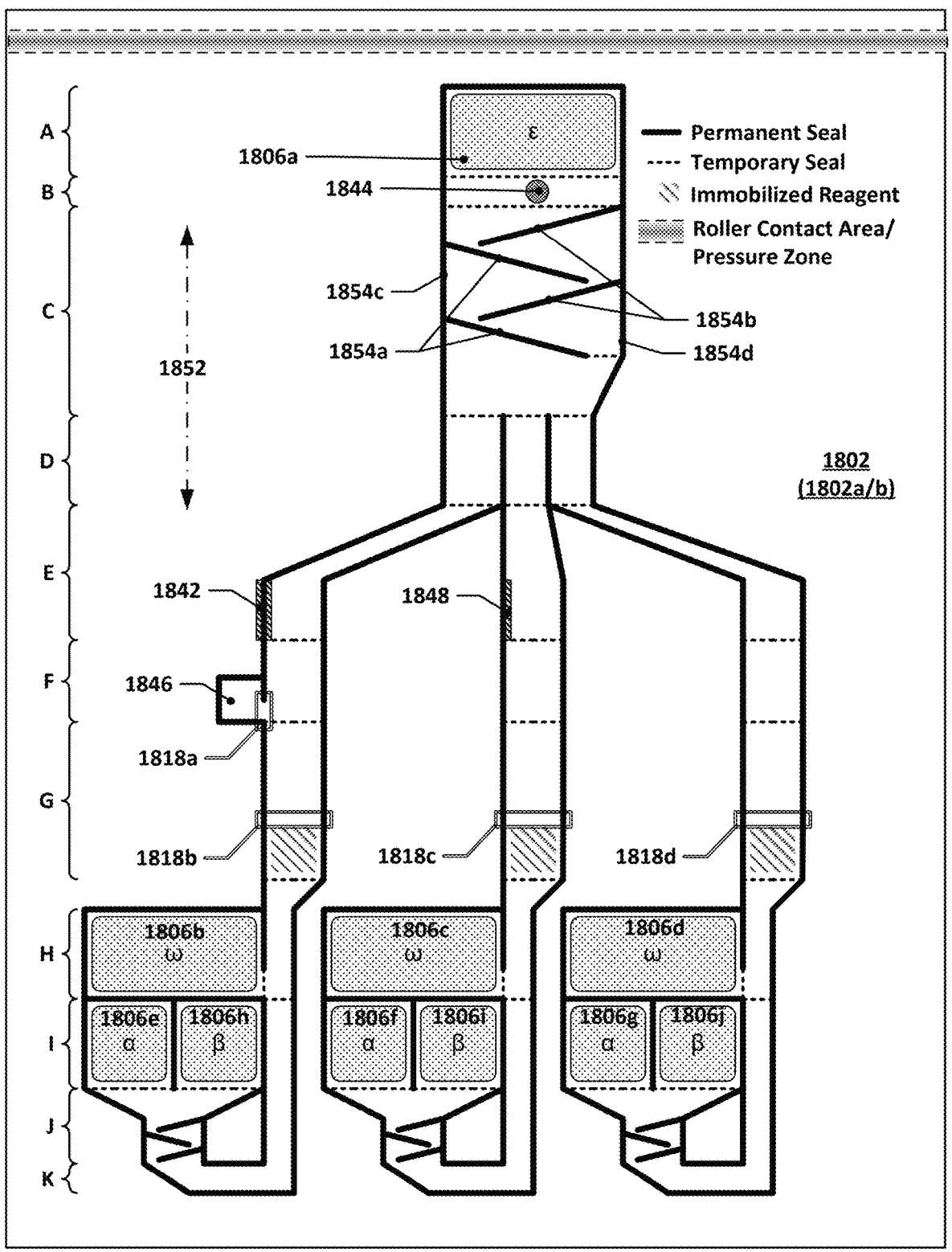
FIG. 18 depicts an example fluidic structure that may be used to measure a concentration of a biomarker or other material of interest.

Another example of a fluidic structure that may be implemented using the architecture disclosed herein is shown in FIG. 18. The fluidic structure 1802, which may have two portions of material 1802a and 1802b, similar to the earlier fluidic structures discussed herein, of FIG. 18 is designed to be implemented using the flexible fluidic circuit paradigm discussed herein and includes a plurality of permanent seals that define a fluidic circuit having a plurality of zones that are arranged in a linear fashion along an axis 1852. When the fluidic structure is processed by applying a moving pressure zone to it, e.g., with a roller, the moving pressure zone may be moved in directions parallel to that axis 1852, thus causing the pressure zone to move from one zone of FIG. 18 to another.

In zone A, the fluidic structure has permanent seals that define a first fluid reservoir 1806a that contains fluid E; fluid E may be an eluent, such as a buffer. Fluid E may be contained within a burstable pouch or blister that is positioned within the first fluid reservoir 1806a.

Zone A is separated from zone B by a temporary seal that forms one wall of the first fluid reservoir 1806a. When zone A is subjected to a clamping pressure, e.g., such as may occur when a roller is clamped against the fluidic structure and translated from zone A towards zone K, the clamping pressure will cause fluid E to be pressurized, eventually causing the temporary seal between zones A and B to rupture.

Zone B is a chamber that may include a reagent or material 1844, e.g., a lyophilized antibody, that is specific to a particular biomarker of interest. The reagent or material may be solid, e.g., a dry powder or a thin wafer of dried material, or liquid (in which case it may also optionally be secondarily contained within a burstable pouch or blister). Zone B may optionally be separated from zone C by a further temporary seal. When fluid E is forced from the first fluid reservoir 1806a by rupturing the temporary seal in between zones A and B, fluid E will be pushed into zone B and will mix with the reagent or material located within zone B (if that reagent or material is liquid and housed within a burstable blister or pouch, then this may occur after this second burstable blister or pouch is ruptured). The fluid E/reagent mixture may optionally be prevented from flowing into zone C by the temporary seal that is provided between zones B and C. In some implementations, this temporary seal may be omitted, but it may be beneficial to allow fluid E and the reagent some time to mix before advancing the mixture through the fluidic circuit.

Once fluid E and the reagent have been allowed to mix in zone B, the clamping pressure may be advanced further towards zone K, thereby pressurizing the fluid E/reagent mixture to a point that causes the temporary seal (if used) between zones B and C to rupture. The fluid E/reagent mixture may then be forced through zone C, which may contain multiple walls 1854a/b provided by permanent seals that are arranged in a "broken chevron" configuration, e.g., with each such wall 1854a/b extending from one wall 1854c/d of the passage extending through zone C towards an opposing wall 1854c/d of the passage extending through zone C. Such walls 1854a/b may be arranged in an alternating pattern, e.g., the wall or walls 1854a or 1854b adjacent to any given wall 1854c or 1854d may extend from the opposite side of the passage from the side of the passage from which the given wall 1854c or 1854d extends. Moreover, the walls 1854a/b may overlap one another when viewed along a direction aligned with the path of travel of the pressure zone. Finally, the distance from the tip of each wall 1854a or 1854b to the closest adjacent wall 1854b or 1854a may increase as that wall 1854a or 1854b approaches the side of the passage from which that wall 1854a or 1854b extends. In the depicted arrangement of FIG. 18, the walls 1854a/b give the appearance of two nested chevrons that have been broken apart in the middle and the two sets of chevron halves then offset vertically relative to each other and then inward towards each other. Other arrangements may be used as well to provide a similar effect. Such configurations may provide a similar effect to the zig zag feature discussed earlier, forcing the fluid that flows therethrough to undergo multiple flow reversals to help promote improved mixing of such fluid. The arrangement discussed above may further enhance mixing since each pair of adjacent walls may, in effect, cause the fluid to flow through a narrower opening before flowing into a larger volume trapped between the two walls. Each such transition may result in vortices being generated as the fluid flows from the narrower opening into the larger volume that follows. When the fluid is flowed through multiple such transitions, this may cause the fluid to undergo further mixing that may not be achieved using a constant-width zig zag passage.

Once the fluid E/reagent mixture has flowed through the flow-reversal section of zone C, it may be further pressurized by further advancement of the clamping pressure zone so as to cause a temporary seal at the end of the flow reversal section to rupture, thereby allowing the fluid E/reagent mixture to be delivered to an antechamber portion at the end of zone C. The antechamber portion of zone C may be separated from zone D by a further temporary seal.

Zone D may be partitioned internally by multiple permanent seals that may be spaced apart so as to divide the fluid E/reagent mixture into separate portions having desired relative volumes. For example, in the implementation of FIG. 18, there are two internal divider walls provided by permanent seals within zone D, forming a total of three different volumes directly beneath the temporary seal that partitions zone C from zone D. When the fluid E/reagent mixture collects above that temporary seal and is pressurized such that that temporary seal ruptures, the fluid E/reagent mixture will then rush into the separate volumes defined by the permanent seals in zone D. This may cause the fluid E/reagent mixture to be divided into sub portions that are sized to be proportionate to the relative widths of the temporary seal portions capping each such volume. For example, in the depicted example, the temporary seal portion above the leftmost volume is 33% wider than the corresponding temporary seal portions above each of the middle and rightmost volumes, thereby causing approximately 33% more of the fluid E/reagent mixture to collect in the leftmost volume of zone D than in the middle or rightmost volumes thereof (this assumes that the total volume of the fluid E/reagent mixture is less than the total volume within zone D). In some implementations, if the total volume of the fluid E/reagent mixture is known to be larger than the total volume of zone D, then the temporary seal between zones C and D may be omitted, as each volume in zone D will fill completely with the fluid E/reagent mixture, with any surplus spilling over into the adjoining volumes until all of the volumes are filled.

Each of the volumes in zone D defined between the walls provided by the permanent seals in zone D may lead to a separate fluidic sub-circuit that may be fluidically isolated from the other fluidic sub-circuits. In this example implementation, the fluidic structure is configured to obtain a calibrated measurement of a biomarker of interest. In order to do so, the fluidic structure is configured to allow for three separate measurements to be obtained-one of the biomarker of interest in a sample, one of a positive control amount of the biomarker of interest, and one of a negative control (with the biomarker of interest absent). The leftmost fluidic sub-circuit in FIG. 18 is used to obtain a measurement of the biomarker of interest in the sample, the middle fluidic sub-circuit is used to obtain the positive control measurement, and the rightmost fluidic sub-circuit is used to obtain the negative control measurement.

When the clamping pressure zone is advanced further towards zone K, the fluid E/reagent mixture trapped in the volumes of zone D may be pressurized to a level that causes temporary seals that partition zone D from zone E to burst, allowing the separate portions of the fluid E/reagent mixture to be flowed into separate fluid passages defined by permanent seals within zone E. The leftmost fluid passage of zone E may have a sample collection interface 1842 that allows the fluid E/reagent mixture flowed into that fluid passage to come into contact with a previously collected sample of interest. For example, the sample collection interface may include surfaces of a breath collector module, such as is described in U.S. patent application Ser. No. 16/823,113, which is hereby incorporated herein for all purposes, configured to collect breath constituents from exhaled breath of a test subject. The fluid E/reagent mixture may act to elute such a collected sample from the sample collection interface 1842, thereby suspending it within the fluid E/reagent mixture.

Similarly, the middle passage may include a pre-defined amount of the biomarker of interest that is known with a particular accuracy; the fluid E/reagent mixture that is introduced into the middle passage may similarly elute the pre-defined amount of the biomarker within that passage, thereby suspending it within that fluid E/reagent mixture. The fluid E/reagent that is introduced into the rightmost passage does remains unadulterated.

After the biomarker in the leftmost and middle passages in zone E has been eluted by the fluid E/reagent mixture, henceforth simply referred to as "eluent," the clamping pressure zone may be advanced again to further pressurize the eluent in each of the three passages and cause temporary seals within each passage in between zone E and zone F to rupture, thereby allowing the eluent in each passage to advance to zone F. Zone F may be optional, and may be included if it is desired to isolate a portion of the collected sample for future analysis, e.g., to preserve a portion of the collected sample for future or subsequent use or analysis. As discussed above, zone F may be omitted and the eluent flowed directly into zone G. If zone F is used, a portion of the eluent (with whatever eluted biomarker is contained within it) in the leftmost passage may be directed into chamber 1846 by the pressure applied by the clamping pressure zone as the clamping pressure zone moves towards zone K. A heater element 1818*a* may be activated to locally heat the fluidic structure around the opening of the chamber 1846, thereby thermally bonding it to form a permanent seal. After the chamber 1846 is sealed shut, the clamping pressure zone can be advanced further towards zone K, causing temporary seals between zones F and G to rupture and allowing the eluent in each passage to advance to zone G.

Zone G may have several features that are replicated for each of the three fluidic sub-circuits. For example, each fluidic sub-circuit may have an area (represented by diagonal cross-hatching) in which another reagent that is specific to the reagent mixed with fluid E may be immobilized. For example, if the reagent mixed with fluid E is an antibody, the reagent that is immobilized in the cross-hatched area may be an antigen to that antibody that may bind with any unbound antibodies in the eluent, thereby immobilizing such antibodies. Antibodies in the eluent that previously bound with the eluted biomarker, however, would not bind to the immobilized antigen as their binding site(s) would already have bound to the biomarker.

The diagonal hatched area may also represent an optical window area, e.g., an optically transmissive region, that may be used to introduce light to and/or emitted from the region having the immobilized reagent. As discussed later below, the optical window area may eventually be used to obtain optical measurements of fluorescence or chemiluminescence (or other optical characteristic) of material that is located within the optical window area, thereby allowing for a measurement relating to the concentration and/or presence of the biomarker to be made. Finally, a heating element may be provided such that at least a portion of the immobilized reagent is located between the heating element and zone H. The heating element may be used to provide a localized thermal bond in the fluidic structure that acts to seal the passage within zone G. As noted, each of the passages in zone G may have a corresponding immobilized reagent, optical window area, and heater element.

Once the eluent has been pushed into zone G by advancement of the clamping pressure zone, the clamping pressure zone may optionally be moved back and forth by a small amount to promote circulation of the eluent over the area with the immobilized reagent. After the eluent has been allowed to incubate for a period of time such that most or all of the reagent in the eluent that is not bound to the biomarker of interest binds to the immobilized reagent, the clamping pressure zone may be advanced towards zone K again, causing the eluent to re-pressurize and cause the temporary seal separating zone G from zone H to be ruptured, thereby allowing the eluent to be pushed into zone H.

Zone H includes second fluid reservoirs 1806*b/c/d*, each of which may include a corresponding amount of fluid $\omega$, and a portion of the passage that is sealed off from the corresponding second fluid reservoir 1806*b*, 1806*c*, or 1806*d* by a corresponding temporary seal. The portions of the passage in zone H may be positioned, for example, over a fluid bypass recess, such as the example discussed earlier (and discussed in more detail below), that allows the eluent to escape past the clamping pressure zone within zone H. Thus, as the clamping pressure zone moves through zone H, the eluent that is trapped between the clamping pressure zone and the temporary seals between zones H and I may escape and flow back up into zone G (and possible into zones F or E). At the same time, when the clamping pressure zone reaches the second fluid reservoirs 1806*b/c/d*, the second fluid reservoirs 1806*b/c/d* may be caused to release the fluid $\omega$ portions contained therewithin and the resulting pressurization of the fluid $\omega$ portions may cause the temporary seals associated with each of the second fluid reservoirs 1806*b/c/d* to rupture, allowing the fluid w to be pushed into the passage portions within zone H. As fluid $\omega$ flows into the passage portions within zone H, it will act to push the eluent that is present in zone H past the clamping pressure zone, through zone G, and into zone F (and/or E). In some implementations, heater elements (not shown, but similar to the other heater elements discussed above) may be provided in locations corresponding to the locations of the ruptured temporary seals that existed between the second fluid reservoirs 1806*b/c/d* and the corresponding adjacent passages; these heater elements may be used to thermally bond the fluidic structure to as to produce permanent seals that replace the ruptured temporary seals at those locations once the fluid $\omega$ is evacuated from the second fluid reservoirs 1806*b/c/d*. The clamping pressure zone may then be moved relatively rapidly backwards, thus pushing the eluent and fluid $\omega$ towards zone A while allowing little of the eluent and fluid $\omega$ to escape past the clamping zone and flow towards zone K, so as to align with the heater elements provided in zone G. The heater elements may then be activated so as to thermally bond corresponding areas of the fluidic structure so as to form permanent seals that seal off all or most of the eluent and/or fluid $\omega$ from zones H/I/J/K and the portion of zone G that has the immobilized reagent.

The clamping pressure zone may then be further advanced to zone I; unlike previous such advancements, no fluid is driven forward through the passages into the adjoining passage segments in zone I; the temporary seals that exist at the boundary between zones I and J remain intact. Furthermore, the bypass recesses that were positioned under the passage segments in zone H may also extend into zone I and also into zone K.

As the clamping pressure zone moves into zone I, it may compress fluid a housed within third fluid reservoirs 1806*e/f/g* and fluid $\beta$ housed within fourth fluid reservoirs 1806*h/i/j*, thereby causing the temporary seals sealing the third fluid reservoirs 1806*e/f/g* and the fourth fluid reservoirs 1806*h/i/j* at the boundary between zones I and J to rupture. The clamping pressure zone may then be advanced through zone I to drive fluids α and β into zone J, where they may mix within each fluidic sub-circuit. Fluids α and β may, for example, be substrates that, when mixed together, form an indicator that may be activated so as to emit light when exposed to the reagents bound to the immobilized reagents in zone G.

As fluids α and β are forced into zone J, they may mix, which may include mixing that occurs when fluids α and β are pushed through a zig zag fluid path, or similar feature (such as is shown in zone C). The α/β mixtures may then be forced into zone K, where they may, by way of the fluid bypass recesses extending into zone K, flow past the clamping pressure zone and up through the passages and into zone G, where the α/β mixtures may then come into contact with the immobilized reagent and any reagents bound thereto. An optical measurement may then be performed through each window area of each fluidic sub-circuit in order to ascertain the amount of biomarker that was provided to each immobilization site. The measurements of the positive and negative control amounts of the biomarker of interest may allow the measurement of biomarker in the sample to be calibrated based on the control amounts, e.g., the measured quantity of the biomarker in the sample may be interpolated between the measured quantities of the positive and negative controls, and the calibrated amount of biomarker in the measured sample may then be estimated based on interpolating between the positive and negative control amounts in a similar manner.

Figure 19:
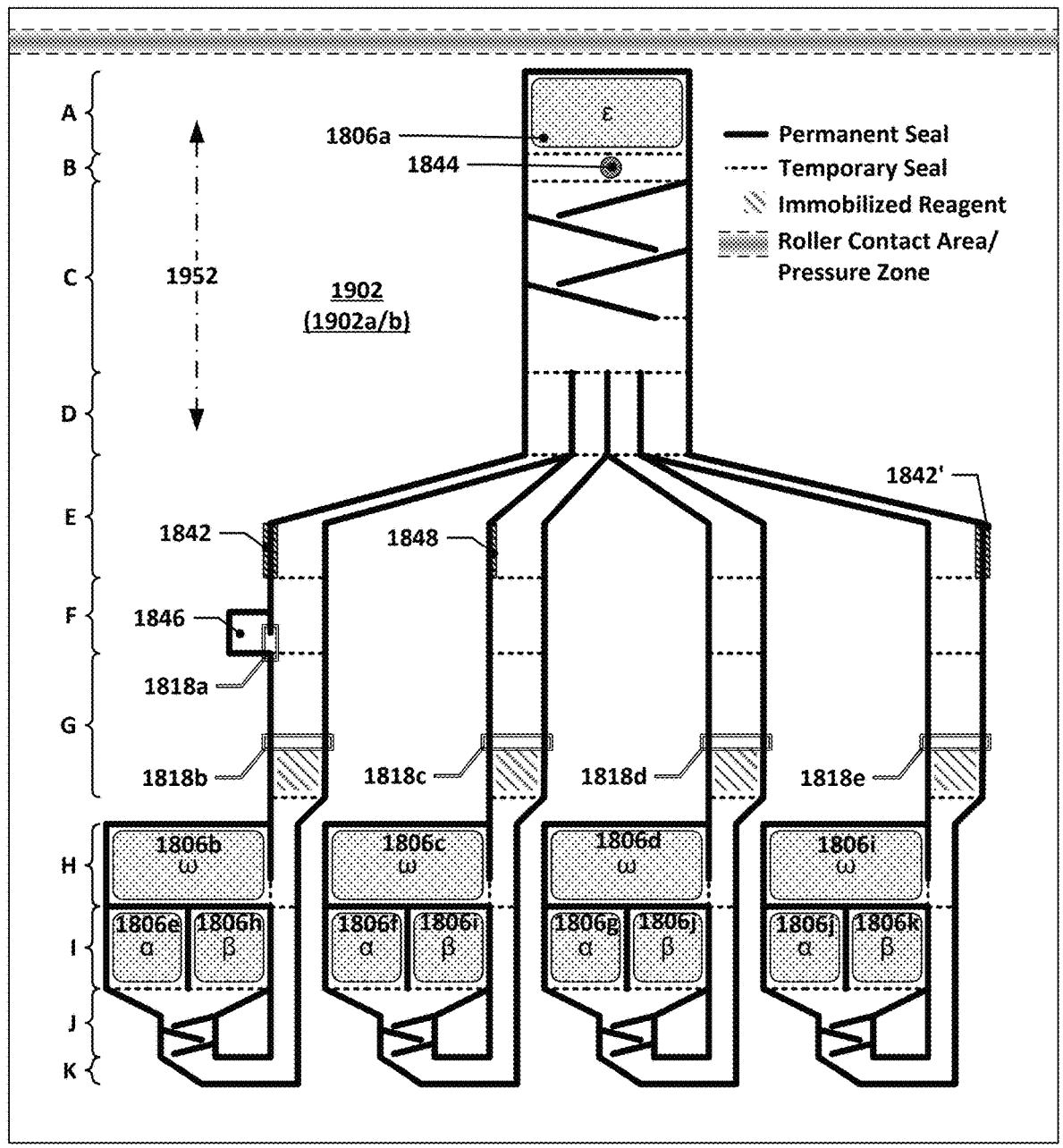
FIG. 19 depicts another example fluidic structure that may be used to measure a concentration of a biomarker or other material of interest.

FIG. 19 depicts a version of the fluidic structure of FIG. 18, but with four fluidic sub-circuits. The fourth fluidic sub-circuit, on the rightmost side, has a second sample collection interface 1842' that may, for example, be used to introduce a sample into the fluidic structure that has been collected from ambient air (as opposed to from a subject's lung exhalations), and to obtain similar measurements of that sample is obtained from the other three fluidic sub-circuits. Such a fluidic structure may be used to simultaneously obtain samples from, for example, a human subject's lungs, e.g., a breath sample, as well as from ambient air. In the latter case, a vacuum pump may be used to draw ambient air through a sampling system similar to that used to collect a breath sample from the test subject. Such a structure may permit the amount of biomarker in the test subject's sample to be adjusted to account for the amount of biomarker that may be in the ambient air. For example, if a reading of 40 units of biomarker is measured from the test subject's sample, but the ambient air is measured to have 30 units of biomarker present, then the test subject's biomarker measurement may be corrected to remove the portion thereof that may have been preexisting, i.e., 40 units minus 30 units, which would leave a corrected measurement of 10 units.

It will be understood that the fluidic structures of FIGS. 18 and 19 may use any of a variety of assays in order to identify a particular biomarker of interest, and that the basic architecture shown may be modified, as needed, to accommodate the fluidic requirements of any given assay, e.g., if an indicator that is stable in its final form is used, the dual fluid reservoirs containing the α and β fluids may be replaced with a single reservoir in each fluidic sub-circuit that contain that stable indicator; the mixing sections in zone J may also be omitted in some such cases since mixing may not be required. Alternatively, the dual fluid reservoirs of zone I may also be replaced with larger numbers of reservoirs, e.g., three or four reservoirs for each fluidic sub-circuit, allowing for more complex mixtures of reactants to be used.

In some implementations of the fluidic structures of FIGS. 18 and 19, the eluent may be N-cyclohexyl-2-hydroxyl-3-aminopropanesulfonic acid (CAPSO) mixed with 0.5% concentration dichloroacetic acid and the reagent or material 1844 may be a lyophilized anti-THC antibody that is conjugated to horseradish peroxidase (HRP). The immobilized reagent in such implementations may be bis(trimethylsilyl)acetamide (BSA)-THC that is adsorbed onto one or more surfaces of each passage in zone G of the fluidic structure, and the α and β fluids may be binary substrates that, when mixed, produce an HRP substrate. In such implementations, equal or near-equal volumes of eluted antibody are delivered to each fluidic sub-circuit, and varying amounts of the antibody in each such volume are bound to whatever THC is present within zone E of the corresponding fluidic sub-circuit. When the sample is then moved to zone G, whatever unbound antibody remains in the elution mixture is bound to the immobilized antibody, and the elution mixture is then washed out of zone G and the indicator (HRP) is introduced into zone G, where it binds to the immobilized antibody that remains. Subsequent luminescent or fluorescent emissions from the HRP may be measured to obtain an indication of the relative concentrations of immobilized antibody (and HRP) in each fluidic sub-circuit. Such concentrations will generally be inversely proportional to the amount of THC that was in zone E of each fluidic sub-circuit.

While the above specific examples provide some insight as to how particular fluidic circuits may be implemented in the context of the flexible fluidic circuit concepts discussed herein, it will be apparent that there may be many configurations of rollers and platens that may be suitable for use with the flexible substrate fluidic structures discussed above. Other roller/platen configurations can be employed, including one that does not use any platen at all, as described in U.S. Provisional Application No. 63/201,062, filed Apr. 9, 2021, titled "FLEXIBLE FLUIDIC CIRCUITS", which is incorporated herein by reference in its entirety.

Figure 20:
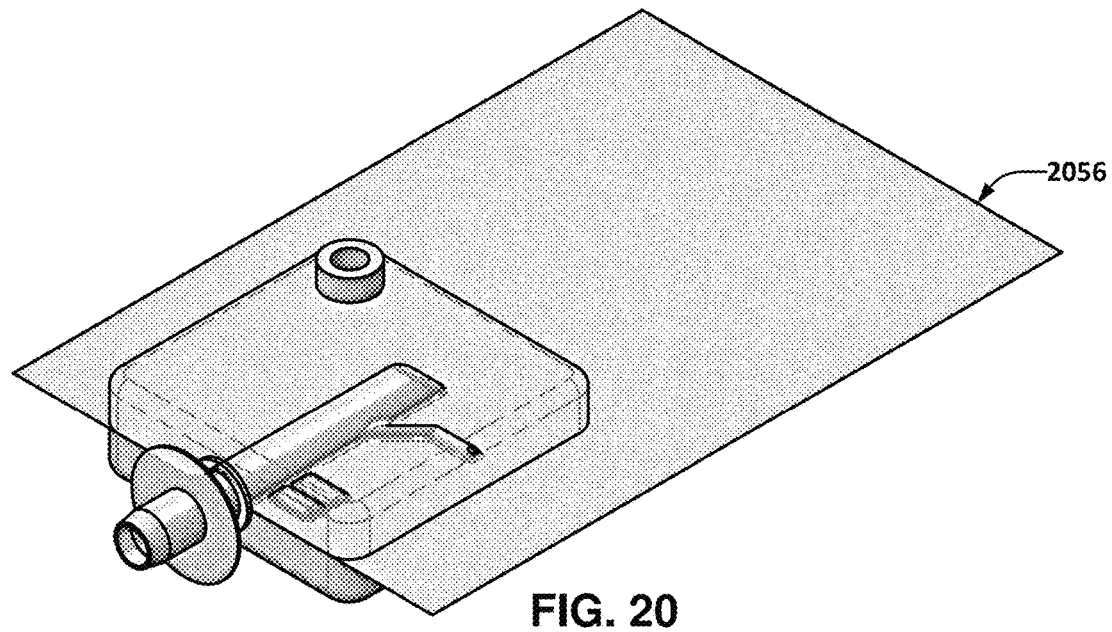
FIGS. 20 and 21 depict an example breath capture fluidic structure.
Figure 21:
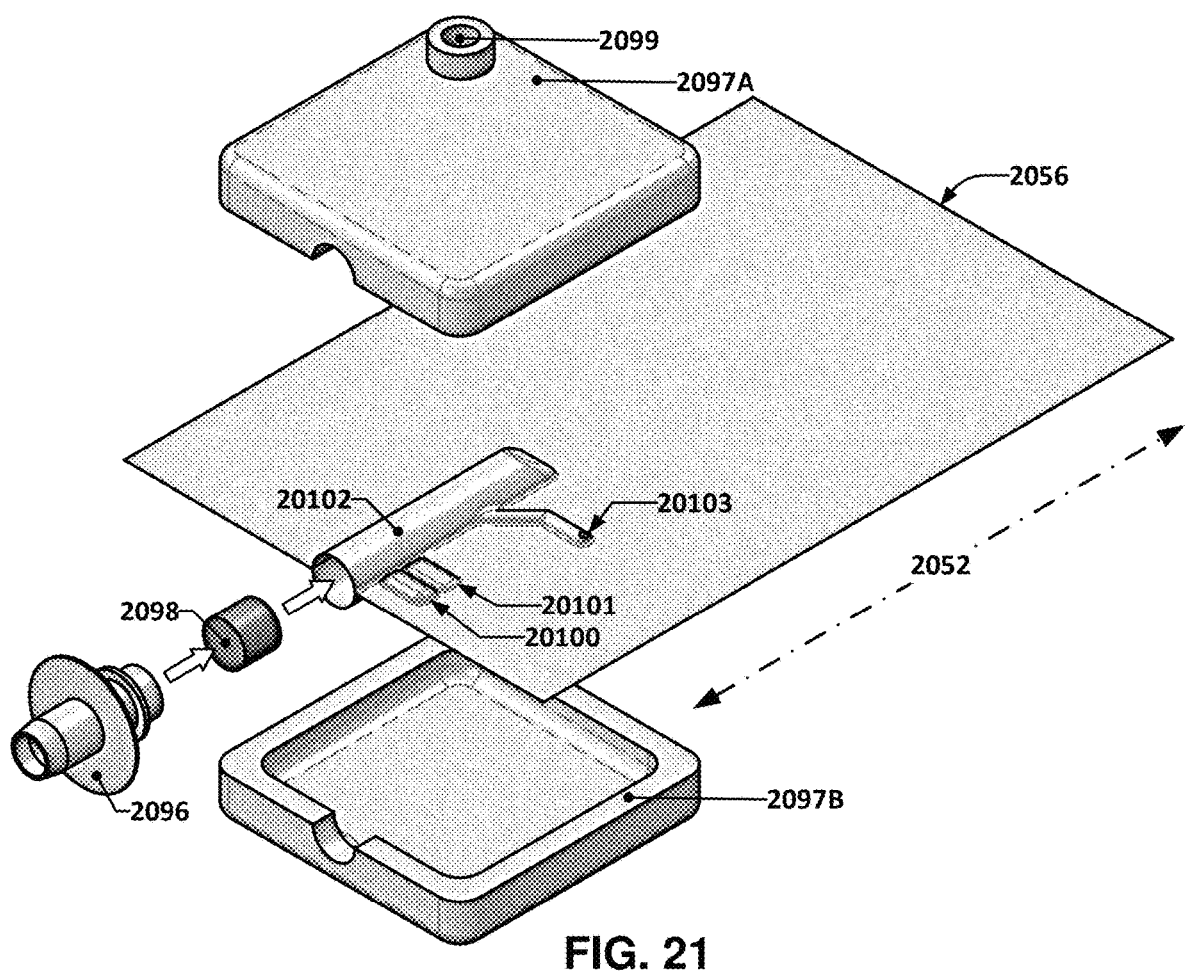

FIGS. 20 and 21 depict two views of a sample collection module, e.g., a breath collection module, that may be used to obtain a breath sample in a fluidic structure such as those discussed herein. In FIGS. 20 and 21, a fluidic structure 2056 is shown—the fluidic structure 2056 may have a plurality of different fluidic structures arranged therewithin, e.g. fluidic structures such as those discussed herein. Such additional fluidic structures are not depicted here since the focus of this example is on the fluidic structures shown in FIGS. 20 and 21.

As seen in FIGS. 20 and 21, the fluidic structure 2056 may include a main passage 20102 that is sized to accept capture media 2098 and a mouthpiece 2096. The main passage 20102 is shown in an "inflated" state, forming a generally circular tunnel, but can also be collapsed flat or nearly flat when the mouthpiece 2096 is removed and the main passage 20102 subjected to a clamping pressure zone. The capture media 2098 may, for example, be made of a porous, compressible material, e.g., foam, fibrous mesh, or other material that is sufficiently porous that a person is able to exhale therethrough but which is also able to provide a high surface-area-to-volume ratio that facilitates adsorption of breath constituents that, e.g., aerosols, molecular components, etc., that may be in breath that is exhaled therethrough.

The main passage 20102 may, at the end opposite the opening in which the mouthpiece 2096 is inserted, be sealed with a temporary seal. The temporary seal may act to seal the main passage off from the remainder of the downstream fluidic structures that may be present (and which are not shown).

In preparation for breath sample collection, the fluidic structure 2056 may be clamped between vacuum manifolds 2097A and 2097B. The vacuum manifolds 2097A and 2097B may, when clamped together with the fluidic structure 2056 clamped therebetween, seal against the fluidic structure 2056. At the same time, the mouthpiece 2096 that is inserted into the fluidic structure 2056 may act to push the portions of the fluidic structure 2056 that surround the mouthpiece 2096 into contact with the vacuum manifolds 2097A and 2097B.

When vacuum is drawn on the vacuum manifolds 2097A and 2097B, e.g., via vacuum port 2099, the pressure within the vacuum manifolds 2097A and 2097B may be reduced to sub-atmospheric levels. As a result, the portions of the fluidic structure 2056 that are subjected to such negative pressure and that are in fluidic communication with the ambient environment, e.g., the main passage 20102, may be caused to inflate due to the higher pressure that is applied by the ambient atmospheric pressure.

The main passage 20102 is fluidically connected with a vacuum assist port 20103, which may provide a source of assistive suction to help with breath sample collection. The main passage 20102 must be fluidically connected with either an outlet to ambient atmospheric pressure or with a sub-atmospheric pressure environment so that a subject is able to actually exhale through the main passage 20102 and the capture media contained therewithin. In implementations featuring a fluidic connection to an atmospheric pressure environment, the main passage 20102 may, for example, be fluidically connected with another passage that extends through the side walls of the vacuum manifolds, e.g., similar to how the main passage 20102 does. In implementations such as the depicted example, however, the main passage may be fluidically connected with a vacuum assist port 20103 that fluidically connects the interior of the main passage 20102 with the sub-atmospheric pressure environment within the clamped-together vacuum manifolds 2097A and 2097B. Thus, when a vacuum is drawn on the vacuum manifolds 2097A and 2097B via the vacuum port 2099, the sub-atmospheric pressure within the vacuum manifolds 2097A and 2097B will act to draw air from within the main passage 20102 into the vacuum manifolds 2097A and 2097B and out through the vacuum port 2099. This suction may assist in helping the subject breath through the capture media 2098.

A subject may, during testing, breath through the mouthpiece 2096 for a specified time period, number of exhalations, or total exhaled breath volume (e.g., as may be measured by a flow meter that may be included in the system), thereby facilitating the collection of a breath sample by the capture media 2098. Once the breath sample is collected, the mouthpiece 2096 may (optionally) be removed and the vacuum manifolds 2097A and 2097B unclamped, thereby releasing the fluidic structure 2056. A clamping pressure zone may then be applied to the fluidic structure 2056 and moved across the fluidic structure 2045 and along the axis 2052, starting at a location near the open end of the main passage 20102 and moving towards the closed end of the main passage 20102.

In doing so the clamping pressure zone may cause a temporary seal for elution blister or chamber 20100 to rupture or release, allowing an eluent contained therewithin to flow into, for example, a lyophilized material blister or chamber 20101 before being directed to flow into the main passage 20102. The elution blister 20100 may be fluidically connected with the lyophilized material blister 20101 via a temporary seal that ruptures when the elution blister is pressurized by the advancement of the clamping pressure zone along the axis 2052. Similarly, the lyophilized material blister 20101 may be fluidically connected with the main passage 20102 by a temporary seal that ruptures when the clamping pressure zone advances further along the axis 2052. The temporary seal that seals the lyophilized material blister 20101 off from the main passage 20102 may be positioned such that is proximate the capture media 2098.

Thus, as the clamping pressure zone moves across the fluidic structure 2056, the clamping pressure zone may first force the eluent into the lyophilized material blister 20101, where it may mix with the lyophilized material contained therewithin, and then force the mixture into the main passage 20102, where it may absorb into the capture media, thereby eluting captured breath sample. If desired, the clamping pressure zone may be moved back and forth across the elution blister 20100 and the lyophilized material blister 20101 to facilitate mixing of the eluent with the lyophilized material and/or dissolution of the lyophilized material in the eluent. After allowing the eluent to elute the collected breath sample, the clamping pressure zone may be caused to move further along the axis 2052, thereby driving the eluent from the capture media 2098 and towards the temporary seal at the end of the main passage 20102. When the clamping pressure zone continues to move towards the temporary seal, the resulting pressure increase in the eluted breath sample solution may cause the temporary seal to rupture, thereby allowing the eluted breath sample solution to be delivered to various downstream fluidic structures, e.g., in order to facilitate analysis.

While numerous specific fluidic structures have been described above in conjunction with the implementations depicted in the figures, various other implementations of fluidic structures will also be understood to fall within the scope of this disclosure, including fluidic structures that combine two or more of the fluidic structures discussed herein, or that may blend the features of two fluidic structures together.

In some embodiments, the fluidic structure can be provided within a system. For instance, the system can comprise: a fluidic structure including: a first portion of material, wherein the first portion of material is a flexible, inelastic material; and a second portion of material. Furthermore, one or more portions of the first portion of material and the second portion of material are sealed together so as to provide one or more seals that define a boundary of a fluidic circuit interposed between the first portion of material and the second portion of material. Such boundaries can be used to define chambers, reservoirs, channels, passages, and the like. For instance, the fluidic circuit can include one or more passages and one or more fluid-containing reservoirs that are arranged such that when a clamping pressure is applied to the fluidic structure and then moved across the fluidic structure from a first location to a second location, the movement of the clamping pressure causes fluids within the fluidic circuit to move through the fluidic circuit in a predetermined manner in order to perform an analysis (e.g., any described herein).

In some embodiments, the first portion of material stretches 1% or less when subjected to a pressure of 10 psi. In other embodiments, the first portion of material stretches 10% or less when subjected to a pressure of 10 psi. In further embodiments, the second portion of material is also a flexible, inelastic material. The first and second portion can be a part of the same material or of different materials.

Such materials, or portions thereof, can be further sealed together so as to provide one or more temporary seals. For instance, each temporary seal can be configured to fluidically isolate two portions of the fluidic circuit from one another within the fluidic structure, and each temporary seal can be configured to rupture at a pressure that is less than the pressure at which each seal is configured to rupture. In some embodiments, at least one of the portions of the fluidic circuit has an internal pressure that is less than ambient air pressure. In other embodiments, at least one of the portions of the fluidic circuit has substantially no fluid in it when sealed by a corresponding one of the temporary seals.

In particular embodiments, at least one of the portions of the fluidic circuit has a free volume within it when sealed by a corresponding one or more of the temporary seals that is less than 1% of the volume within that portion when pressurized to above ambient pressure.

In some embodiments, the system further includes one or more fluid reservoirs, wherein: each fluid reservoir is sandwiched between the first portion of material and the second portion of material; each fluid reservoir contains a corresponding amount of a liquid; and each fluid reservoir is within the boundary of the fluidic circuit. In particular embodiments, at least one of the one or more fluid reservoirs includes a burstable pouch or blister, separate from the first portion of material and the second portion of material, within which the corresponding liquid is contained.

The system can include further components to actuate one or more seals. For instance, the system can include a platen and a roller, wherein: the platen, the roller, and the fluidic structure are positioned such that the fluidic structure is interposed between the roller and the platen; the roller and the platen contact opposing sides of a portion of the fluidic structure and apply a clamping load on the fluidic structure; and the system is configured to permit the roller and the fluidic structure to translate relative to each other along a first axis that is nominally perpendicular to an axis of rotation of the roller, and relative translation between the roller and the fluidic structure along the first axis causes the roller to rotate about the axis of rotation and the clamping load to translate across the fluidic structure and along the first axis.

It will be understood that the above-discussed examples are simply representative implementations of the concepts discussed herein, and other implementations of the concepts discussed herein are considered within the scope of this disclosure as well. The disclosure is not limited to only the specific implementations discussed above.

The preceding description of the disclosed embodiments is provided to enable any person skilled in the art to make or use the claimed subject matter. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the claims and the principles and novel features disclosed herein.

It is to be understood that the above disclosure, while focusing on a particular example implementation or implementations, is not limited to only the discussed example, but may also apply to similar variants and mechanisms as well, and such similar variants and mechanisms are also considered to be within the scope of this disclosure.

What is claimed is:

1. A method for evaluating an analyte level in a breath sample, the method comprising:
   determining an amount of an analyte captured from a breath sample obtained from a subject;
   comparing the determined amount of the analyte captured from the breath sample to a background level for the analyte in an ambient air sample that is obtained at a location and at a time in which the breath sample is obtained from the subject; and
   indicating whether or not the determined amount of the analyte captured from the breath sample exceeds the background level;
   wherein the background level is correlated with a baseline maximum level of THC in the ambient air sample.

2. The method of claim 1, wherein said comparing comprises:
   subtracting the background level from the determined amount of the analyte, to provide a normalized level for the analyte in the breath sample; and
   comparing the normalized level to a threshold level.

3. The method of claim 2, wherein the analyte is tetrahydrocannabinol (THC), and wherein the threshold level is correlated with a baseline maximum level of THC in breath associated with consumption of THC outside a window of THC-associated impairment.

4. The method of claim 3, wherein the threshold level is correlated with an average amount of THC in breath between 2 and 3 hours after inhalation.

5. The method of claim 4, wherein the threshold level is less than 10 pg/L of breath.

6. The method of claim 1, further comprising, prior to said determining:
   eluting the breath sample from a material by using an extraction solution, wherein the material is configured to capture liquid drops or particles from the breath sample.

7. The method of claim 1, further comprising, prior to said comparing:
   determining an amount of the analyte captured from the ambient air sample.

8. The method of claim 1, wherein said determining comprises:
   conducting an assay, thereby forming a labeled complex comprising a detectable label; and
   measuring a detectable signal arising from the labeled complex, wherein the detectable signal is indicative of a presence or an absence of the analyte in the breath sample and/or an ambient air sample.

9. The method of claim 8, wherein said measuring is done in situ in the corresponding reaction channel.

10. The method of claim 9, wherein said measuring is done ex situ of the corresponding reaction channel in a separate fluidically-connected channel or chamber on the test cartridge.

11. The method of claim 1, wherein said determining comprises:
   exposing the analyte to a detectable label, thereby forming a labeled complex;
   capturing the labeled complex with a capture agent to form a captured complex; and
   measuring a detectable signal arising from the captured complex, wherein the detectable signal is indicative of a presence or an absence of the analyte in the breath sample and/or the ambient air sample.

12. The method of claim 1, wherein the analyte is tetrahydrocannabinol (THC).

13. The method of claim 12, further comprising:
   determining an amount of a second analyte captured from the breath sample obtained from the subject.

14. The method of claim 13, wherein the second analyte is ethanol, and both the analyte and the second analyte are measured from the same breath sample.

15. The method of claim 1, wherein the background level is from about 0.01-5 pg/L of ambient air.

16. The method of claim 1, further comprising, prior to said determining: obtaining the breath sample from the subject.

17. The method of claim 16, wherein the breath sample is obtained from the subject after exposing the subject to a well-ventilated area for at least 15 minutes.

18. The method of claim 1, further comprising: drawing a portion of the breath sample exhaled by the subject into a corresponding reaction channel in a test cartridge with negative pressure.

19. The method of claim 1, further comprising: drawing a portion of the ambient air sample into a corresponding reaction channel in a test cartridge with negative pressure.

20. The method of claim 19, wherein the test cartridge of at least one of the breath sample or the ambient air sample comprises a microfluidic device.

21. The method of claim 1, further comprising: drawing an equal portion of each of (i) the breath sample as drawn into a corresponding reaction channel into a corresponding evidence channel; and (ii) an ambient air sample as drawn into another corresponding reaction channel into another corresponding evidence channel.

22. The method of claim 1, wherein said determining the amount of the analyte captured from the breath sample includes utilizing an immunoassay.

23. The method of claim 22, wherein the immunoassay comprises a surface-based antibody-down immunoassay, a surface-based antigen-down immunoassay, a noncompetitive immunoassay, a heterogeneous competitive immunoassay, or a homogeneous competitive immunoassay.

24. The method of claim 1, wherein said indicating comprises a visible and/or audible signal and/or readout on a display associated with a device on which said determining and said comparing is conducted.

25. The method of claim 1, further comprising wirelessly transmitting data corresponding to one or more of said determining the amount of analyte captured from the breath sample obtained from the subject, said comparing the determined amount of the analyte from the breath sample to a threshold level and the background level in the ambient air sample.

26. A system comprising:
   one or more modules, including at least a first module that is configured to perform operations that include:
   (a) determining an amount of THC in a breath sample obtained from a subject;
   (b) comparing the determined amount of THC from the breath sample to a background level for THC in an ambient air sample that is obtained at a location and at a time in which the breath sample is obtained from the subject; and
   (c) indicating whether or not the determined amount of THC captured from the breath sample exceeds the background level;
   wherein said comparing comprises:
   subtracting the background level from the determined amount of the THC, to provide a normalized level for the THC in the breath sample; and
   comparing the normalized level to a threshold level; and
   wherein the threshold level is correlated with an average amount of THC in breath between 2 and 3 hours after inhalation, and wherein the background level is correlated with a baseline maximum level of THC in the ambient air at a location and at a time in which the breath sample was obtained from the subject.

27. The system of claim 26, wherein the background level is correlated with a baseline maximum level of THC the ambient air sample.

28. The system of claim 26, wherein the one or more modules include a processor-executable software module to perform (a) through (c).

29. The system of claim 28, wherein the one or more modules include a breath capture module to capture the breath sample.

* * * * *